US007691604B1

(12) United States Patent
Dong et al.

(10) Patent No.: US 7,691,604 B1
(45) Date of Patent: Apr. 6, 2010

(54) MRG POLYPEPTIDES AND NUCLEIC ACIDS ENCODING THE SAME

(75) Inventors: Xinzhong Dong, Pasadena, CA (US); David J. Anderson, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/704,707

(22) Filed: Nov. 3, 2000

Related U.S. Application Data

(60) Provisional application No. 60/222,344, filed on Aug. 1, 2000, provisional application No. 60/202,027, filed on May 4, 2000.

(51) Int. Cl.
*C12N 15/12* (2006.01)
*C07K 14/705* (2006.01)

(52) U.S. Cl. ............. 435/69.1; 435/252.3; 435/320.1; 536/23.5

(58) Field of Classification Search .............. 536/23.1, 536/23.5; 435/320.1, 325, 455, 69.1
See application file for complete search history.

(56) References Cited

U.S. PATENT DOCUMENTS

| 5,320,941 | A | * | 6/1994 | Young et al. ............... 435/7.23 |
| 5,516,659 | A |   | 5/1996 | Nii et al. |
| 5,525,718 | A |   | 6/1996 | Ohashi et al. |
| 5,738,999 | A |   | 4/1998 | Segerson et al. |
| 6,228,616 | B1 |  | 5/2001 | Bandman et al. |
| 6,262,246 | B1 | * | 7/2001 | Gerald et al. ............... 536/23.5 |

FOREIGN PATENT DOCUMENTS

| JP | 2000-23676 | | 1/2000 |
| WO | WO 99/32519 | | 1/1999 |
| WO | WO 99/32519 | * | 7/1999 |
| WO | WO 00/64928 | | 11/2000 |
| WO | WO 01/19983 | | 3/2001 |
| WO | WO 01/36471 | | 5/2001 |
| WO | WO 01/36473 | | 5/2001 |
| WO | WO 01/44472 | | 6/2001 |
| WO | WO 01/48015 | | 7/2001 |
| WO | WO 01/57085 A2 | | 8/2001 |
| WO | WO 01/62788 | | 8/2001 |
| WO | WO 01/62797 | | 8/2001 |
| WO | WO 03/023010 A2 | | 3/2003 |

OTHER PUBLICATIONS

Gerhold et al., It's genes! EST access to human genome content, 1996, Bioessays, vol. 18, pp. 973-981.*
Attwood, The babel of bioinformatics, 2000, Science, vol. 290, pp. 471-473.*
Wells et al., The chemokine information source: identification and characterization of novel chemokines using the worldwideweb and expressed sequence tag databases, 1997, Journal of Leukocyte Biology, vol. 61, pp. 545-550.*
Lopez et al., Microcorrespondence, 1999, Molecular Microbiology, vol. 32, pp. 881-891.*
Russell et al., Structural features can be unconserved in proteins with similar folds, 1994, J. Mol. Biol., vol. 244, pp. 332-350.*
Accession S78653, May 7, 1993.*
Ngo et al., Computational complexity, protein structure prediction, and the levinthal paradox, 1994, The Protein Folding Problem and Tertiary Structure Prediction, pp. 491-495.*
Rudinger, Characteristics of the amino acids as components of peptide hormone sequence, 1976, Peptide Hormones, pp. 1-7.*
Adler et al., "A Novel Family of Mammalian Taste Receptors," *Cell*, vol. 100, pp. 693-702 (2000).
Buck et al., "A Novel Multigene Family May Encode Odorant Receptors: A Molecular Basis for Odor Recognition," *Cell*, vol. 65, pp. 175-187(1991).
Cao et al., "Primary afferent tachykinins are required to experience moderate to intense pain," *Nature*, vol. 392, pp. 390-394 (1998).
Chandrashekar et al., "T2Rs Function as Bitter Taste Receptor," *Cell*, vol. 100, pp. 703-711 (2000).
Caterina et al., "Impaired Nociception and Pain Sensation in Mice Lacking the Capsaicin Receptor," *Science*, vol. 288, pp. 306-313 (2000).
Caterina et al., "Sense and specificity: a molecular identity for nociceptors," *Current Opinion in Neurobiology*, vol. 9, pp. 525-530 (1999).
Caterina et al., "The capsaicin receptor: a heat-activated ion channel in the pain pathway," *Nature*, vol. 389, pp. 816-824 (1997).
Dulac et al., "A Novel Family of Genes Encoding Putative Pheromone Receptors in Mammals," *Cell*, vol. 83, pp. 195-206 (1995).
Friedel et al., "A Novel 7-Transmembrane Receptor Expressed in Nerve Growth Factor-Dependent Sensory Neurons," *Molecular and Cellular Neuroscience*, vol. 17, pp. 31-40 (2001).
Gonzalez et al., "Characterization of Gene Expression in Human Trabecular Meshwork Using Single-Pass Sequencing of 1060 Clones," *IOVS*, vol. 41, No. 12, pp. 3678-3693 (2000).
Gouardéres et al, "Dual Localization of Neuropeptide FF Receptors in the Rat Dorsal Horn," *Synapse*, vol. 35, pp. 45-52 (2000).
Hinuma et al., "New neuropeptides containing carboxy-terminal RF amide and their receptor in mammals," *Nature Cell Biology*, vol. 2, pp. 703-708 (2000).
Hunt et al., "The Molecular Dynamics of Pain Control," *Nature Reviews*, vol. 2, pp. 83-91 (2001).
Jackson et al., "The *mas* oncogene encodes an angiotensin receptor," *Nature*, vol. 335, pp. 437-440 (1988).
Ma et al., "NEUROGENIN1 and NEUROGENIN2 control two distinct waves of neurogenesis in developing dorsal root ganglia," *Genes & Development*, vol. 13, pp. 1717-1728 (1999).

(Continued)

*Primary Examiner*—John D Ulm
(74) *Attorney, Agent, or Firm*—Knobbe Martens Olson & Bear LLP

(57) ABSTRACT

The invention relates generally to novel genes expressed in normal but not neurogenin-1-deficient animals. The invention relates specifically to a novel family of G protein-coupled receptors and a novel family of two-transmembrane segment proteins that are expressed in dorsal root ganglia, and a method of screening for genes specifically expressed in nociceptive sensory neurons.

12 Claims, 12 Drawing Sheets

OTHER PUBLICATIONS

Malmberg et al., "Preserved Acute Pain and Reduced Neuropathic Pain in Mice Lacking PKCT," *Science*, vol. 278, pp. 279-283 (1997).
Matsunami et al., "A family of candidate taste receptors in human and mouse," *Nature*, vol. 404, pp. 601-604 (2000).
Matsunami et al., "A Multigene Family Encoding a Diverse Array of Putative Pheromone Receptors in Mammals," *Cell*, vol. 90, pp. 775-784 (1997).
Michael et al., "Differential Expression of the mRNA for the Vanilloid Receptor Subtype 1 in Cells of the Adult Rat Dorsal Root and Nodose Ganglia and Its Downregulation by Axotomy," *The Journal of Neuroscience*, vol. 19, No. 5, pp. 1844-1854 (1999).
Monnot et al., "Cloning and Functional Characterization of a Novel *mas*-Related Gene, Modulating Intracellular Angiotensin II Actions," *Molecular Endocrinology*, vol. 5, No. 10, pp. 1477-1487 (1991).
Panula et al., "Neuropeptide FF and modulation of pain," *Brain Research*, vol. 848, pp. 191-196 (1999).
Price et al., "Structure of a Molluscan Cardioexcitatory Neuropeptide," *Science*, vol. 197, pp. 670-671 (1977).
Ross et al., "RTA, a candidate G protein-coupled receptor: Cloning, sequencing, and tissue distribution," *Proc. Natl. Acad. Sci. USA*, vol. 87, pp. 3052-3056 (1990).
Snider et al, "Tackling Pain at the Source: New Ideas about Nociceptors," *Neuron*, vol. 20, pp. 629-632 (1998).
Stucky et al., "Isolectin $B_4$- Positive and -Negative Nociceptors Are Functionally Distinct," *The Journal of Neuroscience*, vol. 19, No. 5, pp. 6497-6505 (1999).
Tominaga et al., "The Cloned Capsaicin Receptor Integrates Multiple Pain-Producing Stimuli," *Neuron*, vol. 21, pp. 531-543 (1998).
Troemel et al., "Divergent Seven Transmembrane Receptors Are Candidate Chemosensory Receptors in *C. elegans*," *Cell*, vol. 83, pp. 207-218 (1995).
Vilim et al., "Gene for Pain Modulatory Neuropeptide NPFF: Induction in Spinal Cord by Noxious Stimuli," *Molecular Pharmacology*, vol. 55, pp. 804-811 (1999).
Xu et al., "Effects of (1DMe) NPYF, a synthetic neuropeptide FF analogue, in different pain models," *Peptides*, vol. 20, pp. 1071-1077 (1999).
Young et al., "Isolation and Characterization of a New Cellular Oncogene Encoding a Protein with Multiple Potential Transmembrane Domains," *Cell*, vol. 45, pp. 711-719 (1986).
Kress, M. et al., "Capsaicin, protons and heat: new excitement about nociceptors," *TiPS*, vol. 20, pp. 112-(1999).
Aimes et al., "Cloning, expression, and characterization of chicken tissue inhibitor of metalloproteinase-2 (TIMP-2) in normal and transformed chicken embryo fibroblasts," *J. Cell. Physiol.*, 174(3):342-352 (1998).
Ambrose et al., "Genomic organization of the mouse dystrobrevin gene: comparative analysis with the dystrophin gene," *Genomics*, 3993): 359-369 (1997).
Barnett et al., "Nucleotide sequence and predicted functions of the entire *Sinorhizobium leiloti* pSymA megaplasmid," *Proc. Natl. Acad. Sci. U.S.A.*, 98(17):9883-9888 (2001).
Breitbart et al., "Complete nucleotide sequence of the fast skeletal troponin T gene," *J. Mol. Biol.*, 188(2):313-324 (1986).
Breitbart et al., "Intricate combinatorial patterns of exon splicing generate multiple regulated troponin T isoforms from a single gene," *Cell*, 41(1):67-82 (1985).
Caminci et al., "High-efficiency full-length cDNA cloning," *Methods in enzymology*, 303: 19-44 (1999).
Chuang et al., "A 29 kDa intracellular chloride channel p64h1 is associated with large dense-core vesicles in rat hippocampal neurons." *J. Neurosci.*, 19(8):2919-2928 (1999).
Dempsey et al., "The human HNRPD locus maps to 4q21 and encodes a highly conserved protein," *Genomics*, 49(3):378-384 (1998).
Dong et al., "A diverse family of gpcrs expressed in specific subsets of nociceptive sensory neurons," *Cell*, 108(5):619-632 (2001).
Edwards, J.C., "A novel p64-related C1-channel: subcellular distribution and nephron segment-specific expression," *Am. J. Physiol.*, 276(3): F398-F408 (1999).
Garfinkel et al., "Cloning and characterization of cDNA sequences corresponding to myosin light chains 1, 2, and 3, troponin-C, troponin-T, alpha-tropmyosin, and alpha-actin," *J. Biol. Chem.*, 257(18):11078-11088 (1982).
GenBank Database Entry: Accession No. AB014605, "*Homo sapiens* mRNA for KIAA0705 protein, complete cds," Ohara et al., Feb. 6, 1999.
GenBank Database Entry: Accession No. AB019373, "Mus musculus mRNA for ERK5, complete cds," Kamakura et al., Released Oct. 13, 1999.
GenBank Database Entry: Accession No. AB020734, "Oryzias latipes gene for polypeptide elongation factor 1 alpha, complete cds," Kinoshita, M., Released Jun. 3, 1999.
GenBank Database Entry: Accession No. AB029485, "Mus musculus ARIP1 mRNA for activin receptor interacting protein 1, complete cds," Shoji et al., Released Mar. 2, 2000.
GenBank Database Entry: Accession No. AB032996, "*Homo sapiens* mRNA for KIAA1170 protein, partial cds," Ohara et al., Released Nov. 11, 1999.
GenBank Database Entry: Accession No. AB051486, "*Homo sapiens* mRNA for KIAA1699 protein, partial cds," Ohara et al., Released Feb. 7, 2001.
GenBank Database Entry: Accession No. AB056512, "Arthrobacter globiformis genes for probable aminopeptidase, lipoamide dehydrogenase, probable dihydrolipoamide acyltransferase, partial and complete cds.", Released Feb. 4, 2001.
GenBank Database Entry: Accession No. AE000874, "Methanobacterium thermoautotrophicum from bases 922625 to 934189 (section 80 of 148) of the complete genome," Smith, D. R., Released Nov. 15, 1997.
GenBank Database Entry: Accession No. AE004000, "Xylella fastidiosa 9a5c, section 146 of 229 of the complete genome," Simpson et al., Released Jun. 15, 2001.
GenBank Database Entry: Accession No. AE004551, "*Pseudomonas aeruginosa* PA01, section 112 of 529 of the complete genome," Stover et al., Released Aug. 30, 2000.
GenBank Database Entry: Accession No. AE007228, "*Sinorhizobium meliloti* plasmid pSymA section 34 of 121 of the complete plasmid sequence," Barnett et al., Released Aug. 15, 2001.
GenBank Database Entry: Accession No. AF004664, "Gallus gallus tissue inhibitor of metalloproteinase-2 precursor (TIMP-2) mRNA, complete cds," Aimes et al., Released Sep. 28, 2001.
GenBank Database Entry: Accession No. AF022982, "*Caenorhabditis elegans* cosmid T23B12, complete sequence," Waterson, R., Released Sep. 14, 2001.
GenBank Database Entry: Accession No. AF034863, "Rattus norvegicus synaptic scaffolding molecule (S-SCAM) mRNA, complete cds," Hirao et al., Released Aug. 10, 1998.
GenBank Database Entry: Accession No. AF038563, "*Homo sapiens* membrane associated guanylate kinase 2 (MAGI-2) mRNA, complete cds," Wood et al., Released Sep. 16, 1999.
GenBank Database Entry: Accession No. AF057160,"*Homo sapiens* putative poly (ADP-ribosyl) transferase (PARPL) mRNA, complete cds," Still, I.H., Released Feb. 8, 2000.
GenBank Database Entry: Accession No. AF080475, "*Homo sapiens* thyroglobulin gene, exon 39," Rivolta et al., Released May 9, 2000.
GenBank Database Entry: Accession No. AF097330, "*Homo sapiens* H1 chloride channel mRNA, complete cds," Edwards, J.C., Released Jun. 14, 1999.
GenBank Database Entry: Accession No. AF100956, Mus musculus major histocompatibility locus class II region; Fas-binding protein Daxx (DAXX) gene, partial cds; Bing1 (BING1), tapasin (tapasin), Ra1GDS-like factor (RFL), KE2 (KE2), BING4 (BING4), beta1, 3-galactosyl transferase (beta1,3-galactosyl transferase) ribosomal protein subunit S18 (RPS18), Sacm21 (Sacm21), H2K1 (b) (H2-K1 (b)), RING1 (RING1), KE6a (KE6a), KE4 (KE4), RXRbeta (RXRbeta), collagen alpha-2 (XI) (COLA11A2), H2-) alpha (H2-Oalpha), RING3 (RING3), H2-M alpha (XI) (COLA11A2), H2-) alpha (H2-Oalpha), RING3 (RING3), H2-M alpha (H2-M alpha), H2-M beta 2 (H2-M beta2), and H2-M beta1 (H2-M beta1) genes, complete cds; and LMP2 gene, partial cds, Rowen et al., Released Nov. 3, 1998.

GenBank Database Entry: Accession No. AF109196 "*Homo sapiens* intracellular chloride channel p64H1 mRNA, complete cds," Chuang et al., Released Apr. 20, 1999.
GenBank Database Entry: Accession No. AF109907, "*Homo sapiens* S164 gene, partial cds; PS1 and hypothetical protein genes, complete cds; and S171 gene, partial cds," Rowen, L., Released Dec. 23, 1998.
GenBank Database Entry: Accession No. AF126159, "Mus musculus big MAP kinase 1a (BMK1) mRNA, alternatively spliced, complete cds," Luo et al., Released Apr. 2, 2001.
GenBank Database Entry: Accession No. AF126160, "Mus musculus big MP kinase 1B (BMK1) mRNA, alternatively spliced, complete cds," Luo et al., Released Apr. 2, 2001.
GenBank Database Entry: Accession No. AF126161, "Mus musculus big MAP kinase 1B(BMK1) mRNA, alternatively spliced," Luo et al., Released Apr. 2, 2001.
GenBank Database Entry: Accession No. AF1340819, "Rattus norvegicus S-SCAm beta mRNA, complete cds," Hirao et al., Released Jan. 27, 2000.
GenBank Database Entry: Accession No. AF132734, "*Homo sapiens* REC8 mRNA, partial cds," Luo et al., Released May 1, 2000.
GenBank Database Entry: Accession No. AF158255, "*Homo sapiens* vault protein mRNA, complete cds," Kickhoefer et al., Sep. 14, 1999.
GenBank Database Entry: Accession No. AF205032, "Carpodacus mexicanus Came-DAB1 and serine-threonine kinase genes, complete sequence," Hess et al., Released Sep. 25, 2000.
GenBank Database Entry: Accession No. AF241798, "Mus musculus 2 P domain potasium channel (Kcnk3) gene, exon 2 and complete cds," Goldstein, S.A.N., Released Jul. 3, 2000.
GenBank Database Entry: Accession No. AF261146, Description: NID:8547318 Branchiostoma fioride homeoprotein (EmxA) mRNA, complete cds, Williams et al., Released Oct. 16, 2000.
GenBank Database Entry: Accession No. AF319553,."*Homo sapiens* TNFRSF19L mRNA, complete cds," Sica et al., Released Jul. 25, 2001.
GenBank Database Entry: Accession No. AF324792, "Ehrlichia canis phosphoribosylaminoimidazole carboxylase (purK) gene, complete cds; major outer membrane protein gene cluster 2, complete sequence; and u6 gene, partial cds," Ohashi et al., Released Apr. 11, 2001.
GenBank Database Entry: Accession No. AF349460, "Ovis aries uterine milk protein gene, 5' flanking region, 5' UTR and partial cds," Fleming et al., Released May 12, 2001.
GenBank Database Entry: Accession No. AF380839, "*Homo sapiens* secretory protein SEC8 mRNA, complete cds," Sha et al., Released May 28, 2001.
GenBank Database Entry: Accession No. AJ005424, "Rattus norvegicus mRNA for BMK1/ERK5 protein, partial," Yang, C.C., Released Oct. 2, 1998.
GenBank Database Entry: Accession No. AJ011907. "Klebsiella pneumoniae DNA sequence for transposon Tn5711, partial," Albiger et al., Released Oct. 14, 1998.
GenBank Database Entry: Accession No. AK001624, "*Homo sapiens* cDNA FLJ10762 fis, clone NT2RP4000008, moderately similar to Chlorine Channel Protein P64," Isogai et al., Released Aug. 31, 2001.
GenBank Database Entry: Accession No. AK011625, "Mus Musculus 10 days embryo cDNA, RIKEN full-length enriched library, clone:2610029P10, full insert sequence," Adachi et al., Released Jul. 5, 2001.
GenBank Database Entry: Accession No. AK019862, "Mus musculus 11 days pregnant adult female ovary and uterus cDNA, RIKEN full-length enriched library, clone: 5031400M07, full insert sequence," Adachi et al., Released Jul. 5, 2001.
GenBank Database Entry: Accession No. AK022751, "*Homo sapiens* cDNA FLJ12689 fis, clone NT2RM4002565, highly similar to Mus musculus Sec8 mRNA," Isogai et al., Released Sep. 29, 2000.
GenBank Database Entry: Accession No. AK027688, "*Homo sapiens* cDNA FLJ14782 fis, clone NT2RP4000524, highly similar to Mus musculus Sec8 mRNA," Isogai et al., Released May 15, 2001.
GenBank Database Entry: Accession.No. AK027899, "*Homo sapiens* cDNA FLJ14993 fis, clone Y79AA1001874, weakly similar to OX40L Receptor Precursor," Isogai et al., Released May 15, 2001.

GenBank Database Entry: Accession No. AL117424, "*Homo sapiens* mRNA; cDNA DKFZp566G223 (from clone DKFZp566G223); complete cds," Koehrer et al., Released Mar. 10, 2001.
GenBank Database Entry: Accession No. AL122012, "Leishmania major Friedlin chromosome 23 cosmid L8342, complete cds," Masuy et al., Released Dec. 15, 1999.
GenBank Database Entry: Accession No. AL357523, "Streptomyces coelicolor cosmid 9C5," Cerdeno et al., Released Jun. 1, 2000.
GenBank Database Entry: Accession No. AP000510, "*Homo sapiens* genomic DNA, chromosome 6p21.3, HLA Class I region, section 9/20," Hirakawa et al., Released Aug. 22, 2001.
GenBank Database Entry: Accession No. AP001137, "*Homo sapiens* genomic DNA, chromosome 21q21.1-q21.2, LL56-APP region, clone: B812P3," Hattori et al., Released Jan. 26, 2001.
GenBank Database Entry: Accession No. AP001278, "Oryza sativa genomic DNA, chromosome 1, clone: P0434D08," Sasaki et al., Released Nov. 22, 2000.
GenBank Database Entry: Accession No. AP001539, "Oryza sativa genomic DNA, chromosome 1, clone: P0708G02," Sasaki et al., Released Jul. 28, 2000.
GenBank Database Entry: Accession No. AP001667, "*Homo sapiens* genomic DNA, chromosome 21q, section 11/105," Hattor et al., Released May 30, 2000.
GenBank Database Entry: Accession No. AP001681, "*Homo sapiens* genomic DNA, chromosome 21Q, section 25/105," Hattori et al., Released May 30, 2000.
GenBank Database Entry: Accession No. AP001800, "Oryza sativa genomic DNA, chromosome 1, PAC clone: P0443E05," Sasaki et al., Released Jul. 15, 2000.
GenBank Database Entry: Accession No. AP002835, "Oryza sativa genomic DNA, chromosome 1, PAC clone: P0417G05," Sasaki et al., Released Feb. 7, 2001.
GenBank Database Entry: Accession No. AP003011, "Mesorhizobium loti DNA, complete genome, section 18/21," Kaneko et al., Released May 15, 2001.
GenBank Database Entry: Accession No. AR001253, "Sequence 1 from patent US 5738999," Released Dec. 4, 1998.
GenBank Database Entry: Accession No. AR149778, "Sequence 2 from patent US 6228616," Released Aug. 8, 2001.
GenBank Database Entry: Accession No. AX099247, "Sequence 1 from Patent WO0119983," Deleersnijder et al., Released Apr. 2, 2001.
GenBank Database Entry: Accession No. AX147794, "Sequence 39 from Patent WO01346818," Released Jun. 8, 2001.
GenBank Database Entry: Accession No. AX147812, "Sequence 57 from Patent WO0136473," Vogeli et al., Released Jun. 8, 2001.
GenBank Database Entry: Accession No. AX147824, "Sequence 69 from Patent WO0136473," Vogeli et al., released Jun. 8, 2001.
GenBank Database Entry: Accession No. AX148178, "Sequence 19 from Patent WO0136471," Chen et al., Released Jun. 8, 2001.
GenBank Database Entry: Accession No. AX148188, "Sequence 29 from Patent WO0136471," Chen et al., Released Jun. 8, 2001.
GenBank Database Entry: Accession No. AX167357, "Sequence 1 from Patent WO0144472," Released Jul. 3, 2001.
GenBank Database Entry: Accession No. AX188692, "Sequence 3 from Patent WO0148015," Lind et al., Released Aug. 8, 2001.
GenBank Database Entry: Accession No. AX188700, "Sequence 11 from Patent WO0148015," Lind et al., Released Aug. 8, 2001.
GenBank Database Entry: Accession No. AX188730, "Sequence 41 from Patent WO0148015," Released Aug. 8, 2001.
GenBank Database Entry: Accession No. AX188734, "Sequence 45 from Patent WO0148015," Released Aug. 6, 2001.
GenBank Database Entry: Accession No. AX230115, "Sequence 2 from Patent WO0162797," Released Sep. 11, 2001.
GenBank Database Entry: Accession No. AX230151, "Sequence 28 from patent W)0162797," Released Sep. 11, 2001.
GenBank Database Entry: Accession No. AX233369, "Sequence 12 from patent WO0162788," Released Sep. 11, 2001.
GenBank Database Entry: Accession No. AY042193, "Mus musculus G protein-coupled receptor (MrgA3) mRNA, complete cds," Dong et al., Released Oct. 15, 2001.

GenBank Database Entry: Accession No. AY042194, "Mus musculus RF-amide G protein-coupled receptor (Mrga4) mRNA, complete cds," Dong et al., Released Sep. 14, 2001.
GenBank Database Entry: Accession No. AY042195, "Mus musculus G protein-coupled receptor (MrgA5) gene, complete cds," Dong et al., Released Sep. 14, 2001.
GenBank Database Entry: Accession No. AY042197, "Mus musculusG protein-coupled receptor (MrgA7) gene, complete cds," Dong et al., Released Sep. 14, 2001.
GenBank Database Entry: Accession No. AY042198, "Mus musculus G protein-coupled receptor (MrgA8) gene, complete cds," Dong et al., Released Sep. 14, 2001.
GenBank Database Entry: Accession No. AY042199, "Mus musculus G protein-coupled receptor (MrgB1) gene, complete cds," Dong et al., Released Sep. 14, 2001.
GenBank Database Entry: Accession No. AY042210, "Mus musculus G protein-coupled receptor (MrgE) gene, complete cds," Dong et al., Released Sep. 14, 2001.
GenBank Database Entry: Accession No. AY042213, "*Homo sapiens* G protein-coupled receptor (MRGX1) gene, complete cds," Dong et al.; Released Sep. 14, 2001.
GenBank Database Entry: Accession No. AY042214, "*Homo sapiens* G protein-coupled receptor (MRGX2) gene, complete cds," Dong et al., Released Sep. 14, 2001.
GenBank Database Entry: Accession No. AY042215, "*Homo sapiens* G protein-coupled receptor (MRGX3) gene, complete cds," Dong et al., Released Sep. 14, 2001.
GenBank Database Entry: Accession No. AY042216, "*Homo sapiens* G protein-coupled receptor (MRGX4) gene, complete cds," Dong et al.; Released Sep. 14, 2001.
GenBank Database Entry: Accession No. GB:E31936. Description: NID:13018636 Seven-pass transmembrane receptor protein ERG9 Released Jun. 8, 2001.
GenBank Database Entry: Accession No. NM_014287, "*Homo sapiens* pM5 protein (PM5), mRNA," Released Nov. 2, 2000.
GenBank Database Entry: Accession No. AF177217, "Canis familiaris matrix metalloproteinase-2 (MMP-2) mRNA, partial cds," Jahic et al., Released May 4, 2000.
GenBank Database Entry: Accession No. BC002058, "Mus musculus, Similar to zinc finger protein 101, clone MGC:6101 Image: 3593763, mRNA, complete cds," Strausberg, R., Released Jul. 12, 2001.
GenBank Database Entry: Accession No. BC007404, "*Homo sapiens*, Similar to mitogen-activated protein kinase 7, clone MGC:2148 Image:3009873, mRNA, complete cds," Strausberg, R., Released Jul. 12, 2001.
GenBank Database Entry: Accession No. BC009963, "*Homo sapiens*, mitogen-activated protein kinase 7, cline MGC:15371 Image:4300124, mRNA, complete cds," Strausberg, R., Released Jul. 12, 2001.
GenBank Database Entry: Accession No. BC010610, "*Homo sapiens*, clone Image:4214515, mRNA, partial cds," Strausberg, R., Released Jul. 12, 2001.
GenBank Database Entry: Accession No. BC012444, "*Homo sapiens*, Similar to chloride intracellular channel 4, clone MGC: 8812 Image: 3861372, mRNA, complete cds," Strausberg, R., Released Aug. 20, 2001.
GenBank Database Entry: Accession No. BC013201, "*Homo sapiens*, Similar to chromosome 6 open reading frame 31, clone MGC:18030 Image:3924575, mRNA, complete cds," Strausberg, R., Released Aug. 29, 2001.
GenBank Database Entry: Accession No. D16817, "Rattus norvegicus mRnA for metabotropic glutamate receptor mGluR7, complete cds," Okamoto, N., Released Feb. 1, 2000.
GenBank Database Entry: Accession No. D79999, "*Homo sapiens* mRNA for KIAA0177 protein, parital cds," Ohara et al., Released Oct. 6, 2001.
GenBank Database Entry: Accession No. E05718, "Asparaginilendopeptidase gene," Released Sep. 29, 1997.
GenBank Database Entry: Accession No. E31931, "Seven-pass transmembrane receptor protein ERG5," Released Febuary 7, 2001.
GenBank Database Entry: Accession No. E31932, "Seven-pass transmembrane receptor protein ERG5," Released Feb. 7, 2001.
GenBank Database Entry: Accession No. E31933, Seven-pass transmembrane receptor protein ERG5, Released Feb. 7, 2001.
GenBank Database Entry: Accession No. E31936, "Seven-pass transmembrane receptor proetin ERG9," Tsuyoshi et al., Released Feb. 7, 2001.
GenBank Database Entry: Accession No. L11748, "Methanobacterium thermoautotrophicum methyl coenzyme M reductase system component A2 gene, complete cds," Released Jun. 12, 1993.
GenBank Database Entry: Accession No. L19109, "Rattus noregicus (clone R2(CT1)) heparin-binding fibroblast growth factor receptor 2 (intracellular domain) mRNA, 3' end," released Jun. 26, 1996.
GenBank Database Entry: Accession No. L19110., "Rat (clone R2(CT2)) heparin-binding fibroblast growth factor receptor 2 (intracellular domain) mRNA, 3'end," Released Aug. 26, 1993.
GenBank Database Entry: Accession No. I20815, "Sequence 10 from patent US 5,516,659," Released Oct. 7, 1996.
GenBank Database Entry: Accession No. I22095, "Sequence 11 from patent US 5525718," Released Oct. 7, 1996.
GenBank Database Entry: Accession No. LMFP265, "Leishmania major Friedlin chromosome 13 PAC P265," Robben et al., Released Sep. 4, 2001.
GenBank Database Entry: Accession No. M15202, "Rattus norvegicus troponin T class proteins, alternatively spliced products, complete cds," Released Jun. 12, 2000.
GenBank Database Entry: Accession No. M21027, "Ovis aries uterine milk protein precursor A mRNA, complete cds," Released Oct. 20, 2000.
GenBank Database Entry: Accession No. NC_000868, "Pyrococcus abyssi, complete genome," Released Jul. 9, 2001.
GenBank Database Entry: Accession No. NC_000916, "Methanobacterium thermoautotrophicum delta H complete genome," Released Sep. 19, 2001.
GenBank Database Entry: Accession No. NM_001949, "*Homo sapiens* transcription factor 3 (E2F3) mRNA, complete cds," Released Feb. 6, 2001.
GenBank Database Entry: Accession No. NM_002138, "*Homo sapiens* heterogeneous nuclear ribonucleoprotein D (AU-rich element RNA-binding protein 1, 37kD) (HNRPD), transcript variant 3, mRNA," Released May 16, 2001.
GenBank Database Entry: Accession No. NM_002377, "*Homo sapiens* MAS1 oncogene (Mas1), mRNA," Released Oct. 31, 2000.
GenBank Database Entry: Accession No. NM_006437, "*Homo sapiens* ADP-ribosyltransferase (NAD+; poly (ADP-ribose) polymerase)-like 1 (ADPRTL1), mRNA," Released Feb. 3, 2001.
GenBank Database Entry: Accession No. NM_006765, "*Homo sapiens* Putative prostate cancer tumor suppressor (N33), mRNA," Released Nov. 2, 2000.
GenBank Database Entry: Accession No. NM_012508, "Rattus norvegicus ATPase isoform 2, Na+K+ transporting, beta polypeptide 2 (Atp2b2), mRNA," Released Nov. 1, 2000.
GenBank Database Entry: Accession No. NM_031369, "*Homo sapiens* heterogeneous nuclear ribonucleoprotein D (AU-rich element RNA-binding protein 1, 37kD) (HNRPD), transcript variant 2, mRNA," Released May 16, 2001.
GenBank Database Entry: Accession No. NM_031370, "*Homo sapiens* heterogeneous nuclear ribonucleoprotein D (AU-rich element RNA-binding protein 1, 37 kD) (HNRPD), transcript variant 1, mRNA," Released May 16, 2001.
GenBank Database Entry: Accession No. NM_032975, "*Homo sapiens* dystrobrevin, alpha (DTNA), transcript variant alpha, mRNA," Released Jul. 19, 2001.
GenBank Database Entry: Accession No. NM_032980, "*Homo sapiens* dystrobrevin, alpha (DTNA), transcript variant alpha, mRNA," Released Jul. 19, 2001.
GenBank Database Entry: Accession No. U25278, "Human ERK5 mRNA, complete cds, " Zhou, G., Released Nov. 16, 1995.
GenBank Database Entry: Accession No. U29725, "Human BMK1 alpha kinase mRNA, complete cds," Lee et al., Released Dec. 5, 1995.
GenBank Database Entry: Accession No. U29726, "Human BMK1 beta kinase mRNA, complete cds," Lee et al., Released Dec. 5, 1995.

GenBank Database Entry: Accession No. U29727, "Human BMK1 gamma kinase mRNA, complete cds," Lee et al., Released Dec. 5, 1995.
GenBank Database Entry: Accession No. X56192, "D. discoideum mRNA for ribosomal acidic phosphoprotein P2," Coloma, A., Released Mar. 20, 1991.
GenBank Database Entry: Accession No. X57398, "Human mRNA for pM5 protein," Templeton, N.S., Released Septbmer 26, 2001.
GenBank Database Entry: Accession No. XM_004872, "*Homo sapiens* atrophin-1 interacting protein 1; activin receptor interacting protein 1 (KIAA0705), mRNA," Released Oct. 16, 2001.
GenBank Database Entry: Accession No. XM_008323, "*Homo sapiens* mitogen-activated protein kinase 7 (MAPK7), mRNA," Released Oct. 16, 2001.
GenBank Database Entry: Accession No. XM_010013, "*Homo sapiens* E1A binding protein p300 (EP300), mRNA," Released Oct. 16, 2001.
GenBank Database Entry: Accession No. XM_012279, "*Homo sapiens* ADP-ribosyltransferase (Nad+; poly (ADP-ribose) polymerase)-like 1 (ADPRTL1), mRNA," Released Oct. 16, 2001.
GenBank Database Entry: Accession No. XM_012584, "*Homo sapiens* hypothetical gene supported by X57398; NM_014287 (LOC95345), mRNA," Released Aug. 27, 2001.
GenBank Database Entry: Accession No. XM_016735, "*Homo sapiens* hypothetical protein FLJ21736 (FLJ21736), mRNA," Released Oct. 16, 2001.
GenBank Database Entry: Accession No. XM_017189, "*Homo sapiens* atrophin-1 interacting protein 1; activin receptor interacting protein 1 (KIAA0705), mRNA," Releasd Oct. 16, 2001.
GenBank Database Entry: Accession No. XM_027247, "*Homo sapiens* PM5 protein (PM5), mRNA., " Released Oct. 16, 2001.
GenBank Database Entry: Accession No. XM_027359, "*Homo sapiens* hypothetical gene supported by NM_014287," Released Oct. 16, 2001.
GenBank Database Entry: Accession No. XM_035133, "*Homo sapients* hypothetical protein FLJ14993, mRNA," Released Oct. 16, 2001.
GenBank Database Entry: Accession No. XM_037487, "*Homo sapiens* similar to poly (AdP-ribosyl) transferase-like 1; H5 proline-rich; PARP-related; I-alpha-I-related; vault protein, 193-kDa; poly (Adp-ribose) synthetase (*H. sapiens*) (LOC95103), mRNA," Released Aug. 27, 2001.
GenBank Database Entry: Accession No. XM_037847, "*Homo sapiens* neurexophilin 3 (NXPH3), mRNA," Released Oct. 16, 2001.
GenBank Database Entry: Accession No. XM_041759, "*Homo sapiens* comeodesmosin (CDSN), mRNA," Released Aug. 27, 2001.
GenBank Database Entry: Accession No. XM_043815, "*Homo sapiens* hypothetical protein FLJ21736 (FLJ21736), mRNA," Released Octboer 16, 2001.
GenBank Database Entry: Accession No. XM_045046, "*Homo sapiens* mitogen-activated protein kinase 7 (MAPK7), mRNA," Released Oct. 16, 2001.
GenBank Database Entry: Accession No. XM_045047, "*Homo sapiens* mitogen-activated protein kinase 7 (MAPK7), mRNA," Released Oct. 16, 2001.
GenBank Database Entry: Accession No. XM_045048, "*Homo sapiens* mitogen-activated protein kinase 7 (MAPK7), mRNA," Released Oct. 16, 2001.
GenBank Database Entry: Accession No. XM_045907, "*Homo sapiens* KIAA1170 protein (KIAA1170), mRNA," Released Oct. 16, 2001.
GenBank Database Entry: Accession No. XM_050246, "*Homo sapiens* secretory protein SEC8 (SEC8), mRNA," Released Aug. 27, 2001.
GenBank Database Entry: Accession No. XM_052950, "*Homo sapiens* mitogen-activated protein kinase 7 (MAPK7), mRNA," Released Oct. 16, 2001.
GenBank Database Entry: Accession No. XM_053380, "*Homo sapiens* similar to poly (ADP-ribosyl) transferase-like 1; H5 proline-rich; PARP-related; I-alpha-I-related; vault potein, 193-kDa; poly (ADP-ribose) synthetase (*H. sapiens*) (LOC95103), mRNA," Released Aug. 27, 2001.
GenBank Database Entry: Accession No. XM_054516, "*Homo sapiens* similar to dystrobrevin, alpha (*H. sapiens*)," Released Aug. 28, 2001.
GenBank Database Entry: Accession No. XM_054519, "*Homo sapiens* similar to dystrobrevin, alpha (*H. sapiens*)," Released Aug. 28, 2001.
GenBank Database Entry: Accession No. Y15484, "*Canis familiaris* gene encoding retinal guanylate cyclase E," Veske, A., Released Jul. 17, 1998.
GenBank Database Entry: Accession No. Z50046, "*S.cerevisiae* chromosome IV cosmid 8358," Barrell et al., Released Aug. 11, 1997.
GenBank Database Entry: Accession No. Z83820, "Human DNA sequence from PAC 215K18 on chromosome X contains ESTs, and STS," Mistry, S., Released Nov. 23, 1999.
GenBank Database Entry: Accession No. Z84470, "Human DNA sequence from PAC 411B6 on chromosome X," Bird, C., Released Nov. 23, 1999.
GenBank Database Entry: Accession No. Z84816, "Human DNA sequence from PAC 2A2 on chromosome X contains ESTs," Deadman, R. Released Nov. 23, 1999.
GenBank Database Entry: Accession No. Z98682, "*Bacillus subtilis* genomic DNA 23.9kB fragment," Glaser et al., Released Aug. 19, 1997.
GenBank Database Entry: Accession No. Z99111, "*Bacillus subtilis* complete genome (section 8 of 21): from 1394791 to 1603020," Kunst et al., Released Nov. 26, 1997.
GenBank DatabaseEntry: Accession No. NC_001136, "*Saccharomyces cerevisiae* chromosome IV, complete chromosome sequence," *Saccharomyces* Genome Database, Released Nov. 3, 2001.
Goffeau et al., "Life with 6000 genes," *Science*, 274(5287):546 (1996).
Hattori et al., "The DNA sequence of human chromosome 21. The chromosome 21 mapping and sequencing consortium," *Nature*, 405(6784):311-319.
Hess et al., "MHC class II pseudogene and genomic signature of a 32-kb cosmid in the house finch (*Carpodacus mexicanus*)," *Genome Res.*, 10(5): 613-623 (2000).
Hirao et al., "A novel multiple PDZ domain-containing molecule interacting with N-methyl-D-aspartate receptors and neuronal cell addhesion proteins," *J. Biol. Chem.*, 273(33):21105-21110 (1998).
Hirao et al., "Three isoforms of synaptic scaffolding molecule and their characterization. Multimerization between the isoforms and their interaction with N-methyl-D-aspartate receptors and SAP90/PSD-95-associated protein," *J. Biol. Chem.*, 275(4):2966-2972 (2000).
Hirosawa et al., "Characterization of cDnA clones selected by the GeneMark analysis from size-fractionated cDNA libraries from human brain," *DNA Res.*, 6(5):329-33 (1999).
Ing and Roberts, "The major progesterone-modulated proteins secreted into the sheep uterus are members of the serpin superfamily of serine protease inhibitors," *J. Biol. Chem.*, 264(6): 3372-3379 (1989).
Ishii et al., "The FEZ1 gene at chromosome 8p22 encodes a leucine-zipper protein, and its expression is altered in multiple human tumors," *Proc. Natl. Acad. Sci. U.S.A.*, 96(7):3928-3933 (1999).
Ishikawa et al., "The complete sequences of 100 new cDNA clones from brain which can code for large proteins in vitro," *Journal DNA Res.*, 5 (3):169-176 (1998).
Ivens et al., "A physical map of the Leishmania major Friedlin genome," *Genome Res.*, 8(2):135-145 (1998).
Jackson et al., "The mas oncogene encodes an angiotensin receptor," *Nature*, 335(6189):437-440 (1988).
Jacq et al., "The nucleotide sequence of *Saccharyomyces cerevisiae* chromosome IV," *Nature*, 387(6632 Suppl):75-78 (1997).
Jean et al., "The nuclear protein PH5P of the inter-alpha-inhibitor superfamily: a missing link between poly (ADP-ribose) polymerase and the inter-alpha-inhibitor family and a novel actor of DNA repair?," *FEBS Lett.*, 446(1):6-8 (1999).
Kajita et al., "The UUAG-specific RNA binding protein, heterogeneous nuclear ribonucleoprotein DO. Common modular structure and binding properties of the x2RBD-Gly family," *J. Biol. Chem.*, 270(38):22167-22175 (1995).

Kamakura et al., "Activation of the protein kinase ERK5/BMK1 by receptor tyrosine kinases. Identification and characterization of a signaling pathway to the nucleus," *J. Biol. Chem.*, 274(37):26563-26571 (1999).

Kaneko et al., "Complete genome structure of the nitrogen-fixing symbiotic bacterium *Mesorhizobium loti*," *DNA Res.*, 7(6):331-338 (2000).

Kawai et al., The RIKEN Genome Exploration Research Group Phase II Team and the FANTOm Consortium, "Functional annotation of a full-length mouse cDNA collection," *Nature*, 409: 685-690 (2001).

Khurana et al., "(CA) repeat polymorphism in the chromosome 18 encoded dystrophin-like protein," *Hum. Mol. Genet.*, 3950; 841 (1994).

Kickhoefer et al., "The 193-kD vault protein, VDARP, is a novel poly (ADP-ribose) polymerase," *J. Cell Biol.*, 146(5): 917-928 (1999).

Kiledjian et al., "Identification of AUF1 (heterogeneous nuclear ribonucleoprotein D) as a component of the alpha-globin mRNA stability complex," *Mol. Cell. Biol.*, 17(8):4870-4876 (1997).

Kunst et al., "The complete genome sequence of the gram-positive bacterium *Bacillus subtilis*," *Nature*, 390 (6657):249-256 (1997).

Lee et al., "Primary structure of BMK1: a new mammalian map kinase," *Biochem. Biophys. Res. Commun.*, 213(2):715-724 (1995).

Lees et al., "The retinoblastoma protein binds to a family of E2F transcription factors," *Mol. Cell. Biol.*, 13(12):7813-7825 (1993).

Loftus et al., "Genome duplications and other features in 12 Mb of DNA sequence from human chromosome 16p and 16q," *Genomics*, 60(3): 295-308 (1999).

Lopes et al., "Proton block and voltage gating are potassium-dependent in the cardiac leak channel kcnk3," *J. Biol. Chem.*, 275(22):16969-16978 (2000).

Ma et al., "NEUROGENIN1 and NEUROGENIN2 control two distinct waves of neurogenesis in developing dorsal root ganglia," Genes & Development 13: 1717-1728 (1999).

MacGrogan et al., "Structure and methylation-associated silencing of a gene within a homozygously deleted region of human chromosome band 8p22," Genomics, 3591):55-65 (1996).

Marchese et al., "Novel GPCRs and their endogenous ligands: expanding the boundaries of physiology and pharmacology," TiPS 20: 370-375 (1999).

Medford et al., "A novel mechanism of alternative RNA splicing for the developmentally regulated generation of troponin T isoforms from a single gene," *Cell*, 28(2):409-421 (1984).

Metzinger et al., "Dystrobrevin deficiency at the sarcolemma of patients with muscular dystrophy," *Hum. Mol. Genet.*, 6(7):1185-1191 (1997).

Nagase et al., "Predication of the coding sequences of unidentified human genes. V. The coding sequences of 40 new genes (KIAA0161-KIAA0200) deduced by analysis of cDNA clones from human cell line KG-1," DNA Res., 3(1):17-24 (1996).

Nagase et al., "Predictin of the coding sequences of unidentified human genes. XIX. The complete sequences of 100 new cDNA clones from brain which code for large proteins in vitro," *DNA Res.*, 7(6): 347-355 (2000).

Newey et al., "Alternative splicing of dystrobrevin regulates the stoichiometry of syntrophin binding to the dystrophin protein complex," *Curr. Biol.*, 10(20): 1295-1298 (2000).

Ohashi et al., "Analysis of Transcriptionally Active Gene Clusters of Major Outer Membrane Protein Multigene Family in *Ehrlichia canis* and *E. chaffeensis*," Infect. Immun., 69(4): 2083-2091 (2001).

Ohashi et al., "Cloning and characterization of multigenes encoding the immunodomiriant 30-kilodalton major outer membrane proteins of *Ehrlichia canis* and application of the recombinant protein for serodiagnosis," J. Clin. Microbiol., 36(9): 2671-2680 (1998).

Okatmoto et al., "Molecular characterization of a new metabotropic glutamate receptor mGluR7 coupled to inhibitory cyclic Amp signal transduction," *J. Biol. Chem.*, 269(2): 1231-1236 (1994).

Ozawa et al., "From dystrophinopathy to sarcoglycanopathy: evolution of a concept of muscular dystrophy," *Muscle Nerve*, 21(4): 421-438 (1998).

Pierce et al., "Differential activities of E2F family members: unique functions in regulating transcription," *Mol. Carcinog.*, 22(3):190-198 (1998).

Prieto et al., "Nucleotide sequence of a cNDA encoding acidic ribosomal phosphoprotein P2 in Dictyostelium discoideum, " *Nucleic Acids Res.*, 19(6);1341 (1991).

Rabin et al., "Human ros1 and mas1 oncogenes located in regions of chromosome 6 associated with tumor-specific rearrangements," *Oncogene Res.*, 1(2):169-178 (1987).

Riesewijk et al., "The MAS proto-oncogene is not imprinted in humans," *Genomics*, 35(2):380-382 (1996).

Sadoulet-Puccio et al., "Cloning and characterization of the human homologue of a dystrophin related phosphoprotein found at t he Torpedo electric organ post-synaptic membrane," Hum. Mol. Genet., 5(4):489-496 (1996).

Sadoulet-Puccio et al., "The genomic organization of human dystrobrevin," *Neurogenetics*, 1(1): 37-42 (1997).

Shibata et al., "RIKEN integrated sequence analysis (RISA) system—384-format sequencing pipeline with 384 multicapillary sequencer," *Genome research*, 10(11):1757-1771 (2000).

Shoji et al., "Identification and characterization of a PDZ protein that interacts with activin type II receptors," *J. Biol. Chem.*, 275(8):5485-5492 (2000).

Shull et al., "Molecular cloning of two isoforms of the plasma membrane $Ca^{2+}$-transporting ATPase frm rat brain. Structural and functional domains exhibit similarity to $Na+,K+$- and other cation transport ATPases," *J. Biol. Chem.*, 263(18):8646-8657 (1988).

Sica et al., "RELT, a new member of the tumor necrosis factor receptor superfamily, is selectively expressed in hematopoietic tissues and activates transcription factor NF-kappaB," Blood, 97(9):2702-2707 (2001).

Simpson et al., "The genome sequence of the plant pathogen *Xylella fastidiosa*. The *Xylella fastidiosa* consortium of the Organization for Nucleotide Sequencing and Analysis," *Nature*, 406(6792):151-157 (2000).

Smith et al., "Complete genome sequence of *Methanobacterium thermoautotrophicum* detlaH: functional analysis and comparative genomics," *J. Bacteriol.*, 179(22):7135-7155 (1997).

Still et al., "Identification of a novel gene (ADPRTL1) encoding a potential Poly (ADP-ribosyl) transferase protein," *Genomics*, 62(30: 533-536 (1999).

Stover et al., "Complete genome sequence of *Pseudomonas aeruginosa* PA01, an opportunistic pathogen," *Nature*, 406(6799):959-964 (2000).

Straub et al., "Muscular dystrophies and the dystrophin-glycoprotein complex," *Curr Opin Neurol*, 10(2): 168-175 (1997).

Templeton et al., "Cloning and characterization of a novel human cDnA that has DNA homology to conserved regions of the collagenase gene family," Genomics, 12(1):175-6 (1992).

The *C. elegans* Sequencing Consortium, "Genome sequence of the nematode *C. elegans*: a platform for investigating biology," *Science*, 282(5396):2012-2018 (1998).

Van Soest et al., "A locus for autosomal recessive pseudoxanthoma elasticum, with penetrance of vascular symptoms in carriers, maps to chromosome 16p13.1," Genome Res., 7(8): 830-834(1997).

Veske, A., "Organization of the canine gene encoding the E isoform of retinal guanylate cyclase (cGC-E) and exclusion of its involvement in the inherited retinal dystrophy of the Swedish Briard and Briard-beagle dogs," *Biochim. Biophys. Acta*, 1372 (1): 69-77 (1998).

Wagner et al., "Localization and physical mapping of genes encoding the A+U-rich element RNA-binding protein AUF1 to human chromosomes 4 and X," Genomics, 34(2):219-222 (1996).

Wagner et al., "Structure and genomic organization of the human AUF1 gene: alternative pre-mRNA splicing generates four protein isoforms," *Genomics*, 48(2):195-202 (1998).

Wiemann et al., "Toward a Catalog of Human Genes and Proteins: Sequencing and Analysis of 500 Novel Complete Protein Coding Human cDNAs," Genome Res., 11(3): 422-435 (2001).

Williams et al., "An Amphioxus Emx Homeobox Gene Reveals Duplication During Vertebrate Evolution," *Mol. Biol. Evol.*, 17(10): 1520-1528 (2000).

Wood et al., "Atrophin-1, the DRPLA gene product, interacts with two families of WW domain-containing proteins," *Mol. Cell. Neurosci.*, 11(3):149-160 (1998).

Yan et al., "Exon skipping causes alteration of the COOH-terminus and deletion of the phospholipase C gamma 1 interaction site in the FGF receptor 2 kinase in normal prostate epithelial cells," Biochem. Biophys. Res. Commun., 194(1): 512-518 (1993).

Yan et al., "Molecular cloning of mouse ERK5/BMK1 splice variants and characterization of ERK5 functional domains," *J. Biol. Chem.*, 276(14);10870-10878 (2001).

Yang et al., "Interaction of mycoyte enhancer factor 2 (MEF2) with a mitogen-activated protein kinase, ERK5/BMK1," *Nucleic Acids Res.*, 26(20): 4771-4777 (1998).

Yoshida et al., "Biochemical evidence for association of dystrobrevin with the sarcoglycan-sarcospan complex as a basis for understanding sarcoblycanopathy," Hum. Mol. Genet., 9(7):1033-1040 (2000).

Young et al., "Isolation and characterization of a new cellular oncogene encoding a protein with multiple potential transmembrane domains," *Cell*, 45(5):711-710 (1986).

Zhang et al., "Purification, characterization, and cDNA cloning of an AU-rich element RNA-binding protein, AUF1," *Mol. Cell. Biol.*, 13(12):7652-7665 (1993).

Zhou et al., "Components of a new human protein kinase signal transduction pathway," *J. Biol. Chem.*, 270(21):12665-12669 (1995).

Bennett et al., "A Distinct Subgroup of Small DRG Cells Express GDNF Receptor Components and GDNF Is Protective for These Neurons after Nerve Injury," *J. Neuroscience*, 18:3059-3072 (1998).

Boucher et al. "Potent Analgesic Effects of GDNF in Neuropathic Pain States," *Science*, 290:124-127 (2000).

Petruska et al. "Subclassified acutely dissociated cells of rat DRG: histochemistry and patterns of capsaicin-, proton-, and ATP-activated currents," *J. Neurophysiology*, 84:2365-2379 (2000).

Vulchanova et al. "Cytotoxic targeting of isolectin IB4-binding sensory neurons," *Neuroscience*, abstract, 108:143-155 (2001).

Walker, Astra Zeneca presentation at IBC G-protein coupled receptor conference. San Diego, CA, Oct. 14-16, 2002.

\* cited by examiner

```
mrg3     LCPIWYHCHRPEHTSTVMCAVIWVLSLLICILNSYFCGELNTQYKNENGCLALNEFTAAYLMFLFVVLCLSSLALVA
mrg4     LCPIWYHCHRPEHTSTVMCAAIWVLSLLICILNSYFCGVLHTRYDNDNGCLATNIFTASYMIFLLVVLCLSSLALLA
mrg5     LCPIWYHCHRRPEHTSTVMCAVIWVLSLLICILDGYFCGYLDNHYFNYSVCQAWDIFIGAYPMLFVVLCLSTLALLA
mrg6     LCPIWYHCRRPEHTSTVMCAVIWVLSLLICILNSYFCGFLNTQYKNENGCLALSFFTAAYLMFLFVVLCLSSLALVA
mrg7     LCPTWYRCHRPVHTSTVMCAVIWVLSLLICILNSYFCAVLHTRYDNDNECLATNIFTASYMIFLLVVLCLSSLALLA
mrg8     LCPIWYRCHRPEHTSTIMCVVIWVLSLLICLLNRYFCDLFGPKYEINSVCQASEFFIRIYPIFLFVVLCFSTLTLLA
Human1   LWPIWYRCHRPTHLSAVVCVLLWALSLLRSILEWMLCGFLESGA-DSAWCQTSDFITVAWLIFLCVVLFCVVLLI
Human2   LWPIWYRCRRPRHLSAVVCVLLWALSLLLSILEGKFCGFLFSDG-DSGWCQTFDFITAAWLIFLFMVLCGSSLALLV mrg3     RLFCGTGQIKLTRLYVTIMLSIIVFLLCGLPFGIHWFLLFLLFKIKDDFHVFDLGFYLASVVLTAINSCANPIIYFFVG
mrg4     RLFCGAGQMKAYQFHVTLLTLLMTVLVFLLCGLPIAIYCFLLEKIKGDFHVLDVNLYLALEVLTAINSCANPIIYFFVG
mrg5     RLFCGARNMKFTRLFVTIMLFVTIMLTVLVFLLCGLPWGITWFLLFWLLFKIKGDFHVLDVNLYLALEVPDYSPLL---VLTAINSCANPIIYFFVG
mrg6     RLFCGARNMKFTRLFVTIMLTVLVFLLCGLPWGITWFLLFWLLFKIKGDFHVLDVNLYLALEVPDYSPLL---VLTAINSCANPIIYFFVG
mrg7     RLFCGAGQMKLTRFHVTILLTLLFMTILVFLLCGLPFFVIYCILLFKIKDDFHVLDVNLYLALEVLTAINSCANPIIYFFVG
mrg8     RLFCGAGKKKFTRLEMTIMVTILVFLLCGLPFGFLMWLLPWIEGGFSILDYRFFLASLVLTAINSCANPIIYFFVG
human1   RILCGSRKIPLTRLYLTILLTVLVFLLCGLPFGIQFFLEWIHVDREVLFCHVHLVSIFLSALNSSANPIIYFFVG
human2   RILCGSRGIPLTRLYLTILLLTVIVFLLCGLPFGIQWFLILWMIWKDSDVLFCHIHPVSVVLSSLNSSANPIIYFFVG
```

FIG. 1A

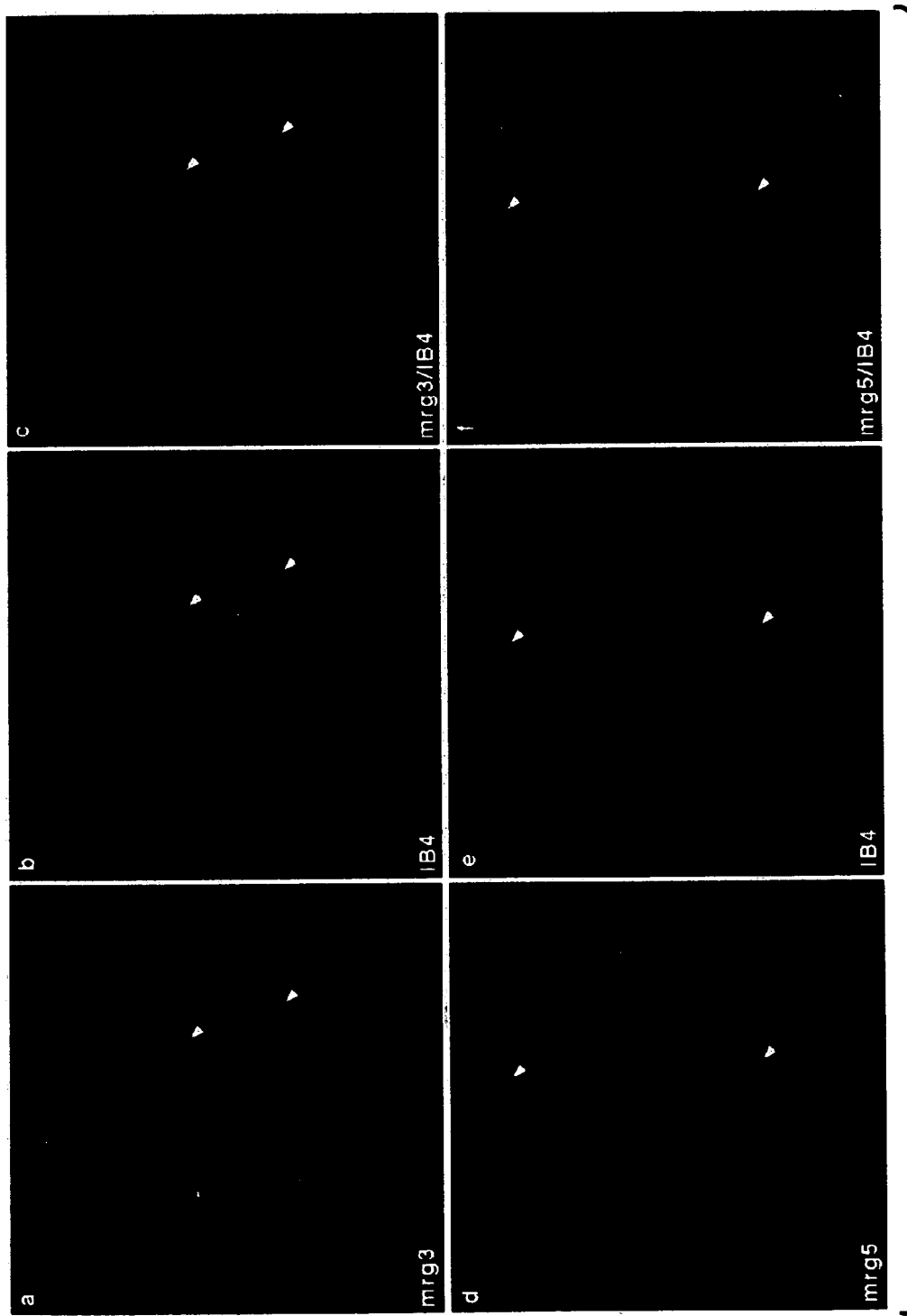

MRG POLYPEPTIDES AND NUCLEIC ACIDS ENCODING THE SAME

CROSS-REFERENCES TO RELATED APPLICATIONS

This application claims priority under 35 U.S.C. § 119(e) to Provisional Applications 60/202,027, entitled: Isolation of Signaling Molecules Involved in Pain Sensation, filed May 4, 2000, and 60/222,344, entitled: Pain Signaling Molecules, filed Aug. 1, 2000, which are herein incorporated by reference in their entirety.

FIELD OF THE INVENTION

The invention relates generally to novel genes expressed in normal but not neurogenin-1-deficient animals. The invention relates specifically to a novel family of G protein-coupled receptors and a novel family of two-transmembrane segment proteins that are expressed in dorsal root ganglia, and a method of screening for genes specifically expressed in nociceptive sensory neurons.

BACKGROUND OF THE INVENTION

The treatment of acute and chronic intractable pain is a major target of drug development in the pharmaceutical industry. Pain sensation is mediated by primary sensory neurons in the dorsal root ganglia (DRG), which project peripherally to the skin and centrally to the spinal cord. These neurons express signaling molecules, such as receptors, ion channels and neuropeptides, which are involved in pain sensation. One example is the so-called Vanillinoid Receptor-1 (VR-1), which is activated by capsaicin (chili pepper) as well as by heat and acid. Such pain signaling molecules may also influence pain sensation indirectly by acting as positive or negative modulators of the sensory pathway. Searching for drugs that interact with such signaling molecules, for example as receptor agonists or antagonists, is an important approach to the discovery of new therapeutics for the treatment of pain. New candidate signaling molecules expressed by pain-sensing ("nociceptive") sensory neurons are therefore highly desirable targets for new drug screening and drug discovery efforts.

The present inventors have previously identified a novel family of basic helix loop-helix (bHLH) transcription factors, called the Neurogenins (Ngns), which are essential for the development of sensory neurons in the DRG. Different Ngns are required for the development of different subsets of sensory neurons. In particular, Ngn1 is necessary for the development of most if not all nociceptive sensory neurons. In Ngn1$^{-/-}$ mutant mice, although DRG are still present, they are reduced in size and the majority of nociceptive neurons, identified by expression of markers such as trkA and VR-1, are missing (Ma et al., Genes Develop, 13; 1717-1728, 1999). These results suggested that the isolation of genes expressed in wild-type (normal) but not Ngn1$^{-/-}$ DRG might lead to the identification of novel drug target molecules expressed in differentiating or mature nociceptive sensory neurons.

SUMMARY OF THE INVENTION

The present inventors have carried out such a screen using positive selection based differential hybridization. This screen has identified both known signaling molecules involved in nociceptive neuron function, such as VR-1, and novel signaling molecules that are highly specifically expressed in nociceptive sensory neurons. The present invention therefore includes the discovery of new genes that are expressed in normal mice but not in Ngn1 null mutant mice. One family of novel genes isolated from the screen encodes a receptor protein with 7 transmembrane segments, mrg, a characteristic of G protein-coupled receptors. Subsequent staining experiments (see FIG. 2, 2A-D) confirmed that mrg genes were expressed specifically in subsets of nociceptive neurons in DRG. Another novel gene family isolated in this screen, drg-12, encodes a protein with two transmembrane segments.

In particular, the invention includes isolated nucleic acid molecules that encode a mrg protein selected from the group consisting of an isolated nucleic acid molecule that encodes the amino acid sequence of SEQ ID NOS: 2, 4, 6, 8, 10, 12, 16, 18, 21, 23, 25, 27, an isolated nucleic acid molecule that encodes a fragment of at least 6 amino acids of SEQ ID NOS: 2, 4, 6, 8, 10, 12, 16, 18, 21, 23, 25, 27, an isolated nucleic acid molecule which hybridizes to the complement of a nucleic acid molecule comprising SEQ ID NOS: 1, 3, 5, 7, 9, 11, 15, 17, 20, 22, 24 or 26 and an isolated nucleic acid molecule which hybridizes to the complement of a nucleic acid molecule that encodes the amino acid sequence of SEQ ID NOS: 2, 4, 6, 8, 10, 12, 16, 18, 21, 23, 25 or 27. Nucleic acid molecules of the invention also include those that encode a protein that is expressed in dorsal root ganglia and have at least about 60% nucleotide sequence identity, preferably at least about 70-75% sequence identity, more preferably at least about 80-85% sequence identity, and even more preferably at least about 90% sequence identity through the coding sequences of SEQ ID NOS: 1, 3, 5, 7, 9, 11, 15, 17, 20, 22, 24 or 26. Alternatively, nucleic acid molecules of the invention may encode a mrg protein that exhibits at least about 38% amino acid sequence identity with SEQ ID NOS: 2, 4, 6, 8, 10, 12, 16, 18, 21, 23, 25 or 27.

The invention also includes isolated nucleic acid molecules that encode a drg-12 protein selected from the group consisting of an isolated nucleic acid molecule that encodes the amino acid sequence of SEQ ID NOS: 14, 19 or 29 an isolated nucleic acid molecule that encodes a fragment of at least 6 amino acids of SEQ ID NOS: 14, 19 or 29, an isolated nucleic acid molecule which hybridizes to the complement of a nucleic acid molecule comprising SEQ ID NO: 13 or 28 and an isolated nucleic acid molecule which hybridizes to the complement of a nucleic acid molecule that encodes the amino acid sequence of SEQ ID NOS: 14, 19 or 29. Nucleic acid molecules of the invention also include those that encode a drg-12 protein that is expressed in dorsal root ganglia and have at least about 60% nucleotide sequence identity, preferably at least about 70-75% sequence identity, more preferably at least about 80-85% sequence identity, and even more preferably at least about 90% sequence identity through the coding sequence of SEQ ID NO: 13 or 28. Alternatively, nucleic acid molecules of the invention may encode a drg-12 protein that exhibits at least about 33% amino acid sequence identity with SEQ ID NOS: 14, 19 or 29.

The present invention also includes the nucleic acid molecules described above operably linked to one or more expression control elements, including vectors comprising the isolated nucleic acid molecules. The invention further includes host cells transformed to contain the nucleic acid molecules of the invention and methods for producing a protein comprising the step of culturing a host cell transformed with a nucleic acid molecule of the invention under conditions in which the protein is expressed.

The invention further provides an isolated Mrg polypeptide selected from the group consisting of an isolated polypeptide comprising the amino acid sequence of SEQ ID NOS: 2, 4, 6, 8, 10, 12, 16, 18, 21, 23, 25 or 27, an isolated polypeptide comprising a functional fragment of at least 10 amino acids of SEQ ID NOS: 2, 4, 6, 8, 10, 12, 16, 18, 21, 23, 25 or 27, an isolated polypeptide comprising conservative amino acid substitutions of SEQ ID NOS: 2, 4, 6, 8, 10, 12, 16, 18, 21, 23, 25 or 27 and naturally occurring amino acid sequence variants of SEQ ID NOS: 2, 4, 6, 8, 10, 12, 16, 18, 21, 23, or 27. Polypeptides of the invention also include polypeptides with an amino acid sequence having at least about 38%, 40%, 50%, 60%, 70% or 75% amino acid sequence identity with the sequence set forth in SEQ ID NO: 2, 4, 6, 8, 10, 12, 16, 18, 21, 23, 25 or 27 more preferably at least about 80%, even more preferably at least about 90%, and most preferably at least about 95% sequence identity with these sequences.

The invention further provides an isolated Drg-12 polypeptide selected from the group consisting of an isolated polypeptide comprising the amino acid sequence of SEQ ID NOS: 14, 19 or 29, an isolated polypeptide comprising a functional fragment of at least 10 amino acids of SEQ ID NOS: 14, 19 or 29 an isolated polypeptide comprising conservative amino acid substitutions of SEQ ID NOS: 14, 19 or 29 and naturally occurring amino acid sequence variants of SEQ ID NOS: 14, 19 or 29. Polypeptides of the invention also include polypeptides with an amino acid sequence having at least about 33%, 35%, 40%, 50%, 60%, 70% or 75% amino acid sequence identity with the sequence set forth in SEQ ID NO: 14, 19 or 29, more preferably at least about 80%, even more preferably at least about 90%, and most preferably at least about 95% sequence identity with these sequences.

The invention further provides an isolated antibody that specifically binds to a polypeptide of the invention, including monoclonal and polyclonal antibodies.

The invention further provides methods of identifying an agent which modulates the expression of a nucleic acid encoding a protein of the invention, comprising the steps of: exposing cells which express the nucleic acid to the agent; and determining whether the agent modulates expression of said nucleic acid, thereby identifying an agent which modulates the expression of a nucleic acid encoding the protein.

The invention further provides methods of identifying an agent which modulates at least one activity of a protein of the invention, comprising the steps of: exposing cells which express the protein to the agent; and determining whether the agent modulates at least one activity of said protein, thereby identifying an agent which modulates at least one activity of the protein.

The invention further provides methods of identifying binding partners for a protein of the invention, comprising the steps of: exposing said protein to a potential binding partner; and determining if the potential binding partner binds to said protein, thereby identifying binding partners for the protein.

The present invention further provides methods of modulating the expression of a nucleic acid encoding a protein of the invention, comprising the step of: administering an effective amount of an agent which modulates the expression of a nucleic acid encoding the protein. The invention also provides methods of modulating at least one activity of a protein of the invention, comprising the step of: administering an effective amount of an agent which modulates at least one activity of the protein.

The present invention further includes non-human transgenic animals modified to contain the nucleic acid molecules of the invention or mutated nucleic acid molecules such that expression of the polypeptides of the invention is prevented.

The invention further provides methods of pain treatment, comprising the steps of: administering to a patient in need thereof a therapeutically effective amount of an agent that modulates the production or at least one activity of a polypeptide or nucleic acid of the invention.

In another aspect the invention provides a method of identifying candidate genes involved in nociception comprising the steps of: generating a first set of non-human animals that is Ngn1−/− and a second set of non-human animals that is wild-type for the Ngn1 gene; isolating RNA from the dorsal root ganglia of the first and second set of animals; enriching for genes expressed in the DRG wild-type but not in the Ngn1 mutant animals; and further characterizing and selecting for candidate genes using methods such as sequencing, degenerated RT-PCR and in situ hybridization.

BRIEF DESCRIPTION OF THE DRAWINGS

FIG. 1A shows the alignment of a homologous region of the amino acid sequences of SEQ ID NO: 2, 4, 6, 8, 10 and 12, and also of the two human members of the mrg family (SEQ ID NOS: 16 and 18).

FIG. 2D. mrgs are expressed by IB4+ nociceptive neurons. Double labeling technique was used to colocalize IB4 (green; [b,e]) and mrgs (red; [a,d]) in DRG neurons. The expressions of mrg3 and mrg5 were visualized by in situ hybridization as described before. The same DRG sections were subsequently undergone through FITC-conjugated lectin IB4 binding. In the merged images (c,f), there are extensive overlappings between mrgs and IB4 stainings (yellow neurons indicated by arrowheads).

DETAILED DESCRIPTION OF THE PREFERRED EMBODIMENT

I. General Description

Figure 1B:
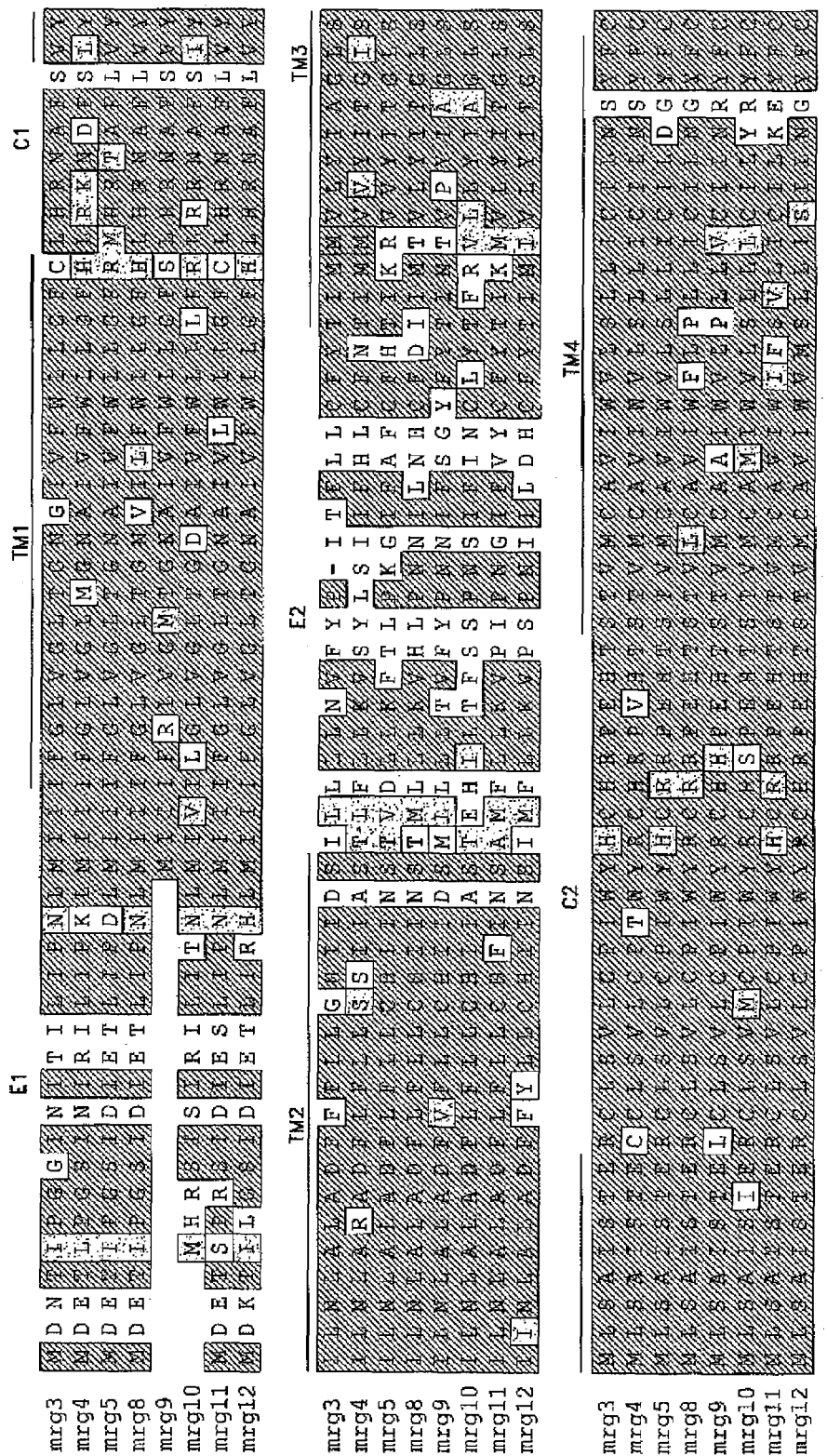
FIGS. 1B-D. mrgs Define a Novel G protein-couple receptor Gene Family. Amino acid sequences of eight mouse full-length mrg genes were aligned using ClustalW. The sequences depicted are: mrg3 (SEQ ID NO: 2), mrg4 (SEQ ID NO: 4), mrg5 (SEQ ID NO: 6), mrg8 (SEQ ID NO: 12), mrg9 (SEQ ID NO: 21), mrg10 (SEQ ID NO: 23), mrg 11 (SEQ ID NO: 25), and mrg12 (SEQ ID NO: 27). Identical residues in >50% of the predicted proteins are darkly shaded; conservative substitutions are highlighted in light gray. The approximate locations of predicted transmembrane domain 1-7 are indicated on top of the sequences as TM1-TM7. The predicted extracellular and cytoplasmic domains are indicated as E1-E7 and C1-C7 respectively.

As described above, the present invention is based on the discovery of new genes that are expressed in the DRG of normal mice but not in Ngn1 null mutant mice. One of the novel gene families isolated from the screen encodes a receptor protein with 7 transmembrane segments, a characteristic of G protein-coupled receptors. This novel 7 transmembrane receptor is most closely related to the oncogene mas, and therefore was provisionally named mas-related gene-3 (mrg3). G protein-coupled receptors are also expressed in other classes of sensory neurons, such as olfactory and gustatory neurons, but molecules in this class had not previously been described in DRG sensory neurons, with the exception of the Protease-Activated Receptors (PARs).

The existence of a family of putative G protein-coupled receptors specifically expressed in nociceptive sensory neurons suggests that these molecules are primary mediators or modulators of pain sensation. It will therefore be of great interest to identify ligands, both endogenous and synthetic, that modulate the activity of these receptors, for the management of chronic intractable pain.

Another novel gene family isolated in this screen, drg-12 encodes a protein with two putative transmembrane segments. In situ hybridization indicates that, like the mrg genes, this gene is also specifically expressed in a subset of DRG sensory neurons. As it is a membrane protein it may also be involved in signaling by these neurons. Although there are no obvious homologies between this protein and other known proteins, it is noteworthy that two purinergic receptors specifically expressed in nociceptive sensory neurons ($P_2X_2$ and $P_2X_3$) have a similar bipartite transmembrane topology. Therefore it is likely that the family drg-12 also encodes a receptor or ion channel involved in nociceptive sensory transduction or its modulation.

The proteins of the invention can serve as a target for agents that modulate their expression or activity, for example in chronic intractable pain. For example, agents may be identified which modulate biological processes associated with nociception such as the reception, transduction and transmission of pain signals.

II. Specific Embodiments

A. Proteins Expressed in Primary Sensory Neurons of Dorsal Root Ganglia

The present invention provides isolated mrg and drg-12 proteins, allelic variants of the proteins, and conservative amino acid substitutions of the proteins. As used herein, the "protein" or "polypeptide" refers, in part, to a protein that has the amino acid sequence depicted in SEQ ID NO: 2, 4, 6, 8, 10, 12, 14, 16, 18, 19, 21, 23, 25, 27 or 29. The terms also refer to naturally occurring allelic variants and proteins that have a slightly different amino acid sequence than those specifically recited above. Allelic variants, though possessing a slightly different amino acid sequence than those recited above, will still have the same or similar biological functions associated with the protein.

As used herein, the "family of proteins" related to the amino acid sequences of SEQ ID NO: 2, 4, 6, 8, 10, 12, 14, 16, 18, 19, 21, 23, 25, 27 or 29 includes proteins that have been isolated from the dorsal root ganglia of organisms in addition to mice and humans. The methods used to identify and isolate other members of the family of proteins related to these proteins, such as the disclosed mouse and human proteins, are described below.

The proteins of the present invention are preferably in isolated form. As used herein, a protein is said to be isolated when physical, mechanical or chemical methods are employed to remove the protein from cellular constituents that are normally associated with the protein. A skilled artisan can readily employ standard purification methods to obtain an isolated protein. In some instances, isolated proteins of the invention will have been separated or purified from many cellular constituents, but will still be associated with cellular membrane fragments or membrane constituents.

The proteins of the present invention further include insertion, deletion or conservative amino acid substitution variants of the sequences set forth in SEQ ID NO: 2, 4, 6, 8, 10, 12, 14, 16, 18, 19, 21, 23, 25, 27 or 29. As used herein, a conservative variant refers to alterations in the amino acid sequence that do not adversely affect the biological functions of the protein. A substitution, insertion or deletion is said to adversely affect the protein when the altered sequence prevents or disrupts a biological function associated with the protein. For example, the overall charge, structure or hydrophobic/hydrophilic properties of the protein can be altered without adversely affecting a biological activity. Accordingly, the amino acid sequence can be altered, for example to render the peptide more hydrophobic or hydrophilic, without adversely affecting the biological activities of the protein.

Ordinarily, the allelic variants, the conservative substitution variants, and the members of the protein family, will have an amino acid sequence having at least about 50%, or about 60% to 75% amino acid sequence identity with the sequences set forth in SEQ ID NO: 2, 4, 6, 8, 10, 12, 14, 16, 18, 19, 21, 23, 25, 27 or 29, more preferably at least about 80%, even more preferably at least about 90%, and most preferably at least about 95% sequence identity with said sequences. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity (see section B for the relevant parameters). Fusion proteins, or N-terminal, C-terminal or internal extensions, deletions, or insertions into the peptide sequence shall not be construed as affecting homology.

Thus, the proteins of the present invention include molecules having the amino acid sequence disclosed in SEQ ID NO: 2, 4, 6, 8, 10, 12, 14, 16, 18, 19, 21, 23, 25, 27, 29; fragments thereof having a consecutive sequence of at least about 3, 4, 5, 6, 10, 15, 20, 25, 30, 35 or more amino acid residues of the protein; amino acid sequence variants wherein one or more amino acid residues has been inserted N- or C-terminal to, or within, the disclosed coding sequence; and amino acid sequence variants of the disclosed sequence, or their fragments as defined above, that have been substituted by another residue. Such fragments, also referred to as peptides or polypeptides, may contain antigenic regions, functional regions of the protein identified as regions of the amino acid sequence which correspond to known protein domains, as well as regions of pronounced hydrophilicity. The regions are all easily identifiable by using commonly available protein sequence analysis software such as MacVector™ (Oxford Molecular).

Contemplated variants further include those containing predetermined mutations by, e.g., homologous recombination, site-directed or PCR mutagenesis, and the corresponding proteins of other animal species, including but not limited to rabbit, rat, porcine, bovine, ovine, equine, human and non-human primate species, and the alleles or other naturally occurring variants of the family of proteins; and derivatives wherein the protein has been covalently modified by substitution, chemical, enzymatic, or other appropriate means with a moiety other than a naturally occurring amino acid (for example a detectable moiety such as an enzyme or radioisotope).

Protein domains such as a ligand binding domain, an extracellular domain, a transmembrane domain (e.g. comprising seven membrane spanning segments and cytosolic loops or two membrane spanning domains and cystosolic loops), the transmembrane domain and a cytoplasmic domain and an active site may all be found in the proteins or polypeptides of the invention. Such domains are useful for making chimeric proteins and for in vitro assays of the invention.

As described below, members of the family of proteins can be used: 1) to identify agents which modulate at least one activity of the protein; 2) to identify binding partners for the protein, 3) as an antigen to raise polyclonal or monoclonal antibodies, 4) as a therapeutic target, 5) as diagnostic markers to specific populations of pain sensing neurons and 6) as targets for structure based ligand identification.

B. Nucleic Acid Molecules

The present invention further provides nucleic acid molecules that encode the mrg or drg-12 proteins having SEQ ID NO: 2, 4, 6, 8, 10, 12, 14, 16, 18, 19, 21, 23, 25, 27 or 29 and the related polypeptides herein described, preferably in isolated form. As used herein, "nucleic acid" is defined as RNA or DNA that encodes a protein or peptide as defined above, is complementary to a nucleic acid sequence encoding such peptides, hybridizes to such a nucleic acid and remains stably bound to it under appropriate stringency conditions, exhibits at least about 50%, 60%, 70%, 75%, 85%, 90% or 95% nucleotide sequence identity across the open reading frame, or encodes a polypeptide sharing at least about 50%, 60%, 70% or 75% sequence identity, preferably at least about 80%, and more preferably at least about 85%, and even more preferably at least about 90 or 95% or more identity with the peptide sequences. Specifically contemplated are genomic DNA, cDNA, mRNA and antisense molecules, as well as nucleic acids based on alternative backbones or including alternative bases whether derived from natural sources or synthesized. Such hybridizing or complementary nucleic acids, however, are defined further as being novel and unobvious over any prior art nucleic acid including that which encodes, hybridizes under appropriate stringency conditions, or is complementary to nucleic acid encoding a protein according to the present invention.

Homology or identity at the nucleotide or amino acid sequence level is determined by BLAST (Basic Local Alignment Search Tool) analysis using the algorithm employed by the programs blastp, blastn, blastx, tblastn and tblastx (Karlin, et al. Proc. Natl. Acad. Sci. USA 87: 2264-2268 (1990) and Altschul, S. F. J. Mol. Evol. 36: 290-300 (1993), fully incorporated by reference) which are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al. (Nature Genetics 6: 119-129 (1994)) which is fully incorporated by reference. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff, et al. Proc. Natl. Acad. Sci. USA 89: 10915-10919 (1992), fully incorporated by reference). For blastn, the scoring matrix is set by the ratios of M (i.e., the reward score for a pair of matching residues) to N (i.e., the penalty score for mismatching residues), wherein the default values for M and N are 5 and -4, respectively. Four blastn parameters were adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

"Stringent conditions" are those that (1) employ low ionic strength and high temperature for washing, for example, 0.015 M NaCl/0.0015 M sodium citrate/0.1% SDS at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS. A skilled artisan can readily determine and vary the stringency conditions appropriately to obtain a clear and detectable hybridization signal. Preferred molecules are those that hybridize under the above conditions to the complement of SEQ ID NO: 1, 3, 5, 7, 9, 11, 13, 15, 17, 20, 22, 24, 26 or 28 and which encode a functional peptide. Preferred hybridizing molecules are those that hybridize under the above conditions to the complement strand of the open reading frame or coding sequences of SEQ ID NOS: 1, 3, 5, 7, 9, 11, 13, 15, 17, 20, 22, 24, 26 or 28.

As used herein, a nucleic acid molecule is said to be "isolated" when the nucleic acid molecule is substantially separated from contaminant nucleic acid molecules encoding other polypeptides.

Figure 3A:
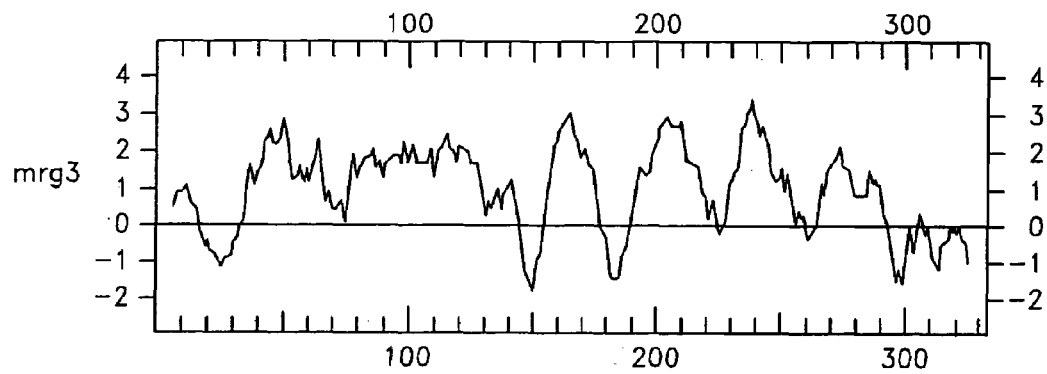
FIG. 3 compares the hydrophobicity plots predicting the transmembrane regions of the amino acid sequence of (A) mrg3 (SEQ ID NO: 2); (B) human1 gene (SEQ ID NO: 15); and (C) human2 gene (SEQ ID NO: 17). More positive values indicate hydrophobicity.
Figure 3B:
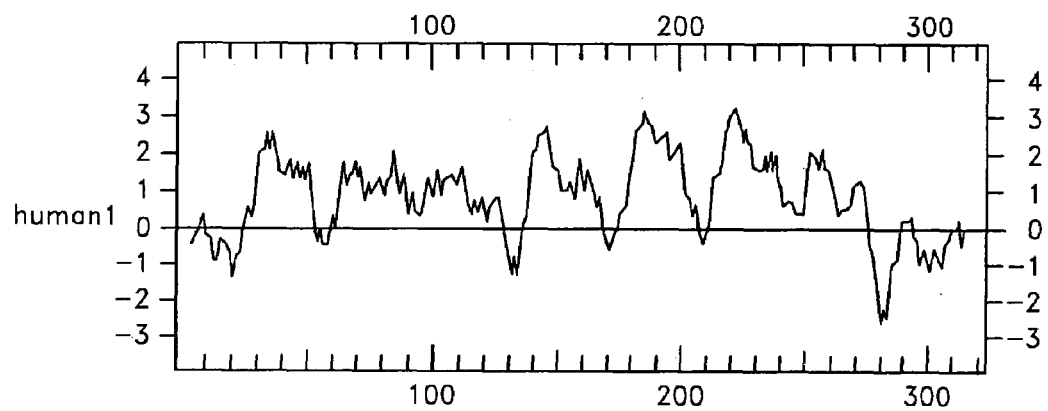
Figure 3C:
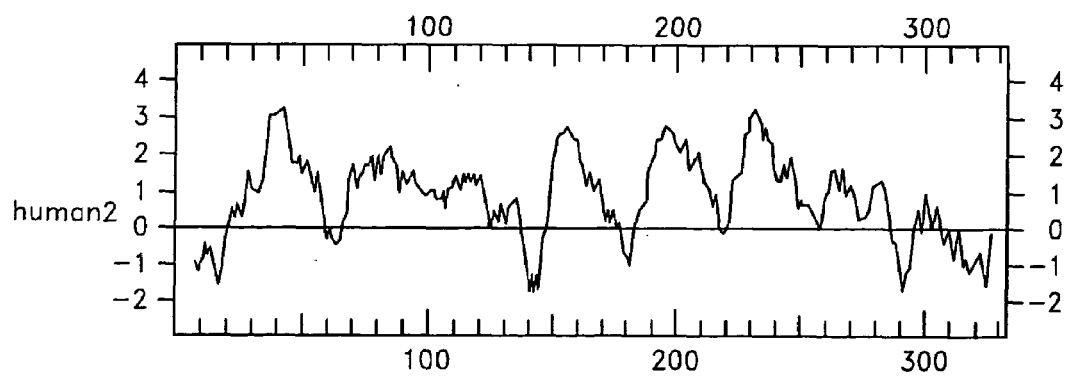
Figure 4A:
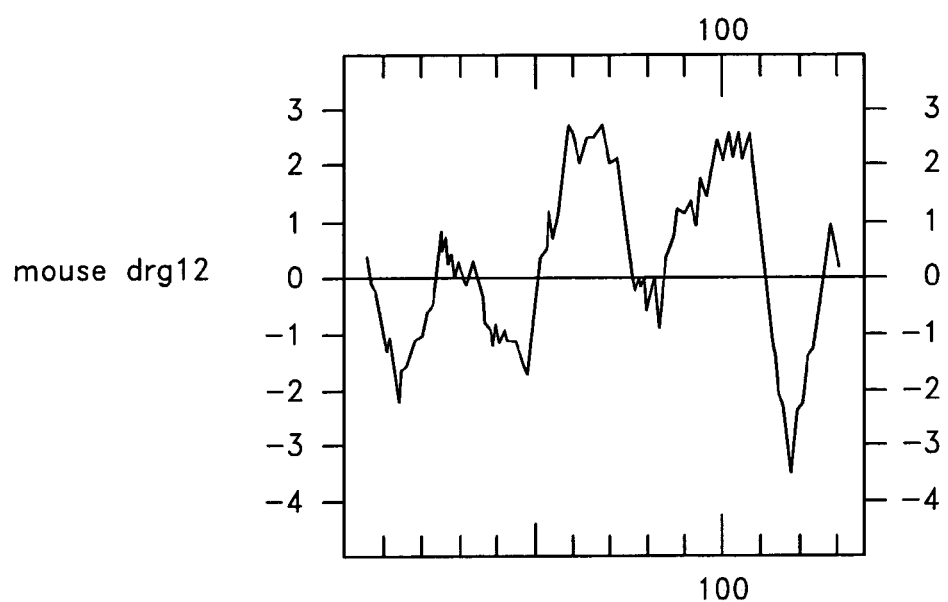
FIG. 4 compares the hydrophobicity plots predicting the transmembrane regions of the amino acid sequence of (A) mouse drg12 (SEQ ID NO: 14); (B) human drg12 (SEQ ID NO: 19)
Figure 4B:
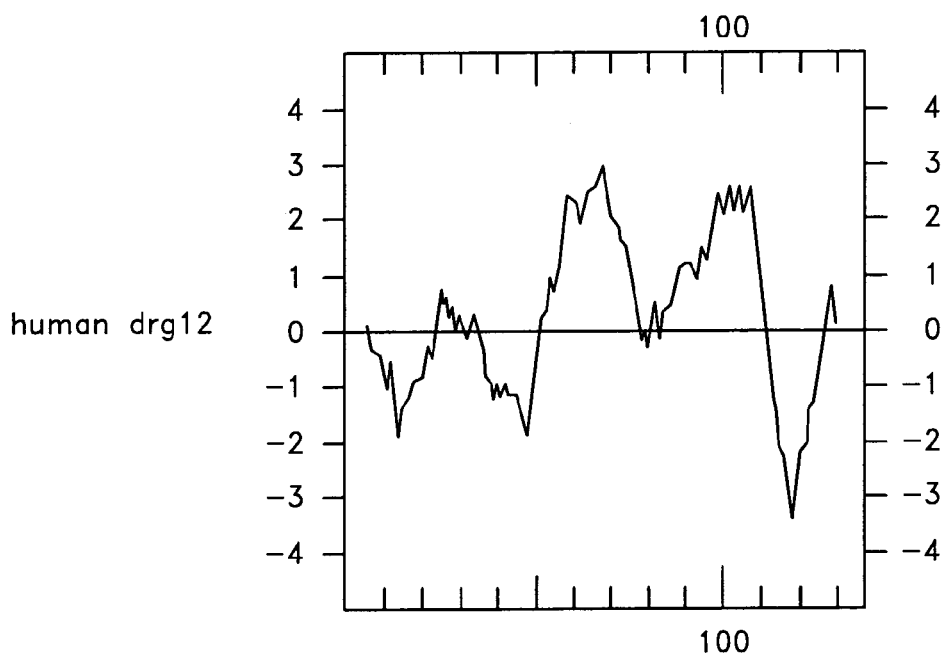
Figure 5:
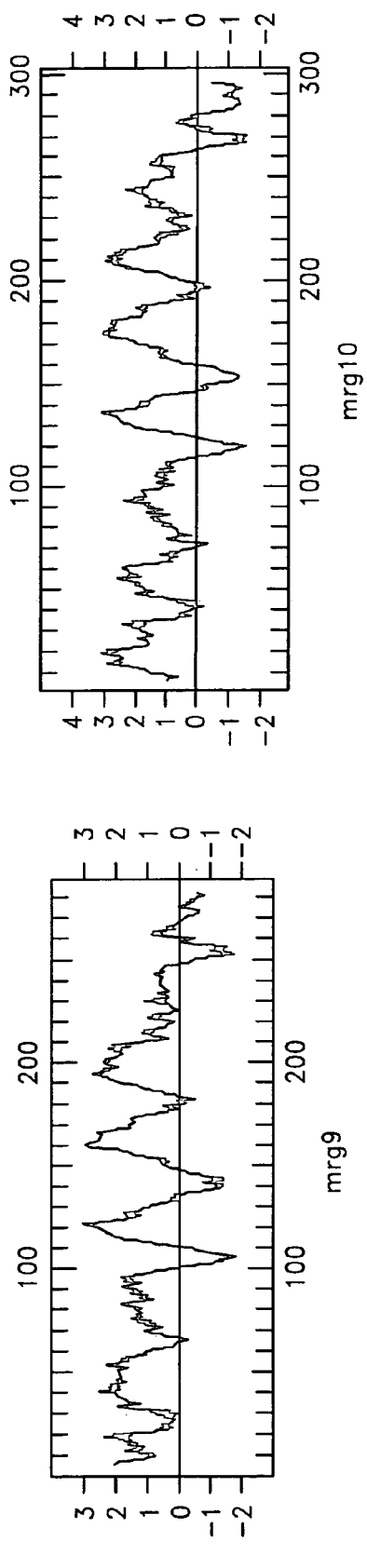
FIG. 5 compares the hydrophobicity plots predicting the transmembrane regions of the amino acid sequence of mrg9 (SEQ ID NO: 21); mrg10 (SEQ ID NO: 23); mrg11 (SEQ ID NO: 25) and mrg12 (SEQ ID NO: 27).
Figure 5:
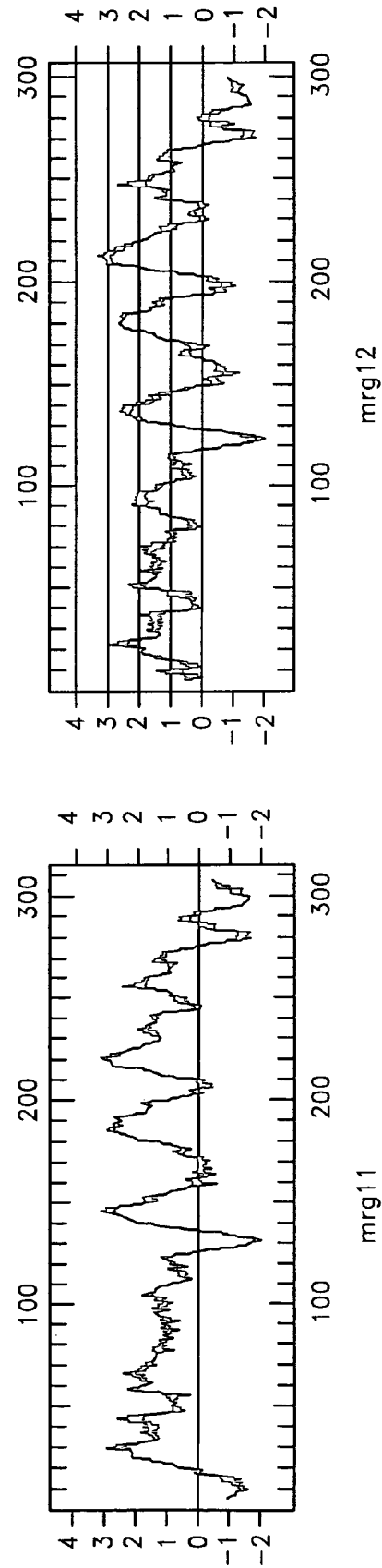

The present invention further provides fragments of the encoding nucleic acid molecule. As used herein, a fragment of an encoding nucleic acid molecule refers to a small portion of the entire protein coding sequence. The size of the fragment will be determined by the intended use. For example, if the fragment is chosen so as to encode an active portion of the protein, the fragment will need to be large enough to encode the functional region(s) of the protein. For instance, fragments which encode peptides corresponding to predicted antigenic regions may be prepared (see FIGS. 3 and 4). If the fragment is to be used as a nucleic acid probe or PCR primer, then the fragment length is chosen so as to obtain a relatively small number of false positives during probing/priming (see the discussion in Section H).

Fragments of the encoding nucleic acid molecules of the present invention (i.e., synthetic oligonucleotides) that are used as probes or specific primers for the polymerase chain reaction (PCR), or to synthesize gene sequences encoding proteins of the invention, can easily be synthesized by chemical techniques, for example, the phosphotriester method of Matteucci, et al., (J. Am. Chem. Soc. 103:3185-3191, 1981) or using automated synthesis methods. In addition, larger DNA segments can readily be prepared by well known methods, such as synthesis of a group of oligonucleotides that define various modular segments of the gene, followed by ligation of oligonucleotides to build the complete modified gene.

The encoding nucleic acid molecules of the present invention may further be modified so as to contain a detectable label for diagnostic and probe purposes. A variety of such labels are known in the art and can readily be employed with the encoding molecules herein described. Suitable labels include, but are not limited to, biotin, radiolabeled nucleotides and the like. A skilled artisan can readily employ any such label to obtain labeled variants of the nucleic acid molecules of the invention.

C. Isolation of Other Related Nucleic Acid Molecules

As described above, the identification and characterization of a nucleic acid molecule encoding a mrg or drg-12 protein allows a skilled artisan to isolate nucleic acid molecules that encode other members of the same protein family in addition to the sequences herein described Essentially, a skilled artisan can readily use the amino acid sequence of SEQ ID NO: 2, 4, 6, 8, 10, 12, 14, 16, 18, 19, 21, 23, 25, 27 or 29 to generate antibody probes to screen expression libraries prepared from appropriate cells. Typically, polyclonal antiserum from mammals such as rabbits immunized with the purified protein (as described below) or monoclonal antibodies can be used to probe a mammalian cDNA or genomic expression library, such as lambda gt11 library prepared from drg-12, to obtain the appropriate coding sequence for other members of the protein family. The cloned cDNA sequence can be expressed as a fusion protein, expressed directly using its own control sequences, or expressed by constructions using control sequences appropriate to the particular host used for expression of the protein.

Alternatively, a portion of the coding sequence herein described can be synthesized and used as a probe to retrieve DNA encoding a member of the protein family from cells derived from any mammalian organism. Oligomers containing approximately 18-20 nucleotides (encoding about a 6-7 amino acid stretch) are prepared and used to screen genomic DNA or cDNA libraries to obtain hybridization under stringent conditions or conditions of sufficient stringency to eliminate an undue level of false positives.

Related nucleic acid molecules may also be retrieved by generating pairs of oligonucleotide primers for use in a polymerase chain reaction (PCR) to selectively clone an encoding nucleic acid molecule. A PCR denature/anneal/extend cycle for using such PCR primers is well known in the art and can readily be adapted for use in isolating other encoding nucleic acid molecules.

Nucleic acid molecules encoding other members of the mrg and drg-12 families may also be identified in existing genomic or other sequence information using any available computational method, including but not limited to: PSI-BLAST (Altschul, et al. (1997) Nucleic Acids Res. 25:3389-3402); PHI-BLAST (Zhang, et al. (1998), Nucleic Acids Res. 26:3986-3990), 3D-PSSM (Kelly et al. (2000) J. Mol. Biol. 299(2): 499-520); and other computational analysis methods (Shi et al. (1999) Biochem. Biophys. Res. Commun. 262(1): 132-8 and Matsunami et. al. (2000) Nature 404(6778):601-4.

D. Recombinant DNA Molecules Containing a Nucleic Acid Molecule

The present invention further provides recombinant DNA molecules (rDNAs) that contain a coding sequence. As used herein, a rDNA molecule is a DNA molecule that has been subjected to molecular manipulation in situ. Methods for generating rDNA molecules are well known in the art, for example, see Sambrook et al., Molecular Cloning: A Laboratory Manual, 2nd edition, 1989; Cold Spring Harbor Laboratory Press, Cold Spring Harbor, N.Y. In the preferred rDNA molecules, a coding DNA sequence is operably linked to expression control sequences and/or vector sequences.

The choice of vector and/or expression control sequences to which one of the protein family encoding sequences of the present invention is operably linked depends directly, as is well known in the art, on the functional properties desired, e.g., protein expression, and the host cell to be transformed. A vector contemplated by the present invention is at least capable of directing the replication or insertion into the host chromosome, and preferably also expression, of the structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as E. coli. A promoter is an expression control element formed by a DNA sequence that permits binding of RNA polymerase and transcription to occur. Promoter sequences that are compatible with bacterial hosts are typically provided in plasmid vectors containing convenient restriction sites for insertion of a DNA segment of the present invention. Typical of such vector plasmids are pUC8, pUC9, pBR322 and pBR329 available from BioRad Laboratories, (Richmond, Calif.), pPL and pKK223 available from Pharmacia (Piscataway, N.J.).

Expression vectors compatible with eukaryotic cells, preferably those compatible with vertebrate cells, can also be used to form rDNA molecules that contain a coding sequence. Eukaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pTDT1 (ATCC, #31255), eukaryotic viral vectors such as adenoviral or retroviral vectors, and the like eukaryotic expression vectors.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene. (Southern et al., J. Mol. Anal. Genet. 1:327-341, 1982.) Alternatively, the selectable marker can be present on a separate plasmid, and the two vectors are introduced by co-transfection of the host cell, and selected by culturing in the appropriate drug for the selectable marker.

E. Host Cells Containing an Exogenously Supplied Coding Nucleic Acid Molecule

The present invention further provides host cells transformed with a nucleic acid molecule that encodes a protein of the present invention. The host cell can be either prokaryotic or eukaryotic but is preferably eukaryotic. Eukaryotic cells useful for expression of a protein of the invention are not limited, so long as the cell line is compatible with cell culture methods and compatible with the propagation of the expression vector and expression of the gene product. Preferred eukaryotic host cells include, but are not limited to, yeast, insect and mammalian cells, preferably vertebrate cells such as those from a mouse, rat, monkey or human cell line. Preferred eukaryotic host cells include Chinese hamster ovary (CHO) cells available from the ATCC as CCL61, NIH Swiss mouse embryo cells (NIH/3T3) available from the ATCC as CRL 1658, baby hamster kidney cells (BHK), HEK293 cells and the like eukaryotic tissue culture cell lines. Xenopus oocytes may also be directly injected with RNA capable of expressing either the mrg or drg-12 proteins by standard procedures (see Tominaga et al. (2000) Jpn J. Pharmacol. 83(1):20-4; Tominaga et al. (1998) Neuron 21(3):531-43 and Bisogno et al. (1999) Biochem, Biophys, Res. Commun. (1999) 262(1):275-84.

Any prokaryotic host can be used to express a rDNA molecule encoding a protein or a protein fragment of the invention. The preferred prokaryotic host is E. coli.

Transformation of appropriate cell hosts with a rDNA molecule of the present invention is accomplished by well known methods that typically depend on the type of vector used and host system employed. With regard to transformation of prokaryotic host cells, electroporation and salt treatment methods are typically employed, see, for example, Cohen et al., Proc. Natl. Acad. Sci. USA 69:2110, 1972; and Maniatis et al., Molecular Cloning, A Laboratory Manual, Cold Spring Harbor Laboratory, Cold Spring Harbor, N.Y. (1982). With regard to transformation of vertebrate cells with vectors containing rDNAs, electroporation, cationic lipid or salt treatment methods are typically employed, see, for example, Graham et al., Virol. 52:456, 1973; Wigler et al., Proc. Natl. Acad. Sci. USA 76:1373-76, 1979.

For transient expression of recombinant channels, transformed host cells for the measurement of $Na^+$ current or intracellular $Na^+$ levels are typically prepared by co-transfecting constructs into cells such as HEK293 cells with a fluorescent reporter plasmid (such as pGreen Lantern-1, Life Technologies) using the calcium-phosphate precipitation technique (Ukomadu et al., (1992) Neuron 8, 663-676). HEK293 cells are typically grown in high glucose DMEM (Life Technologies) supplemented with 10% fetal calf serum (Life Technologies). After forty-eight hours, cells with green fluorescence are selected for recording (Dib-Hajj et al., (1997) FEBS Lett. 416, 11-14).

Successfully transformed cells, i.e., cells that contain a rDNA molecule of the present invention, can be identified by well known techniques including the selection for a selectable marker. For example, cells resulting from the introduction of an rDNA of the present invention can be cloned to produce single colonies. Cells from those colonies can be harvested, lysed and their DNA content examined for the presence of the rDNA using a method such as that described by Southern, J. Mol. Biol. 98:503, 1975, or Berent et al., Biotech. 3:208, 1985 or the proteins produced from the cell assayed via an immunological method F. Production of Recombinant Proteins Using an rDNA Molecule The present invention further provides methods for producing a protein of the invention using nucleic acid molecules herein described. In general terms, the production of a recombinant form of a protein typically involves the following steps:

A nucleic acid molecule is first obtained that encodes a mrg or drg-12 protein of the invention, in particular, nucleotides 34-1026 of SEQ ID NO: 1, nucleotides 34-1029 of SEQ ID NO: 1, nucleotides 137-1051 of SEQ ID NO: 3, nucleotides 137-1054 of SEQ ID NO: 3, nucleotides 84-1070 of SEQ ID NO: 5, nucleotides 84-1073 of SEQ ID NO: 5, nucleotides 1-450 of SEQ ID NO: 7, nucleotides 1-459 of SEQ ID NO: 9, nucleotides 1-459 of SEQ ID NO: 1, nucleotides 170-574 of SEQ ID NO: 13, nucleotides 170-577 of SEQ ID NO: 13, nucleotides 1-966 of SEQ ID NO: 15, nucleotides 1-969 of SEQ ID NO: 15, nucleotides 1-990 of SEQ ID NO: 17, nucleotides 1-993 of SEQ ID NO: 17, nucleotides 83-943 of SEQ ID NO: 20, nucleotides 83-946 of SEQ ID NO:20; nucleotides 16-918 of SEQ ID NO: 22, nucleotides 16-921 of SEQ ID NO: 22; nucleotides 82-1020 of SEQ ID NO: 24, nucleotides 82-1023 of SEQ ID NO: 24; nucleotides 45-959 of SEQ ID NO: 26, nucleotides 45-962 of SEQ ID NO: 26, nucleotides 1-405 of SEQ ID NO: 28 and nucleotides 1-408 of SEQ ID NO: 28. If the encoding sequence is uninterrupted by introns, as are these sequences, it is directly suitable for expression in any host.

The nucleic acid molecule is then preferably placed in operable linkage with suitable control sequences, as described above, to form an expression unit containing the protein open reading frame. The expression unit is used to transform a suitable host and the transformed host is cultured under conditions that allow the production of the recombinant protein. Optionally the recombinant protein is isolated from the medium or from the cells; recovery and purification of the protein may not be necessary in some instances where some impurities may be tolerated or when the recombinant cells are used, for instance, in high throughput assays.

Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with the nucleic acid molecules of the invention to produce recombinant protein.

G. Methods of Using mrgs or drgs as Molecular or Diagnostic Probes

Figure 2:
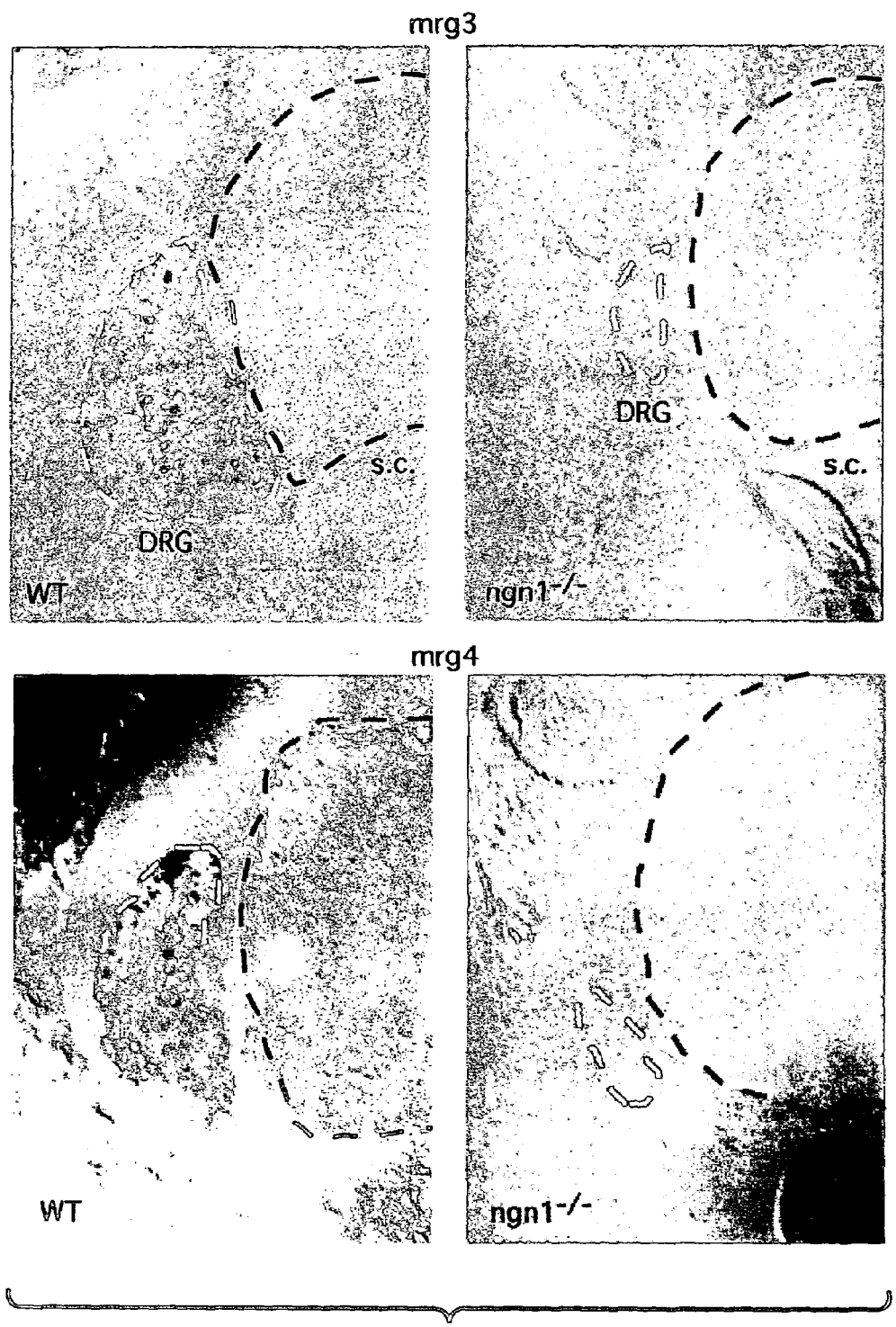
FIG. 2 The microscopy images of in situ hybridization in FIG. 2 show the localization of antisense staining against a nucleotide of SEQ ID NO: 2 ("mrg3") and of SEQ ID NO: 4 ("mrg4") in transverse sections of dorsal root ganglia (DRG) from newborn wild type (WT) and neurogenin1 null mutant (Ngn1$^{-/-}$) mice. White dashed lines outline the DRG and black dashed lines outline the spinal cord. Note that in the Ngn1$^{-/-}$ mutant, the size of the DRG is severely reduced due to the loss of nociceptive sensory neurons, identified using three other independent markers (trkA; VR-1 and SNS-TTXi (Ma et al., (1999)). mrg3 is expressed in a subset of DRG in WT mice (A) but is absent in the Ngn1$^{-/-}$ DRG (B). mrg4 is expressed in a smaller subset of DRG than that of mrg3 (C). It is also absent in the Ngn1$^{-/-}$ DRG (D). The loss of mrg-expressing neurons in the Ngn1$^{-/-}$ DRG indicates that these neurons are likely to be nociceptive.

The sequences and antibodies, proteins and peptides of the present invention may be used as molecular probes for the detection of cells or tissues related to or involved with sensory perception. Although many methods may be used to detect the nucleic acids or proteins of the invention in situ, preferred probes include antisense molecules and anti-mrg or -drg antibodies. For example, the microscopy images of in situ hybridization in FIG. 2 show the localization of antisense staining against a nucleotide of SEQ ID NO:2 ("mrg3") and of SEQ ID NO:4 ("mrg4") in transverse sections of dorsal root ganglia (DRG) from newborn wild type (WT) and neurogenin1 null mutant (Ngn1$^{-/-}$) mice. White dashed lines outline the DRG and black dashed lines outline the spinal cord. Note that in the Ngn1$^{-/-}$ mutant, the size of the DRG is severely reduced due to the loss of nociceptive sensory neurons, identified using three other independent markers (trkA; VR-1 and SNS-TTXi (Ma et al., (1999)). mrg3 is expressed in a subset of DRG in WT mice (A) but is absent in the Ngn1$^{-/-}$ DRG (B). mrg4 is expressed in a smaller subset of DRG than that of mrg3 (C). It is also absent in the Ngn1$^{-/-}$ DRG (D). The loss of mrg-expressing neurons in the Ngn1$^{-/-}$ DRG indicates that these neurons are likely to be nociceptive.

Figure 2A:
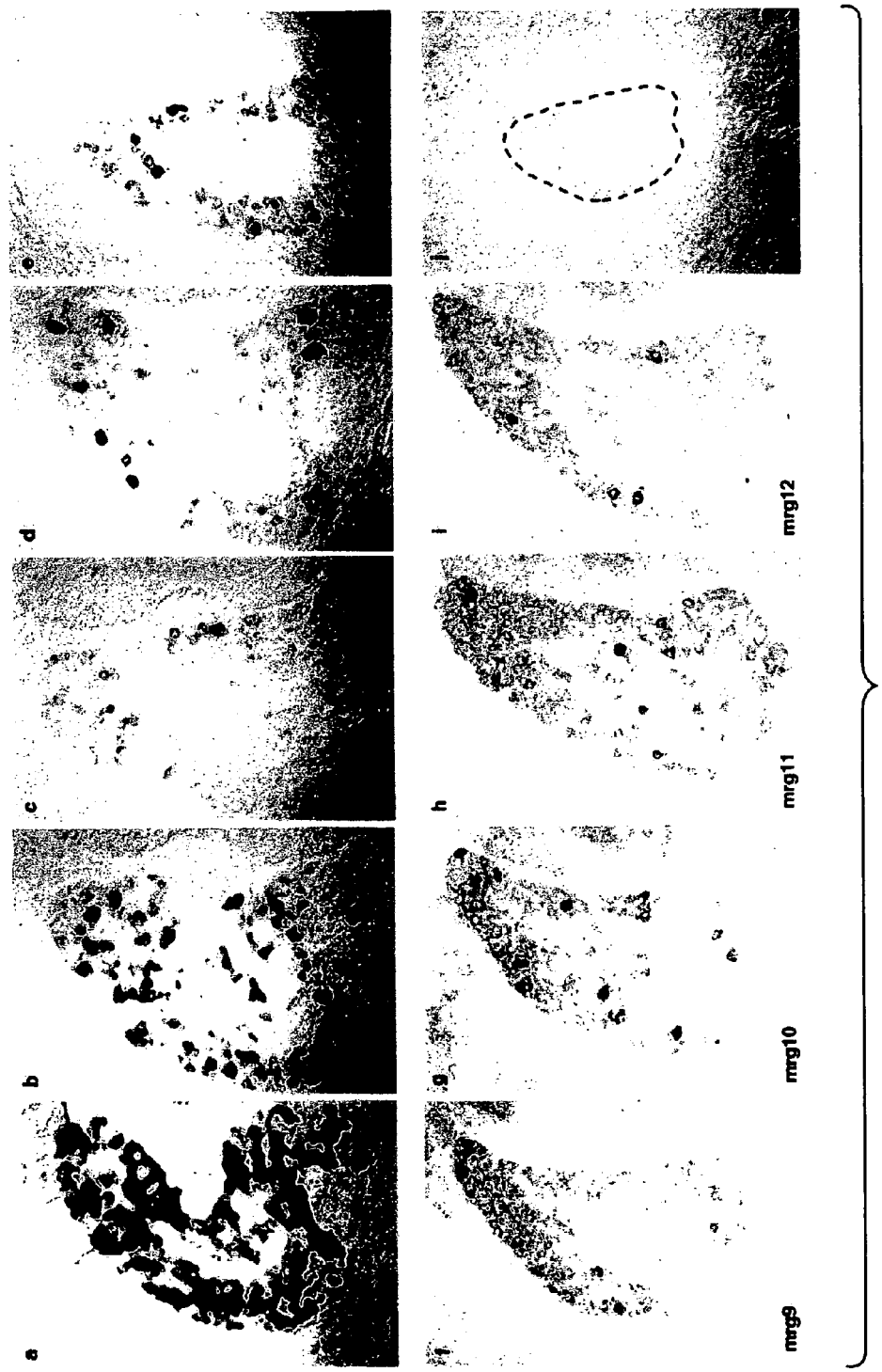
FIG. 2A. Expression of mrgs in subsets of dorsal root ganglia (DRG) neurons. Frozen transverse sections of DRG from wild-type (a-i) and ngn1$^{-/-}$ (j) mutant new born mice were annealed with antisense digoxigenin RNA probes, and hybridization was visualized with an alkailine phosphatase-conjugated antibody. Positive signals are shown as dark purple stainings. TrkA is expressed in a large portion of wild-type DRG neurons (a) but absent in ngn1$^{-/-}$ (data not shown). Each of the eight mrg genes (b-i) is expressed in a small subset of neurons in wild-type DRG in completely absent in ngn1$^{-/-}$ DRG (j and data not shown). Black dash line outlines the ngn1$^{-/-}$ mutant DRG.

Expression of mrgs in subsets of dorsal root ganglia (DRG) neurons are shown in FIG. 2A. Frozen transverse sections of DRG from wild-type (a-i) and ngn1$^{-/-}$ (j) mutant new born mice were annealed with antisense digoxigenin RNA probes, and hybridization was visualized with an alkaline phosphatase-conjugated antibody. Positive signals are shown as dark purple stainings. TrkA is expressed in a large portion of wild-type DRG neurons (a) but absent in ngn1$^{-/-}$ (data not shown). Each of the eight mrg genes (b-i) is expressed in a small subset of neurons in wild-type DRG in completely absent in ngn1$^{-/-}$ DRG 0 and data not shown). Black dash line outlines the ngn1$^{-/-}$ mutant DRG.

Figure 2B:
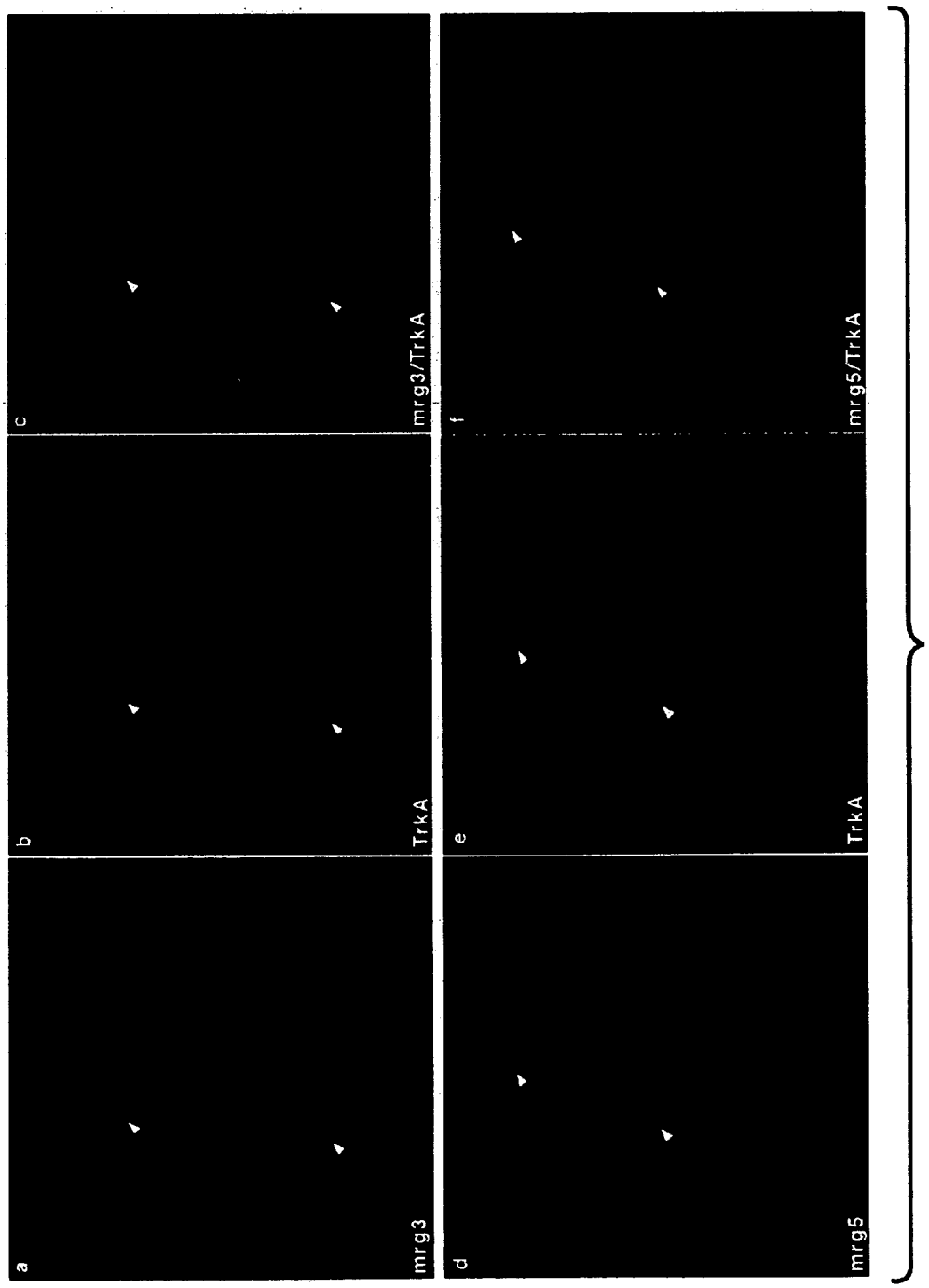
FIG. 2B. mrgs are expressed by TrkA$^+$ nociceptive neurons. Double labeling technique was used to colocalize TrkA (green; [b,e]) and mrgs (red; [a,d]) in DRG neurons. During the double labeling experiments frozen sections of wild-type DRG were undergone in situ hybridizations with either mrg3 (a-c) or mrg5 (d-f) fluorescein-labeled antisense RNA probes followed by anti-TrkA antibody immunostaining. The same two frames (a and b, d and e) were digitally superimposed to reveal the extent of colocalization (c, f). The colocalizations of TrkA with either mrg3 or mrg5 appear yellow in merged images (c, f, respectively). The white arrowheads indicate examples of double positive cells.

In FIG. 2B, mrgs are expressed by TrkA$^+$ nociceptive neurons. Double labeling technique was used to colocalize TrkA (green; [b,e]) and mrgs (red; [a,d]) in DRG neurons. During the double labeling experiments frozen sections of wild-type DRG were undergone in situ hybridizations with either mrg3 (a-c) or mrg5 (d-f) fluorescein-labeled antisense RNA probes followed by anti-TrkA antibody immunostaining. The same two frames (a and b, d and e) were digitally superimposed to reveal the extent of colocalization (c, f). The colocalizations of TrkA with either mrg3 or mrg5 appear yellow in merged images (c, f, respectively). The white arrowheads indicate examples of double positive cells.

Figure 2C:
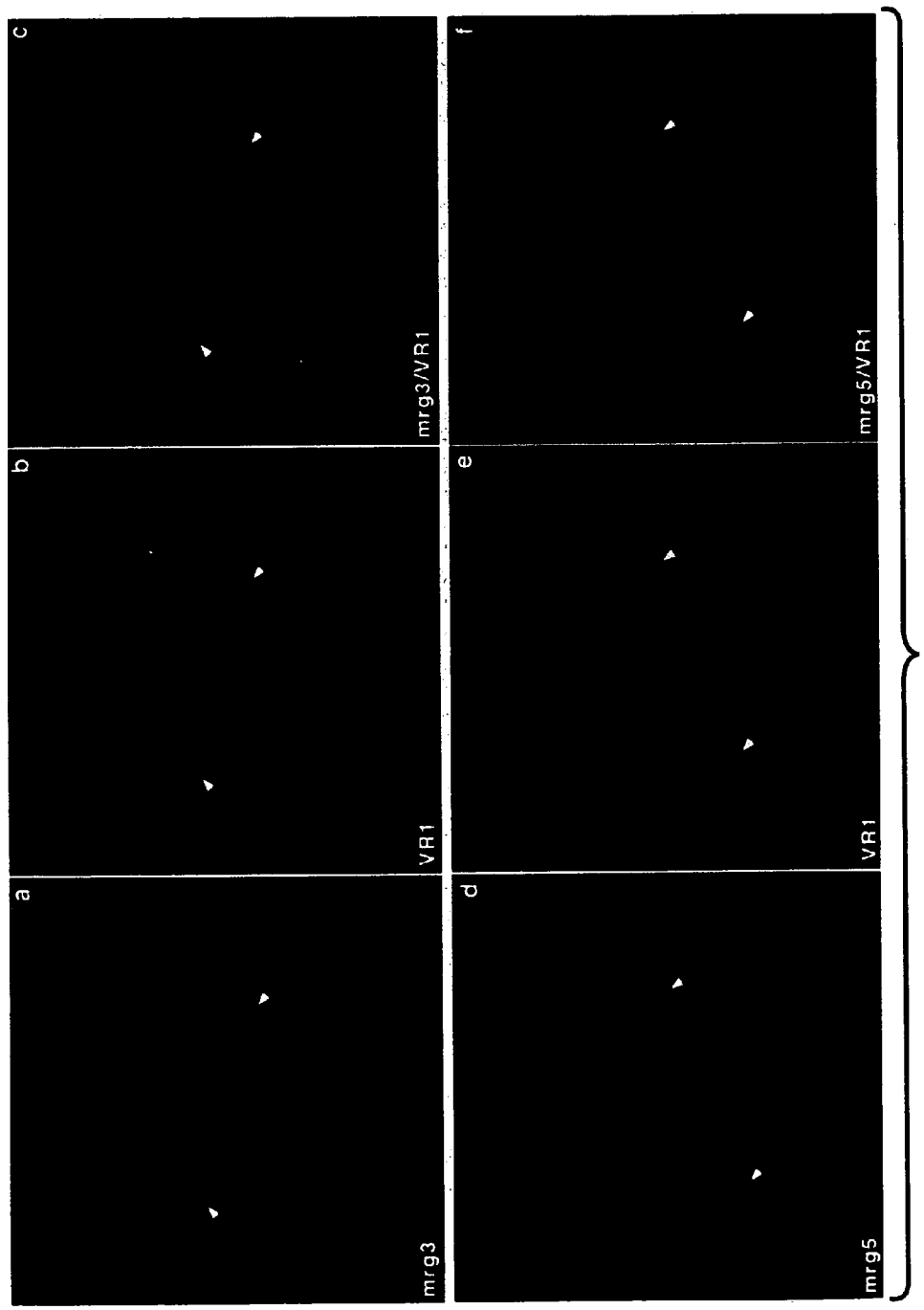
FIG. 2C. mrgs and VR1 define two different populations of nociceptive neurons in DRG. The combination of in situ hybridizations (red) with either mrg3 or mrg5 fluorescein-labeled antisense RNA probes and anti-VR1 antibody immunostaining (green) demonstrated that neither mrg3 (a-c) nor mrg5 (d-f) were expressed by VR1-positive neurons. In the merged images (c,f), there are no colocalizations of VR1 with either mrg3 or mrg5. The white arrowheads are pointed to mrgs-expressing but VR1-negative nociceptive neurons.

In FIG. 2C, mrgs and VR1 define two different populations of nociceptive neurons in DRG. The combination of in situ hybridizations (red) with either mrg3 or mrg5 fluorescein-labeled antisense RNA probes and anti-VR1 antibody immunostaining (green) demonstrated that neither mrg3 (a-c) nor mrg5 (d-f) were expressed by VR1-positive neurons. In the merged images (c,f), there are no colocalizations of VR1 with either mrg3 or mrg5. The white arrowheads are pointed to mrgs-expressing but VR1-negative nociceptive neurons.

In FIG. 2D mrgs are expressed by IB4$^+$ nociceptive neurons. Double labeling technique was used to colocalize IB4 (green; [b,e]) and mrgs (red; [a,d]) in DRG neurons. The expressions of mrg3 and mrg5 were visualized by in situ hybridization as described before. The same DRG sections were subsequently undergone through FITC-conjugated lectin IB4 binding. In the merged images (c,f), there are extensive overlappings between mrgs and IB4 stainings (yellow neurons indicated by arrowheads).

H. Methods to Identify Binding Partners

Another embodiment of the present invention provides methods of isolating and identifying binding partners of proteins of the invention. In these methods, a protein of the invention or a fragment of a protein of the invention, for instance, an extracellular domain fragment, is mixed with a potential binding partner or an extract or fraction of a cell under conditions that allow the association of potential binding partners with the protein of the invention. After mixing, peptides, polypeptides, proteins or other molecules that have become associated with a protein of the invention are separated from the mixture. The binding partner that bound to the protein of the invention can then be removed and further analyzed. To identify and isolate a binding partner, the entire protein, for instance a protein comprising the entire amino acid sequence of SEQ ID NO: 2, 4, 6, 8, 10, 12, 14, 16, 18, 19, 21, 23, 25, 27 or 29 can be used. Alternatively, a fragment of the polypeptide can be used.

As used herein, a cellular extract refers to a preparation or fraction which is made from a lysed or disrupted cell. The preferred source of cellular extracts will be cells derived from DRG. Alternatively, cellular extracts may be prepared from normal human kidney tissue or available cell lines, particularly kidney derived cell lines.

A variety of methods can be used to obtain an extract of a cell. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with the protein of the invention under conditions in which association of the protein with the binding partner can occur. A variety of conditions can be used, the most preferred being conditions that closely resemble conditions found in the cytoplasm of a human cell. Features such as osmolarity, pH, temperature, and the concentration of cellular extract used, can be varied to optimize the association of the protein with the binding partner.

After mixing under appropriate conditions, the bound complex is separated from the mixture. A variety of techniques can be utilized to separate the mixture. For example, antibodies specific to a protein of the invention can be used to immunoprecipitate the binding partner complex. Alternatively, standard chemical separation techniques such as chromatography and density/sediment centrifugation can be used.

After removal of non-associated cellular constituents found in the extract, the binding partner can be dissociated from the complex using conventional methods. For example, dissociation can be accomplished by altering the salt concentration or pH of the mixture.

To aid in separating associated binding partner pairs from the mixed extract, the protein of the invention can be immobilized on a solid support. For example, the protein can be attached to a nitrocellulose matrix or acrylic beads. Attachment of the protein to a solid support aids in separating peptide/binding partner pairs from other constituents found in the extract. The identified binding partners can be either a single protein or a complex made up of two or more proteins. Alternatively, binding partners may be identified using a Far-Western assay according to the procedures of Takayama et al. (1997) Methods Mol. Biol. 69:171-84 or Sauder et al. J. Gen. Virol. 77(5): 991-6 or identified through the use of epitope tagged proteins or GST fusion proteins.

Alternatively, the nucleic acid molecules of the invention can be used in cell based systems to detect protein-protein interactions (see WO99/55356). These systems have been used to identify other protein partner pairs and can readily be adapted to employ the nucleic acid molecules herein described.

I. Methods to Identify Agents that Modulate the Expression of a Nucleic Acid.

Another embodiment of the present invention provides methods for identifying agents that modulate the expression of a nucleic acid encoding a mrg or drg-12 protein of the invention. Such assays may utilize any available means of monitoring for changes in the expression level of the nucleic acids of the invention. As used herein, an agent is said to modulate the expression of a nucleic acid of the invention, for instance a nucleic acid encoding the protein having the sequence of SEQ ID NOS: 2, 4, 6, 8, 10, 12, 14, 16, 18, 19, 21, 23, 25, 27, or 29 if it is capable of up- or down-regulating expression of the gene or mRNA levels nucleic acid in a cell.

In one assay format, cell lines that contain reporter gene fusions between the open reading frames and/or the 5' or 3' regulatory sequences of a gene of the invention and any assayable fusion partner may be prepared. Numerous assayable fusion partners are known and readily available including the firefly luciferase gene and the gene encoding chloramphenicol acetyltransferase (Alam et al. (1990) *Anal. Biochem.* 188:245-254).

Cell lines containing the reporter gene fusions are then exposed to the agent to be tested under appropriate conditions and time. Differential expression of the reporter gene between samples exposed to the agent and control samples identifies agents which modulate the expression of a nucleic acid encoding a mrg or drg-12 protein.

Additional assay formats may be used to monitor the ability of the agent to modulate the expression of a nucleic acid encoding a mrg or drg-12 protein of the invention. For instance, mRNA expression may be monitored directly by hybridization to the nucleic acids of the invention. Cell lines are exposed to the agent to be tested under appropriate conditions and time and total RNA or mRNA is isolated by standard procedures such those disclosed in Sambrook et al. (*Molecular Cloning: A Laboratory Manual*, 2nd Ed. Cold Spring Harbor Laboratory Press, 1989).

Probes to detect differences in RNA expression levels between cells exposed to the agent and control cells may be prepared from the nucleic acids of the invention. It is preferable, but not necessary, to design probes which hybridize only with target nucleic acids under conditions of high stringency. Only highly complementary nucleic acid hybrids form under conditions of high stringency. Accordingly, the stringency of the assay conditions determines the amount of complementarity which should exist between two nucleic acid strands in order to form a hybrid. Stringency should be chosen to maximize the difference in stability between the probe:target hybrid and potential probe:non-target hybrids.

Probes may be designed from the nucleic acids of the invention through methods known in the art. For instance, the G+C content of the probe and the probe length can affect probe binding to its target sequence. Methods to optimize probe specificity are commonly available in Sambrook et al. (*Molecular Cloning: A Laboratory Manual*, 2nd Ed. Cold Spring Harbor Laboratory Press, NY, 1989) or Ausubel et al. (*Current Protocols in Molecular Biology*, Greene Publishing Co., NY, 1995).

Hybridization conditions are modified using known methods, such as those described by Sambrook et al. and Ausubel et al., as required for each probe. Hybridization of total cellular RNA or RNA enriched for polyA RNA can be accomplished in any available format. For instance, total cellular RNA or RNA enriched for polyA RNA can be affixed to a solid support and the solid support exposed to at least one probe comprising at least one, or part of one of the sequences of the invention under conditions in which the probe will specifically hybridize. Alternatively, nucleic acid fragments comprising at least one, or part of one of the sequences of the invention can be affixed to a solid support, such as a silicon chip or porous glass wafer. The wafer can then be exposed to total cellular RNA or polyA RNA from a sample under conditions in which the affixed sequences will specifically hybridize. Such wafers and hybridization methods are widely available, for example, those disclosed by Beattie (WO 95/11755). By examining for the ability of a given probe to specifically hybridize to an RNA sample from an untreated cell population and from a cell population exposed to the agent, agents which up or down regulate the expression of a nucleic acid encoding a mrg or drg-12 are identified.

Hybridization for qualitative and quantitative analysis of mRNAs may also be carried out by using a RNase Protection Assay (i.e., RPA, see Ma et al. (1996) Methods 10: 273-238). Briefly, an expression vehicle comprising cDNA encoding the gene product and a phage specific DNA dependent RNA polymerase promoter (e.g., T7, T3 or SP6 RNA polymerase) is linearized at the 3' end of the cDNA molecule, downstream from the phage promoter, wherein such a linearized molecule is subsequently used as a template for synthesis of a labeled antisense transcript of the cDNA by in vitro transcription. The labeled transcript is then hybridized to a mixture of isolated RNA (i.e., total or fractionated mRNA) by incubation at 45°

C. overnight in a buffer comprising 80% formamide, 40 mM Pipes, pH 6.4, 0.4 M NaCl and 1 mM EDTA. The resulting hybrids are then digested in a buffer comprising 40 μg/ml ribonuclease A and 2 μg/ml ribonuclease. After deactivation and extraction of extraneous proteins, the samples are loaded onto urea/polyacrylamide gels for analysis.

In another assay format, products, cells or cell lines are first be identified which express mrg or drg-12 gene products physiologically. Cell and/or cell lines so identified would be expected to comprise the necessary cellular machinery such that the fidelity of modulation of the transcriptional apparatus is maintained with regard to exogenous contact of agent with appropriate surface transduction mechanisms and/or the cytosolic cascades. Such cells or cell lines are then transduced or transfected with an expression vehicle (e.g., a plasmid or viral vector) construct comprising an operable non-translated 5' or 3'-promoter containing end of the structural gene encoding the instant gene products fused to one or more antigenic fragments, which are peculiar to the instant gene products, wherein said fragments are under the transcriptional control of said promoter and are expressed as polypeptides whose molecular weight can be distinguished from the naturally occurring polypeptides or may further comprise an immunologically distinct tag. Such a process is well known in the art.

Cells or cell lines transduced or transfected as outlined above are then contacted with agents under appropriate conditions; for example, the agent comprises a pharmaceutically acceptable excipient and is contacted with cells comprised in an aqueous physiological buffer such as phosphate buffered saline (PBS) at physiological pH, Eagles balanced salt solution (BSS) at physiological pH, PBS or BSS comprising serum or conditioned media comprising PBS or BSS and/or serum incubated at 37° C. Said conditions may be modulated as deemed necessary by one of skill in the art. Subsequent to contacting the cells with the agent, said cells will be disrupted and the polypeptides of the lysate are fractionated such that a polypeptide fraction is pooled and contacted with an antibody to be further processed by immunological assay (e.g., ELISA, immunoprecipitation or Western blot). The pool of proteins isolated from the "agent-contacted" sample will be compared with a control sample where only the excipient is contacted with the cells and an increase or decrease in the immunologically generated signal from the "agent-contacted" sample compared to the control will be used to distinguish the effectiveness of the agent.

J. Methods to Identify Agents that Modulate Protein Levels or at Least One Activity of the Proteins of DRG Primary Sensory Neurons.

Another embodiment of the present invention provides methods for identifying agents that modulate at least one activity of a mrg or drg-12 protein of the invention. Such methods or assays may utilize any means of monitoring or detecting the desired activity.

In one format, the relative amounts of a protein of the invention between a cell population that has been exposed to the agent to be tested compared to an un-exposed control cell population may be assayed. In this format, probes such as specific antibodies are used to monitor the differential expression of the protein in the different cell populations. Cell lines or populations are exposed to the agent to be tested under appropriate conditions and time. Cellular lysates may be prepared from the exposed cell line or population and a control, unexposed cell line or population. The cellular lysates are then analyzed with the probe.

Antibody probes are prepared by immunizing suitable mammalian hosts in appropriate immunization protocols using the peptides, polypeptides or proteins of the invention if they are of sufficient length, or, if desired, or if required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co. (Rockford, Ill.), may be desirable to provide accessibility to the hapten. The hapten peptides can be extended at either the amino or carboxy terminus with a cysteine residue or interspersed with cysteine residues, for example, to facilitate linking to a carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler and Milstein (Nature (1975) 256:495-497) or modifications which effect immortalization of lymphocytes or spleen cells, as is generally known. The immortalized cell lines secreting the desired antibodies are screened by immunoassay in which the antigen is the peptide hapten, polypeptide or protein. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of F(ab')$_2$ fragments is often preferable, especially in a therapeutic context, as these fragments are generally less immunogenic than the whole immunoglobulin.

The antibodies or fragments may also be produced, using current technology, by recombinant means. Antibody regions that bind specifically to the desired regions of the protein can also be produced in the context of chimeras with multiple species origin, such as humanized antibodies.

In another format, the activity of the proteins of the invention may be monitored in cells expressing the mrg and/or drg-12 proteins of the invention by assaying for physiological changes in the cells upon exposure to the agent or agents to be tested. Such physiological changes include but are not limited to the flow of current across the membrane of the cell. Methods to monitor or assay these changes are readily available. For instance, the mrg genes of the invention may be expressed in G$\alpha$15, a G protein $\alpha$ subunit that links receptor activation to increases in intracellular calcium [Ca$^{2+}$] which can be monitored at the single cell level using the FURA-2 calcium indicator dye as disclosed in Chandrashekar et al. (Cell 100 (6): 703-11, 2000) and Chandrashekar et al. (Cell 100:703-711, 2000).

Such assays may be formatted in any manner, particularly formats that allow high-throughput screening (HPT). In HPT assays of the invention, it is possible to screen thousands of different modulators or ligands in a single day. For instance, each well of a microtitre plate can be used to run a separate assay, for instance an assay based on the ability of the test compounds to modulate receptor activation derived increases in intracellular calcium as described above.

Agents that are assayed in the above method can be randomly selected or rationally selected or designed. As used herein, an agent is said to be randomly selected when the agent is chosen randomly without considering the specific sequences involved in the association of the a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a nonrandom basis which takes into account the sequence of the target site and/or its conformation in connection with the agent's action. Sites of interest might be peptides within the membrane spanning regions, cytoplasmic and extracellular peptide loops between these transmembrane regions, or selected sequences within the N-terminal extracellular domain or C-terminal intracellular domain. Agents can be rationally selected or rationally designed by utilizing the peptide sequences that make up these sites.

The agents of the present invention can be, as examples, peptides, small molecules, vitamin derivatives, as well as carbohydrates. Dominant negative proteins, DNAs encoding these proteins, antibodies to these proteins, peptide fragments of these proteins or mimics of these proteins may be introduced into cells to affect function. "Mimic" used herein refers to the modification of a region or several regions of a peptide molecule to provide a structure chemically different from the parent peptide but topographically and functionally similar to the parent peptide (see Grant G A. in: Meyers (ed.) Molecular Biology and Biotechnology (New York, VCH Publishers, 1995), pp. 659-664). A skilled artisan can readily recognize that there is no limit as to the structural nature of the agents of the present invention.

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies immunoreactive with critical positions of proteins of the invention. Antibody agents are obtained by immunization of suitable mammalian subjects with peptides, containing as antigenic regions, those portions of the protein intended to be targeted by the antibodies.

K. Uses for Agents that Modulate at Least One Activity of the Proteins.

As provided in the Examples, the mrg or drg-12 proteins and nucleic acids of the invention, are expressed in the primary nociceptive sensory neurons of DRG. Agents that modulate, up-or-down-regulate the expression of the protein or agents such as agonists or antagonists of at least one activity of the protein may be used to modulate biological and pathologic processes associated with the protein's function and activity.

As used herein, a subject can be any mammal, so long as the mammal is in need of modulation of a pathological or biological process mediated by a protein of the invention. The term "mammal" is defined as an individual belonging to the class Mammalia. The invention is particularly useful in the treatment of human subjects.

As described in the Figures and Examples, expression of a protein of the invention may be associated with biological processes of nociception, which may also be considered pathological processes. As used herein, an agent is said to modulate a biological or pathological process when the agent alters the degree, severity or nature of the process. For instance, the neuronal transmission of pain signals may be prevented or modulated by the administration of agents which up-regulate down-regulate or modulate in some way the expression or at least one activity of a protein of the invention.

The agents of the present invention can be provided alone, or in combination with other agents that modulate a particular biological or pathological process. For example, an agent of the present invention can be administered in combination with other known drugs or may be combined with analgesic drugs or non-analgesic drugs used during the treatment of pain that occurs in the presence or absence of one or more other pathological processes. As used herein, two or more agents are said to be administered in combination when the two agents are administered simultaneously or are administered independently in a fashion such that the agents will act at the same time.

The agents of the present invention can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The present invention further provides compositions containing one or more agents that modulate expression or at least one activity of a protein of the invention. While individual needs vary, determination of optimal ranges of effective amounts of each component is within the skill of the art. Typical dosages comprise 0.1 to 100 μg/kg body wt. The preferred dosages comprise 0.1 to 10 μg/kg body wt. The most preferred dosages comprise 0.1 to 1 μg/kg body wt.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

In practicing the methods of this invention, the compounds of this invention may be used alone or in combination, or in combination with other therapeutic or diagnostic agents. In certain preferred embodiments, the compounds of this invention may be co-administered along with other compounds typically prescribed for these conditions according to generally accepted medical practice. The compounds of this invention can be utilized in vivo, ordinarily in mammals, such as humans, sheep, horses, cattle, pigs, dogs, cats, rats and mice, or in vitro.

L. Transgenic Animals

Transgenic animals containing mutant, knock-out or modified genes corresponding to the mrg and/or drg-12 sequences are also included in the invention. Transgenic animals are genetically modified animals into which recombinant, exogenous or cloned genetic material has been experimentally transferred. Such genetic material is often referred to as a "transgene". The nucleic acid sequence of the transgene, in this case a form of SEQ ID NO: 1, 3, 5, 7, 9, 11, 13, 15, 17, 20, 22, 24, 26 or 28 may be integrated either at a locus of a genome where that particular nucleic acid sequence is not otherwise normally found or at the normal locus for the transgene. The transgene may consist of nucleic acid sequences derived from the genome of the same species or of a different species than the species of the target animal.

The term "germ cell line transgenic animal" refers to a transgenic animal in which the genetic alteration or genetic information was introduced into a germ line cell, thereby conferring the ability of the transgenic animal to transfer the genetic information to offspring. If such offspring in fact possess some or all of that alteration or genetic information, then they too are transgenic animals.

The alteration or genetic information may be foreign to the species of animal to which the recipient belongs, foreign only to the particular individual recipient, or may be genetic information already possessed by the recipient. In the last case, the altered or introduced gene may be expressed differently than the native gene.

Transgenic animals can be produced by a variety of different methods including transfection, electroporation, microinjection, gene targeting in embryonic stem cells and recombinant viral and retroviral infection (see, e.g., U.S. Pat. No. 4,736,866; U.S. Pat. No. 5,602,307; Mullins et al. (1993) Hypertension 22(4):630-633; Brenin et al. (1997) Surg. Oncol. 6(2) 99-110; Tuan (ed.), Recombinant Gene Expression Protocols, Methods in Molecular Biology No. 62, Humana Press (1997)).

A number of recombinant or transgenic mice have been produced, including those which express an activated oncogene sequence (U.S. Pat. No. 4,736,866); express simian SV40 T-antigen (U.S. Pat. No. 5,728,915); lack the expression of interferon regulatory factor 1 (IRF-1) (U.S. Pat. No. 5,731,490); exhibit dopaminergic dysfunction (U.S. Pat. No. 5,723,719); express at least one human gene which participates in blood pressure control (U.S. Pat. No. 5,731,489); display greater similarity to the conditions existing in naturally occurring Alzheimer's disease (U.S. Pat. No. 5,720,936); have a reduced capacity to mediate cellular adhesion (U.S. Pat. No. 5,602,307); possess a bovine growth hormone gene (Clutter et al. (1996) Genetics 143(4):1753-1760); or, are capable of generating a fully human antibody response (McCarthy (1997) The Lancet 349(9049):405).

While mice and rats remain the animals of choice for most transgenic experimentation, in some instances it is preferable or even necessary to use alternative animal species. Transgenic procedures have been successfully utilized in a variety of non-murine animals, including sheep, goats, pigs, dogs, cats, monkeys, chimpanzees, hamsters, rabbits, cows and guinea pigs (see, e.g., Kim et al. (1997) Mol. Reprod. Dev. 46(4):515-526; Houdebine (1995) Reprod. Nutr. Dev. 35(6): 609-617; Petters (1994) Reprod. Fertil. Dev. 6(5):643-645; Schnieke et al. (1997) Science 278(5346):2130-2133; and Amoah (1997) J. Animal Science 75(2):578-585).

The method of introduction of nucleic acid fragments into recombination competent mammalian cells can be by any method that favors co-transformation of multiple nucleic acid molecules. Detailed procedures for producing transgenic animals are readily available to one skilled in the art, including the disclosures in U.S. Pat. No. 5,489,743 and U.S. Pat. No. 5,602,307.

M. Diagnostic Methods

As described in the Examples, the genes and proteins of the invention may be used to diagnose or monitor the presence or absence of sensory neurons and of biological or pathological activity in sensory neurons. For instance, expression of the genes or proteins of the invention may be used to differentiate between normal and abnormal sensory neuronal activities associated with acute pain, chronic intractable pain, or allodynia. Expression levels can also be used to differentiate between various stages or the severity of neuronal abnormalities. One means of diagnosing pathological states of sensory neurons involved in pain transmission using the nucleic acid molecules or proteins of the invention involves obtaining tissue from living subjects. These subjects may be non-human animal models of pain.

The use of molecular biological tools has become routine in forensic technology. For example, nucleic acid probes may be used to determine the expression of a nucleic acid molecule comprising all or at least part of the sequences of the invention in forensic/pathology specimens. Further, nucleic acid assays may be carried out by any means of conducting a transcriptional profiling analysis. In addition to nucleic acid analysis, forensic methods of the invention may target the proteins of the invention to determine up or down regulation of the genes (Shiverick et al., Biochim Biophys Acta (1975) 393(1): 124-33).

Methods of the invention may involve treatment of tissues with collagenases or other proteases to make the tissue amenable to cell lysis (Semenov et al., Biull Eksp Biol Med (1987) 104(7): 113-6). Further, it is possible to obtain biopsy samples from different regions of the kidney for analysis.

Assays to detect nucleic acid or protein molecules of the invention may be in any available format. Typical assays for nucleic acid molecules include hybridization or PCR based formats. Typical assays for the detection of proteins, polypeptides or peptides of the invention include the use of antibody probes in any available format such as in situ binding assays, etc. See Harlow et al., Antibodies: A Laboratory Manual, Cold Spring Harbor Laboratory, 1988 and Section G. In preferred embodiments, assays are carried-out with appropriate controls.

The above methods may also be used in other diagnostic protocols, including protocols and methods to detect disease states in other tissues or organs.

N. Methods of Identifying Other Genes Expressed in Primary Nociceptive Sensory Neurons.

As described in the Examples, the mrg and drg-12 genes of the invention have been identified RNA using a suppression-PCR-based method (Clontech) to enrich for genes expressed in the DRG of wild type but not Ngn1 mutant mice. This general method may be used to identify and isolate other DRG specific genes by producing transgenic mice that do not express other genes required for the development or presence of the nociceptive subset of DRG neurons. For instance, TrkA$^{-/-}$ mice may be used in the methods of the invention to isolate other genes associated with nociceptice DRG neuron (see Lindsay 1996) Philos. Trans R. Soc. Lond. B. Biol. Sci. 351(1338):365-73 and Walsh et al. J. Neurosci. 19(10):4155-68).

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

Positive Selection-Based Differential Hybridization Between Wild Type and Ngn1$^{-/-}$ DRG to Identify Candidate Genes Involved in Nociception RNA was isolated from the dorsal root ganglia (DRG) of newborn wild type or Ngn1$^{-/-}$ mice (see Ma et al. Genes Develop. 13:1717-1728 (1999), Fode et al. Neuron 20:483-494 (1998) and Ma et al. Neuron 20:469-482 (1998). A suppression-PCR-based method (Clontech) was then used to enrich for genes expressed in wild type but not Ngn1 mutant DRG. Approximately 1,600 positives were identified in the primary screen, and of these 142 were sequenced. Fifty of these represented known genes, and 92 represented new genes (see Table I). Among the known genes were several signaling molecules specifically expressed in nociceptive sensory neurons. These included VR-1, calcitonin gene-related peptide (CGRP), the tetrodotoxin-insensitive sodium channel (SNS-TTXi) and diacylglycerol kinase. Among the new genes were several encoding proteins with structural features characteristic of ion channels or receptors, which were revealed by in situ hybridization to be specifically expressed in a subset of DRG sensory neurons. These molecules are described in more detail in Examples 2 and 3.

TABLE I

Summary of results of the differential hybridization screening for genes involved in pain sensation.

| # of times isolated from the screen | Name |
|---|---|
| | A. Known genes: |
| 13 | NaN |
| 9 | Diacylglycerol kinase |
| 7 | Synaptophysin Iia |
| 5 | Vanillinoid receptor1 |
| 3 | GluR5-2c |
| 2 | CGRP |
| 2 | CLIM1 |
| 1 | SNS-TTXi |
| 1 | Alpha N-catenin I |
| 1 | Brain Na channel III |
| 1 | NICA6 |
| 1 | Secretogranin |
| | B. Novel genes: |
| 2 | Mrg3 (a novel G-protein-coupled receptor) |
| 2 | DRG12 |

Note: Previous studies have shown that the genes with bolded letters are expressed specifically in nociceptors.

Example 2

Figure 1C:
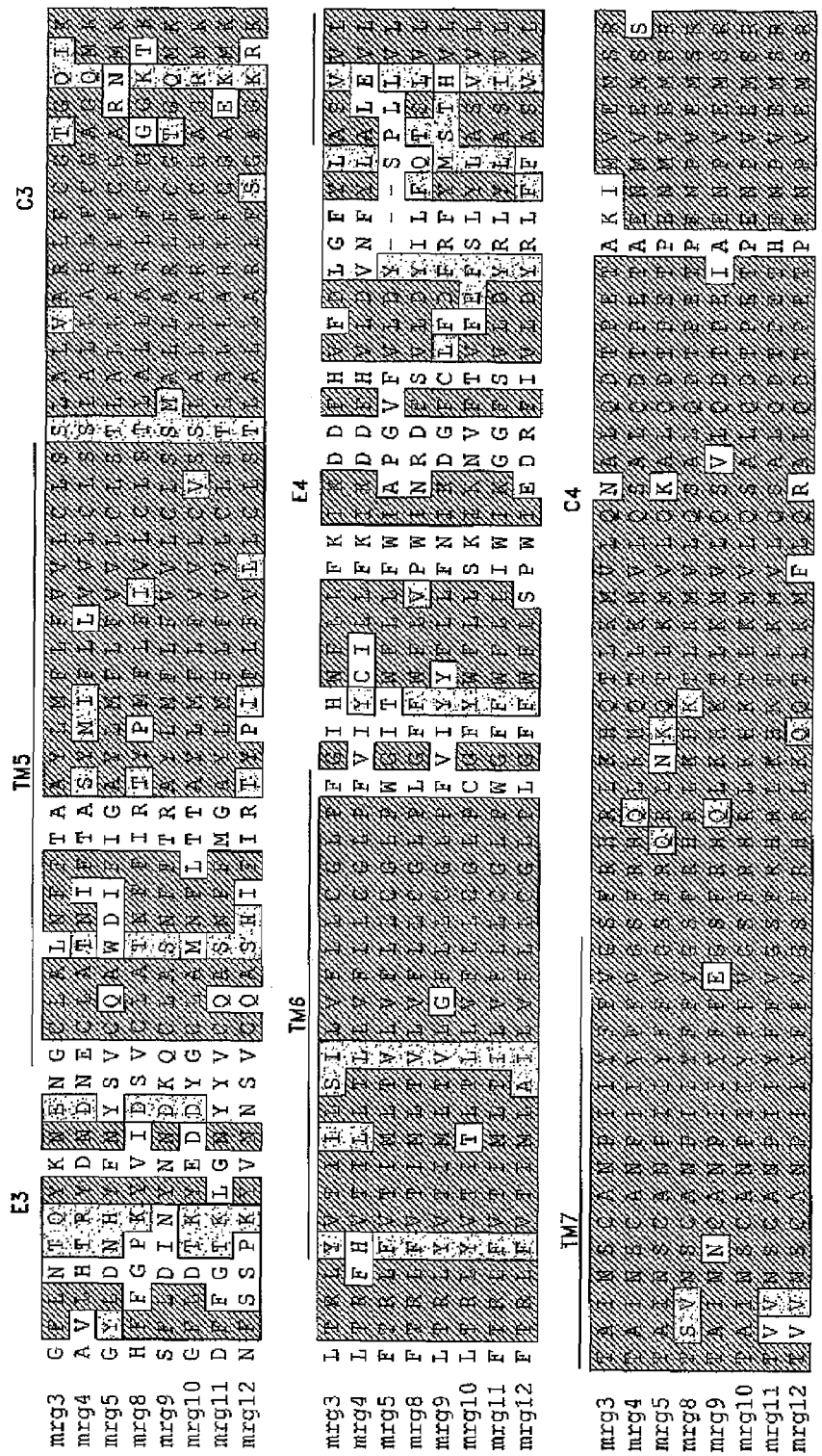
Figure 1D:
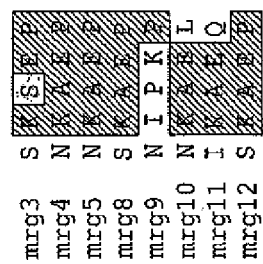

A Novel Family of Putative G Protein-Coupled Receptors Specifically Expressed in Nociceptive Sensory Neurons Among the novel genes isolated from the screen were two independent clones encoding a receptor protein with 7 transmembrane segments (SEQ ID NO: 1), a characteristic of G protein-coupled receptors. The novel 7 transmembrane receptor isolated is most closely related to the oncogene mas, and therefore has been named mas-related gene-3 (mrg3). A complete coding sequence for mrg3 has been deduced from the a genomic DNA sequence (FIGS. 1B-D and SEQ ID NO: 2).

Such G protein-coupled receptors are expressed in other classes of sensory neurons, such as olfactory and gustatory neurons, but molecules in this class had not previously been described in DRG sensory neurons, with the exception of the Protease-Activated Receptors (PARs).

Further screening of mouse DRG cDNA library and mouse genomic library by using mrg3 DNA as a probe has identified nine additional closely related genes named mrg4, mrg5, mrg6, mrg7, mrg8, mrg9, mrg10, mrg11, and mrg12. Among them, mrg4, 5 and mrg 8-12 contain full length open reading frames (see FIGS. 1A-1D). Two human homologues were found by searching databases using the blast program. The protein alignment of the eight mrg genes suggested that they define a novel G protein-coupled receptor gene family (FIGS. 1A-1D).

All of the eight full-length mas-related genes, mrg3-5 and mrg8-12, are enriched in nociceptive sensory neurons as indicated by their expression in a subset of DRG sensory neurons which are eliminated in ngn1$^{-/-}$ mutant DRG (FIGS. 2 and 2A).

Example 3

A Novel Two-Transmembrane Segment Protein Specifically Expressed in Nociceptive Sensory Neurons Another novel gene isolated in this screen, drg12 (SEQ ID NO: 13), encodes a protein with two putative transmembrane segments (SEQ ID NO: 14). In situ hybridization indicates that, like the mrg genes, this gene is also specifically expressed in a subset of DRG sensory neurons. Although there are no obvious homologies between this protein and other sequences in the database, it is noteworthy that two purinergic receptors specifically expressed in nociceptive sensory neurons ($P_2X_2$ and $P_2X_3$) have a similar bipartite transmembrane topology. Therefore it is likely that drg12 also encodes a receptor or ion channel involved in nociceptive sensory transduction or its modulation. The hydrophobicity of a homologous region of a drg12 human sequence (SEQ ID NO: 19) is compared with the hydrophobicity of mouse drg12 in FIG. 4.

Example 4 mrg and drg-12 Genes are Specifically Expressed in Nociceptive Sensory Neurons

The prediction of function for mrg-family and drg12 genes is based on their structure and expression pattern, taken together. mrg and drg12 genes are expressed in subsets of small-diameter neurons in the dorsal root ganglia (DRG) of the mouse. This expression is highly specific, in that expression of these genes has thus far not been detected in any other tissue of the body, or in any other region of the nervous system thus far examined. This indicates that Mrg and drg12 genes are expressed in primary sensory neurons. However, DRG contain different classes of neurons subserving different types of sensation: e.g., heat, pain, touch and body position. Independent identification is provided by the fact that the neurons that express the mrg-family and drg12 genes are largely or completely eliminated in Ngn1$^{-/-}$/DRG (FIG. 2), because the Ngn1 mutation is independently known to largely or completely eliminate the nociceptive (noxious stimuli-sensing) subset of DRG neurons, identified by expression of the independent markers trkA, VR-1 and SNS-TTXi (Ma et. al., (1999) Genes & Dev. op. cit.). The loss of mrg- and drg12-expressing neurons in Ngn1$^{-/-}$ mutant DRG therefore indicates that these genes are very likely expressed in nociceptive sensory neurons. Although small numbers of sensory neurons of other classes (trkB$^+$ and trkC$^+$) are eliminated in the Ngn1$^{-/-}$ mutant as well, mrg and drg12 genes are unlikely to be expressed in these classes of sensory neurons, because if they were then the majority of mrg- and drg12-expressing sensory neurons would be predicted to be spared in the Ngn1$^{-/-}$ mutant, and that is not the case. Double labeling experiment using mrgs antisense RNA probes with anti-TrkA antibody have confirmed that mrgs are expressed by TrkA+ nociceptive neurons in DRG (see FIG. 2B). Additional double labeling experiments using mrgs antisense RNA probes with anti-VR1 and IB4-labeling have shown that mrgs are preferentially expressed by IB4+ nociceptive neurons but not VR1-expressing nociceptive neurons (FIGS. 2C and 2D). Previous studies had shown that IB4+ nociceptive neurons were involved in neuropathic pain resulting from nerve injury (Malmberg A B et al. 1997). Neuropathic pain including postherpetic neuralgia, reflex sympathetic dystrophy, and phantom limb pain is the most difficult pain to be managed. mrgs may play essential roles in mediating neuropathic pain and may provide alternative solutions to manage neuropathic pain.

Mrg-Family Genes Encode Putative G-Protein Coupled Receptors (GPCRs).

Hydrophobicity plots of the encoded amino acid sequences of the mrg-family genes predicts membrane proteins with 7 transmembrane segments. Such a structure is characteristic of receptors that signal through "G-proteins." G proteins are a family of cytoplasmic molecules that activate or inhibit enzymes involved in the generation or degradation of "second messenger" molecules, such as cyclic nucleotides (cAMP, cGMP), IP$_3$ and intracellular free calcium (Ca$^{++}$). Such second messenger molecules then activate or inhibit other molecules involved in intercellular signaling, such as ion channels and other receptors.

G protein-coupled receptors (GPCRs) constitute one of the largest super-families of membrane receptors, and contain many subfamilies of receptors specific for different ligands. These ligands include neurotransmitters and neuropeptides manufactured by the body (e.g., noradrenaline, adrenaline, dopamine; and substance P, somatostatin, respectively), as well as sensory molecules present in the external world (odorants, tastants).

Although the mrg-family genes are highly homologous, the most divergent regions were the extracellular domains (see FIGS. 1B-1D). The variability of the extracellular domains of mrg family suggests that they may recognize different ligands.

The fact that the mrg-family genes encode GPCRs, and are specifically expressed in nociceptive sensory neurons, suggest that these receptors are involved, directly or indirectly, in the sensation or modulation of pain, heat or other noxious stimuli. Therefore the mrg-encoded receptors are useful as targets for identifying drugs that affect the sensation or modulation or pain, heat or other noxious stimuli. The nature of the most useful type of drug (agonistic or antagonistic) will reflect the nature of the normal influence of these receptors on the sensation of such noxious stimuli. For example, if mrg-encoded receptors normally act negatively, to inhibit or suppress pain, then agonistic drugs would provide useful therapeutics; conversely, if the receptors normally act positively, to promote or enhance pain, then antagonistic drugs would provide useful therapeutics. There might even be certain clinical settings in which it would be useful to enhance sensitivity to noxious stimuli, for example in peripheral sensory neuropathies associated with diabetes.

The nature of the influence of mrg-encoded GPCRs on pain sensation may be revealed by the phenotypic consequences of targeted mutation of these genes in mice. For example, if such mice displayed enhanced sensitivity to noxious stimuli, then it could be concluded that the receptors normally function to inhibit or suppress pain responses, and vice-versa. Alternatively, high-throughput screens may be used to identify small molecules that bind tightly to the mrg-encoded receptors. Such molecules would be expected to fall into two categories: agonists and antagonists. Agonists would be identified by their ability to activate intracellular second messenger pathways in a receptor-dependent manner, while antagonists would inhibit them. Testing of such drugs in animal models of pain sensitivity will then reveal further information concerning the function of the GPCRs: for example, if the molecules behave as receptor antagonists in vitro, and they suppress sensitivity or responsiveness to noxious stimuli in vivo, then it may be concluded that the receptor normally functions to promote or enhance pain sensation. Conversely, if receptor agonists suppress, while antagonists enhance, pain sensation in vivo, then it may be concluded that the receptor normally functions to suppress or inhibit pain sensation.

drg12 Encodes a Putative Transmembrane Signaling Molecule

Hydrophobicity plots of the encoded amino acid sequence of the drg12 gene predicts a membrane protein with 2 transmembrane segments. The membrane localization of this protein has been verified by immuno-staining of cultured cells transfected with an epitope-tagged version of the polypeptide. Although the DRG12 amino acid sequence has no homology to known families of proteins, its bipartite transmembrane structure strongly suggests that it is involved in some aspect of intercellular signaling, for example as a receptor, ion channel or modulator of another receptor or ion channel. This prediction is supported by the precedent that two known receptors with a similar bipartite transmembrane topology, the purinergic P$_2$X$_2$ and P$_2$X$_3$ receptors, are like DRG12, specifically expressed in nociceptive sensory neurons.

Based on this structural data, and its specific expression in nociceptive sensory neurons, it is probable that DRG12 is involved, directly or indirectly, in the sensation or modulation of noxious stimuli. Accordingly, the drg12-encoded protein is a useful target for the development of novel therapeutics for the treatment of pain.

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

What is claimed is:

1. An isolated nucleic acid molecule that encodes a polypeptide comprising the amino acid sequence of SEQ ID NO: 16.

2. The isolated nucleic acid molecule of claim 1, wherein the nucleic acid molecule comprises nucleotides 1-966 of SEQ ID NO: 15.

3. The isolated nucleic acid molecule of claim 1, wherein the nucleic acid molecule consists of nucleotides 1-966 of SEQ ID NO: 15.

4. The isolated nucleic acid molecule of claim 1, wherein the nucleic acid molecule comprises nucleotides 1-969 of SEQ ID NO:15.

5. The isolated nucleic acid molecule of claim 1, wherein the nucleic acid molecule consists of nucleotides 1-969 of SEQ ID NO: 15.

6. The isolated nucleic acid molecule of any one of claims 1-5, wherein said nucleic acid molecule is operably linked to one or more expression control elements.

7. A vector comprising an isolated nucleic acid molecule of any one of claims 1-5.

8. A host cell transformed to contain the nucleic acid molecule of any one of claims 1-5.

9. A host cell comprising a vector of claim 7.

10. A host cell of claim 9, wherein said host is selected from the group consisting of prokaryotic hosts and eukaryotic hosts.

11. A method for producing a polypeptide comprising the step of culturing a host cell transformed with the nucleic acid molecule of any one of claims 1-5 under conditions in which the protein encoded by said nucleic acid molecule is expressed.

12. The method of claim 11, wherein said host cell is selected from the group consisting of prokaryotic hosts and eukaryotic hosts.

* * * * *

SEQUENCE LISTING

<160> NUMBER OF SEQ ID NOS: 29

<210> SEQ ID NO 1
<211> LENGTH: 1088
<212> TYPE: DNA
<213> ORGANISM: Mus musculus
<220> FEATURE:
<221> NAME/KEY: CDS
<222> LOCATION: (34)..(1026)
<223> OTHER INFORMATION: Mrg3
<221> NAME/KEY: source
<222> LOCATION: (451)..(468)
<223> OTHER INFORMATION: 18 base region used as cloning primer to locate
      family members
<221> NAME/KEY: source
<222> LOCATION: (880)..(897)
<223> OTHER INFORMATION: 18 base region used as cloning primer to locate
      family members

<400> SEQUENCE: 1

```
acagaagcca gagagctaca tccagcaaga gga atg ggg gaa agc agc acc tgt         54
                                    Met Gly Glu Ser Ser Thr Cys
                                     1               5 gca ggg ttt cta gcc cta aac aca tcg gcc tcg cca aca gca ccc aca        102
Ala Gly Phe Leu Ala Leu Asn Thr Ser Ala Ser Pro Thr Ala Pro Thr
         10                  15                  20 aca act aat cca atg gac aat acc atc cct gga ggt atc aac atc acg        150
Thr Thr Asn Pro Met Asp Asn Thr Ile Pro Gly Gly Ile Asn Ile Thr
     25                  30                  35 att ctg atc cca aac ttg atg atc atc atc ttc gga ctg gtc ggg ctg        198
Ile Leu Ile Pro Asn Leu Met Ile Ile Ile Phe Gly Leu Val Gly Leu
 40                  45                  50                  55 aca gga aat ggc att gtg ttc tgg ctc ctg ggc ttc tgt ttg cac agg        246
Thr Gly Asn Gly Ile Val Phe Trp Leu Leu Gly Phe Cys Leu His Arg
                 60                  65                  70 aac gcc ttc tca gtc tac atc cta aac tta gct cta gct gac ttc ttc        294
Asn Ala Phe Ser Val Tyr Ile Leu Asn Leu Ala Leu Ala Asp Phe Phe
             75                  80                  85 ttc ctc cta ggt cac atc ata gat tcc ata ctg ctt ctt ctc aat gtt        342
Phe Leu Leu Gly His Ile Ile Asp Ser Ile Leu Leu Leu Leu Asn Val
         90                  95                 100 ttc tac cca att acc ttt ctc ttg tgc ttt tac acg atc atg atg gtt        390
Phe Tyr Pro Ile Thr Phe Leu Leu Cys Phe Tyr Thr Ile Met Met Val
     105                 110                 115 ctc tat atc gca ggc ctg agc atg ctc agt gcc atc agc act gag cgc        438
Leu Tyr Ile Ala Gly Leu Ser Met Leu Ser Ala Ile Ser Thr Glu Arg
120                 125                 130                 135 tgc ctg tct gta ctg tgc ccc atc tgg tat cac tgt cac cgc cca gaa        486
Cys Leu Ser Val Leu Cys Pro Ile Trp Tyr His Cys His Arg Pro Glu
                 140                 145                 150 cac aca tca act gtc atg tgt gct gtc atc tgg gtc ctg tcc ctg ttg        534
His Thr Ser Thr Val Met Cys Ala Val Ile Trp Val Leu Ser Leu Leu
             155                 160                 165 atc tgc att ctg aat agt tat ttc tgc ggt ttc tta aat acc caa tat        582
Ile Cys Ile Leu Asn Ser Tyr Phe Cys Gly Phe Leu Asn Thr Gln Tyr
         170                 175                 180 aaa aat gaa aat ggg tgt ctg gca ttg aac ttc ttt act gct gca tac        630
Lys Asn Glu Asn Gly Cys Leu Ala Leu Asn Phe Phe Thr Ala Ala Tyr
     185                 190                 195 ctg atg ttt ttg ttt gtg gtc ctc tgt ctg tcc agc ctg gct ctg gtg        678
Leu Met Phe Leu Phe Val Val Leu Cys Leu Ser Ser Leu Ala Leu Val
200                 205                 210                 215
```

```
gcc agg ttg ttc tgt ggt act ggg cag ata aag ctt acc aga ttg tat    726
Ala Arg Leu Phe Cys Gly Thr Gly Gln Ile Lys Leu Thr Arg Leu Tyr
            220                 225                 230 gta acc att att ctg agc att ttg gtt ttt ctc ctt tgc gga ttg ccc    774
Val Thr Ile Ile Leu Ser Ile Leu Val Phe Leu Leu Cys Gly Leu Pro
                235                 240                 245 ttt ggc atc cac tgg ttt ctg tta ttc aag att aag gat gat ttt cat    822
Phe Gly Ile His Trp Phe Leu Leu Phe Lys Ile Lys Asp Asp Phe His
        250                 255                 260 gta ttt gat ctt gga ttt tat ctg gca tca gtt gtc ctg act gct att    870
Val Phe Asp Leu Gly Phe Tyr Leu Ala Ser Val Val Leu Thr Ala Ile
    265                 270                 275 aat agc tgt gcc aac ccc atc att tac ttc ttc gtg gga tcc ttc agg    918
Asn Ser Cys Ala Asn Pro Ile Ile Tyr Phe Phe Val Gly Ser Phe Arg
280                 285                 290                 295 cat cgg ttg aag cac cag acc ctc aaa atg gtt ctc cag aat gca ctg    966
His Arg Leu Lys His Gln Thr Leu Lys Met Val Leu Gln Asn Ala Leu
                300                 305                 310 caa gac act cct gag aca gcc aaa atc atg gtg gag atg tca aga agc    1014
Gln Asp Thr Pro Glu Thr Ala Lys Ile Met Val Glu Met Ser Arg Ser
            315                 320                 325 aaa tca gag cca tgatgaagag cctttgcctg gcccttagaa gtggctttgg        1066
Lys Ser Glu Pro
        330 ggtgagcatt gccctgctgc ac                                           1088
```

<210> SEQ ID NO 2
<211> LENGTH: 331
<212> TYPE: PRT
<213> ORGANISM: Mus musculus

<400> SEQUENCE: 2

```
Met Gly Glu Ser Ser Thr Cys Ala Gly Phe Leu Ala Leu Asn Thr Ser
 1               5                   10                  15

Ala Ser Pro Thr Ala Pro Thr Thr Thr Asn Pro Met Asp Asn Thr Ile
                20                  25                  30

Pro Gly Gly Ile Asn Ile Thr Ile Leu Ile Pro Asn Leu Met Ile Ile
            35                  40                  45

Ile Phe Gly Leu Val Gly Leu Thr Gly Asn Gly Ile Val Phe Trp Leu
        50                  55                  60

Leu Gly Phe Cys Leu His Arg Asn Ala Phe Ser Val Tyr Ile Leu Asn
65                  70                  75                  80

Leu Ala Leu Ala Asp Phe Phe Leu Leu Gly His Ile Ile Asp Ser
                85                  90                  95

Ile Leu Leu Leu Leu Asn Val Phe Tyr Pro Ile Thr Phe Leu Leu Cys
                100                 105                 110

Phe Tyr Thr Ile Met Met Val Leu Tyr Ile Ala Gly Leu Ser Met Leu
            115                 120                 125

Ser Ala Ile Ser Thr Glu Arg Cys Leu Ser Val Leu Cys Pro Ile Trp
        130                 135                 140

Tyr His Cys His Arg Pro Glu His Thr Ser Thr Val Met Cys Ala Val
145                 150                 155                 160

Ile Trp Val Leu Ser Leu Leu Ile Cys Ile Leu Asn Ser Tyr Phe Cys
                165                 170                 175

Gly Phe Leu Asn Thr Gln Tyr Lys Asn Glu Asn Gly Cys Leu Ala Leu
            180                 185                 190
```

```
Asn Phe Phe Thr Ala Ala Tyr Leu Met Phe Leu Phe Val Val Leu Cys
            195                 200                 205

Leu Ser Ser Leu Ala Leu Val Ala Arg Leu Phe Cys Gly Thr Gly Gln
    210                 215                 220

Ile Lys Leu Thr Arg Leu Tyr Val Thr Ile Ile Leu Ser Ile Leu Val
225                 230                 235                 240

Phe Leu Leu Cys Gly Leu Pro Phe Gly Ile His Trp Phe Leu Leu Phe
                245                 250                 255

Lys Ile Lys Asp Asp Phe His Val Phe Asp Leu Gly Phe Tyr Leu Ala
                260                 265                 270

Ser Val Val Leu Thr Ala Ile Asn Ser Cys Ala Asn Pro Ile Ile Tyr
            275                 280                 285

Phe Phe Val Gly Ser Phe Arg His Arg Leu Lys His Gln Thr Leu Lys
    290                 295                 300

Met Val Leu Gln Asn Ala Leu Gln Asp Thr Pro Glu Thr Ala Lys Ile
305                 310                 315                 320

Met Val Glu Met Ser Arg Ser Lys Ser Glu Pro
                325                 330

<210> SEQ ID NO 3
<211> LENGTH: 1234
<212> TYPE: DNA
<213> ORGANISM: Mus musculus
<220> FEATURE:
<221> NAME/KEY: CDS
<222> LOCATION: (137)..(1051)
<223> OTHER INFORMATION: Mrg4

<400> SEQUENCE: 3
tctgtagtga ctgtatcttt ccttctacac aagccagtga gctacatcca acaagaggat     60
tggggaaagc aatggtgaag catttcttgc ctttaagacc tcagcctcac caacagcacc    120
agtgacaaca aatcca atg gac gaa acc ctc cct gga agt atc aac att agg    172
               Met Asp Glu Thr Leu Pro Gly Ser Ile Asn Ile Arg
                 1               5                  10 att ctg atc cca aaa ttg atg atc atc atc ttc gga ctg gtc gga ctg    220
Ile Leu Ile Pro Lys Leu Met Ile Ile Ile Phe Gly Leu Val Gly Leu
        15                  20                  25 atg gga aac gcc att gtg ttc tgg ctc ctg ggc ttc cac ttg cgc aag    268
Met Gly Asn Ala Ile Val Phe Trp Leu Leu Gly Phe His Leu Arg Lys
    30                  35                  40 aat gac ttc tca ctc tac atc cta aac ttg gcc cgg gct gac ttc ctt    316
Asn Asp Phe Ser Leu Tyr Ile Leu Asn Leu Ala Arg Ala Asp Phe Leu
45                  50                  55                  60 ttc ctc ctc agt agt atc ata gct tcc acc ctg ttt ctt ctc aaa gtt    364
Phe Leu Leu Ser Ser Ile Ile Ala Ser Thr Leu Phe Leu Leu Lys Val
                65                  70                  75 tcc tac ctc agc atc atc ttt cac ttg tgc ttt aac acc att atg atg    412
Ser Tyr Leu Ser Ile Ile Phe His Leu Cys Phe Asn Thr Ile Met Met
            80                  85                  90 gtt gtc tac atc aca ggg ata agc atg ctc agt gcc atc agc act gag    460
Val Val Tyr Ile Thr Gly Ile Ser Met Leu Ser Ala Ile Ser Thr Glu
        95                  100                 105 tgc tgc ctg tct gtc ctg tgc ccc acc tgg tat cgc tgc cac cgt cca    508
Cys Cys Leu Ser Val Leu Cys Pro Thr Trp Tyr Arg Cys His Arg Pro
    110                 115                 120 gta cat aca tca act gtc atg tgt gct gtg atc tgg gtc cta tcc ctg    556
Val His Thr Ser Thr Val Met Cys Ala Val Ile Trp Val Leu Ser Leu
125                 130                 135                 140
```

| | | | | | | | | | | | | | | | | |
|---|---|---|---|---|---|---|---|---|---|---|---|---|---|---|---|---|
| ttg | atc | tgc | att | ctg | aat | agc | tat | ttc | tgt | gct | gtc | tta | cat | acc | aga | 604 |
| Leu | Ile | Cys | Ile | Leu | Asn | Ser | Tyr | Phe | Cys | Ala | Val | Leu | His | Thr | Arg | |
| | | | 145 | | | | | 150 | | | | | 155 | | | |
| tat | gat | aat | gac | aat | gag | tgt | ctg | gca | act | aac | atc | ttt | acc | gcc | tcg | 652 |
| Tyr | Asp | Asn | Asp | Asn | Glu | Cys | Leu | Ala | Thr | Asn | Ile | Phe | Thr | Ala | Ser | |
| | | | 160 | | | | | 165 | | | | | 170 | | | |
| tac | atg | ata | ttt | ttg | ctt | gtg | gtc | ctc | tgt | ctg | tcc | agc | ctg | gct | ctg | 700 |
| Tyr | Met | Ile | Phe | Leu | Leu | Val | Val | Leu | Cys | Leu | Ser | Ser | Leu | Ala | Leu | |
| | | 175 | | | | | 180 | | | | | 185 | | | | |
| ctg | gcc | agg | ttg | ttc | tgt | ggc | gct | ggg | cag | atg | aag | ctt | acc | aga | ttt | 748 |
| Leu | Ala | Arg | Leu | Phe | Cys | Gly | Ala | Gly | Gln | Met | Lys | Leu | Thr | Arg | Phe | |
| | | 190 | | | | | 195 | | | | | 200 | | | | |
| cat | gtg | acc | atc | ttg | ctg | acc | ctt | ttg | gtt | ttt | ctc | ctc | tgc | ggg | ttg | 796 |
| His | Val | Thr | Ile | Leu | Leu | Thr | Leu | Leu | Val | Phe | Leu | Leu | Cys | Gly | Leu | |
| 205 | | | | | 210 | | | | | 215 | | | | | 220 | |
| ccc | ttt | gtc | atc | tac | tgc | atc | ctg | tta | ttc | aag | att | aag | gat | gat | ttc | 844 |
| Pro | Phe | Val | Ile | Tyr | Cys | Ile | Leu | Leu | Phe | Lys | Ile | Lys | Asp | Asp | Phe | |
| | | | 225 | | | | | 230 | | | | | 235 | | | |
| cat | gta | tta | gat | gtt | aat | ttt | tat | cta | gca | tta | gaa | gtc | ctg | act | gct | 892 |
| His | Val | Leu | Asp | Val | Asn | Phe | Tyr | Leu | Ala | Leu | Glu | Val | Leu | Thr | Ala | |
| | | | 240 | | | | | 245 | | | | | 250 | | | |
| att | aac | agc | tgt | gcc | aac | ccc | atc | atc | tac | ttc | ttc | gtg | ggc | tct | ttc | 940 |
| Ile | Asn | Ser | Cys | Ala | Asn | Pro | Ile | Ile | Tyr | Phe | Phe | Val | Gly | Ser | Phe | |
| | | 255 | | | | | 260 | | | | | 265 | | | | |
| aga | cat | cag | ttg | aag | cac | cag | acc | ctc | aaa | atg | gtt | ctc | cag | agt | gca | 988 |
| Arg | His | Gln | Leu | Lys | His | Gln | Thr | Leu | Lys | Met | Val | Leu | Gln | Ser | Ala | |
| | 270 | | | | | 275 | | | | | 280 | | | | | |
| ctg | cag | gac | act | cct | gag | aca | gct | gaa | aac | atg | gta | gag | atg | tca | agt | 1036 |
| Leu | Gln | Asp | Thr | Pro | Glu | Thr | Ala | Glu | Asn | Met | Val | Glu | Met | Ser | Ser | |
| 285 | | | | | 290 | | | | | 295 | | | | | 300 | |
| aac | aaa | gca | gag | cct | tgatgaagag | | cctctacctg | | gacctcagag | | gtggctttgg | | | | | 1091 |
| Asn | Lys | Ala | Glu | Pro | | | | | | | | | | | | |
| | | | 305 | | | | | | | | | | | | | | agtgagcact gccctgctgc acttgaccac tgtccactct tctctcagct tactgatttg    1151 acatgcctca gtggtccacc aacaacttca acatctctcc actaacttag ttttctacc    1211 cctcctgaat aaaagcatta atc    1234

<210> SEQ ID NO 4
<211> LENGTH: 305
<212> TYPE: PRT
<213> ORGANISM: Mus musculus

<400> SEQUENCE: 4

| | | | | | | | | | | | | | | |
|---|---|---|---|---|---|---|---|---|---|---|---|---|---|---|
| Met | Asp | Glu | Thr | Leu | Pro | Gly | Ser | Ile | Asn | Ile | Arg | Ile | Leu | Ile | Pro |
| 1 | | | | 5 | | | | | 10 | | | | | 15 | |

| | | | | | | | | | | | | | | |
|---|---|---|---|---|---|---|---|---|---|---|---|---|---|---|
| Lys | Leu | Met | Ile | Ile | Phe | Gly | Leu | Val | Gly | Leu | Met | Gly | Asn | Ala |
| | | | 20 | | | | | 25 | | | | | 30 | |

| | | | | | | | | | | | | | | |
|---|---|---|---|---|---|---|---|---|---|---|---|---|---|---|
| Ile | Val | Phe | Trp | Leu | Leu | Gly | Phe | His | Leu | Arg | Lys | Asn | Asp | Phe | Ser |
| | | | 35 | | | | | 40 | | | | | 45 | | |

| | | | | | | | | | | | | | | |
|---|---|---|---|---|---|---|---|---|---|---|---|---|---|---|
| Leu | Tyr | Ile | Leu | Asn | Leu | Ala | Arg | Ala | Asp | Phe | Leu | Phe | Leu | Leu | Ser |
| | 50 | | | | | 55 | | | | | 60 | | | | |

| | | | | | | | | | | | | | | |
|---|---|---|---|---|---|---|---|---|---|---|---|---|---|---|
| Ser | Ile | Ile | Ala | Ser | Thr | Leu | Phe | Leu | Leu | Lys | Val | Ser | Tyr | Leu | Ser |
| 65 | | | | | 70 | | | | | 75 | | | | | 80 |

| | | | | | | | | | | | | | | |
|---|---|---|---|---|---|---|---|---|---|---|---|---|---|---|
| Ile | Ile | Phe | His | Leu | Cys | Phe | Asn | Thr | Ile | Met | Met | Val | Val | Tyr | Ile |
| | | | | 85 | | | | | 90 | | | | | 95 | |

| | | | | | | | | | | | | |
|---|---|---|---|---|---|---|---|---|---|---|---|---|
| Thr | Gly | Ile | Ser | Met | Leu | Ser | Ala | Ile | Ser | Thr | Glu | Cys | Cys | Leu | Ser |
| | | | 100 | | | | | 105 | | | | | 110 | | |

-continued

```
Val Leu Cys Pro Thr Trp Tyr Arg Cys His Arg Pro Val His Thr Ser
        115                 120                 125
Thr Val Met Cys Ala Val Ile Trp Val Leu Ser Leu Leu Ile Cys Ile
130                 135                 140
Leu Asn Ser Tyr Phe Cys Ala Val Leu His Thr Arg Tyr Asp Asn Asp
145                 150                 155                 160
Asn Glu Cys Leu Ala Thr Asn Ile Phe Thr Ala Ser Tyr Met Ile Phe
                165                 170                 175
Leu Leu Val Val Leu Cys Leu Ser Ser Leu Ala Leu Leu Ala Arg Leu
                180                 185                 190
Phe Cys Gly Ala Gly Gln Met Lys Leu Thr Arg Phe His Val Thr Ile
        195                 200                 205
Leu Leu Thr Leu Leu Val Phe Leu Leu Cys Gly Leu Pro Phe Val Ile
        210                 215                 220
Tyr Cys Ile Leu Leu Phe Lys Ile Lys Asp Asp Phe His Val Leu Asp
225                 230                 235                 240
Val Asn Phe Tyr Leu Ala Leu Glu Val Leu Thr Ala Ile Asn Ser Cys
                245                 250                 255
Ala Asn Pro Ile Ile Tyr Phe Phe Val Gly Ser Phe Arg His Gln Leu
                260                 265                 270
Lys His Gln Thr Leu Lys Met Val Leu Gln Ser Ala Leu Gln Asp Thr
        275                 280                 285
Pro Glu Thr Ala Glu Asn Met Val Glu Met Ser Ser Asn Lys Ala Glu
        290                 295                 300
Pro
305

<210> SEQ ID NO 5
<211> LENGTH: 1312
<212> TYPE: DNA
<213> ORGANISM: Mus musculus
<220> FEATURE:
<221> NAME/KEY: CDS
<222> LOCATION: (84)..(1070)
<223> OTHER INFORMATION: Mrg5

<400> SEQUENCE: 5
cgcggccgcg tcgacaagaa atattctgta gtgactgtat ccttccttct acacaagcca      60
gcaagctaca tccagcaaga gga atg gga gaa agc aac acc agt gca ggg ttt     113
                         Met Gly Glu Ser Asn Thr Ser Ala Gly Phe
                           1               5                  10 ctg gcc cga aac acc tca gcc tcg aca atg aca ccc aca aca aca aat     161
Leu Ala Arg Asn Thr Ser Ala Ser Thr Met Thr Pro Thr Thr Thr Asn
                15                  20                  25 tca atg aac gaa acc atc cct gga agt att gac atc gag acc ctg atc     209
Ser Met Asn Glu Thr Ile Pro Gly Ser Ile Asp Ile Glu Thr Leu Ile
            30                  35                  40 cca gac ttg atg atc atc atc ttc gga ctg gtc ggg ctg aca gga aat     257
Pro Asp Leu Met Ile Ile Ile Phe Gly Leu Val Gly Leu Thr Gly Asn
        45                  50                  55 gcg att gtg ttc tgg ctc ctt ggc ttc cgc atg cac agg act gcc ttc     305
Ala Ile Val Phe Trp Leu Leu Gly Phe Arg Met His Arg Thr Ala Phe
    60                  65                  70 tta gtc tac atc cta aac ttg gcc ctg gct gac ttc ctc ttc ctt ctc     353
Leu Val Tyr Ile Leu Asn Leu Ala Leu Ala Asp Phe Leu Phe Leu Leu
75                  80                  85                  90 tgt cac atc ata aat tcc aca gtg gat ctt ctc aag ttt acc cta ccc     401
Cys His Ile Ile Asn Ser Thr Val Asp Leu Leu Lys Phe Thr Leu Pro
```

```
                      95                  100                 105
aaa gga att ttt gcc ttt tgt ttt cac act atc aaa agg gtt ctc tat         449
Lys Gly Ile Phe Ala Phe Cys Phe His Thr Ile Lys Arg Val Leu Tyr
            110                 115                 120 atc aca ggc ctg agc atg ctc agt gcc atc agc act gag cgc tgc ctg         497
Ile Thr Gly Leu Ser Met Leu Ser Ala Ile Ser Thr Glu Arg Cys Leu
        125                 130                 135 tct gtc ctg tgc ccc atc tgg tat cac tgc cgc cgc cca gaa cac aca         545
Ser Val Leu Cys Pro Ile Trp Tyr His Cys Arg Arg Pro Glu His Thr
    140                 145                 150 tca act gtc atg tgt gct gtg atc tgg gtc ctg tcc ctg ttg atc tgc         593
Ser Thr Val Met Cys Ala Val Ile Trp Val Leu Ser Leu Leu Ile Cys
155                 160                 165                 170 att ctg gat ggt tat ttc tgc ggt tac tta gat aac cat tat ttc aat         641
Ile Leu Asp Gly Tyr Phe Cys Gly Tyr Leu Asp Asn His Tyr Phe Asn
                175                 180                 185 tac tct gtg tgt cag gca tgg gac atc ttt atc gga gca tac ctg atg         689
Tyr Ser Val Cys Gln Ala Trp Asp Ile Phe Ile Gly Ala Tyr Leu Met
            190                 195                 200 ttt ttg ttt gta gtc ctc tgt ctg tcc acc ctg gct cta ctg gcc agg         737
Phe Leu Phe Val Val Leu Cys Leu Ser Thr Leu Ala Leu Leu Ala Arg
        205                 210                 215 ttg ttc tgt ggt gct agg aat atg aaa ttt acc aga tta ttc gtg acc         785
Leu Phe Cys Gly Ala Arg Asn Met Lys Phe Thr Arg Leu Phe Val Thr
    220                 225                 230 atc atg ctg acc gtt ttg gtt ttt ctt ctc tgt ggg ttg ccc tgg ggc         833
Ile Met Leu Thr Val Leu Val Phe Leu Leu Cys Gly Leu Pro Trp Gly
235                 240                 245                 250 atc acc tgg ttc ctg tta ttc tgg att gca cct ggt gtg ttt gta cta         881
Ile Thr Trp Phe Leu Leu Phe Trp Ile Ala Pro Gly Val Phe Val Leu
                255                 260                 265 gat tat agc cct ctt ctg gtc cta act gct att aac agc tgt gcc aac         929
Asp Tyr Ser Pro Leu Leu Val Leu Thr Ala Ile Asn Ser Cys Ala Asn
            270                 275                 280 ccc att att tac ttc ttc gtg ggc tcc ttc agg caa cgg ttg aat aaa         977
Pro Ile Ile Tyr Phe Phe Val Gly Ser Phe Arg Gln Arg Leu Asn Lys
        285                 290                 295 cag acc ctc aaa atg gtt ctc cag aaa gcc ctg cag gac act cct gag         1025
Gln Thr Leu Lys Met Val Leu Gln Lys Ala Leu Gln Asp Thr Pro Glu
    300                 305                 310 aca cct gaa aac atg gtg gag atg tca aga aac aaa gca gag ccg             1070
Thr Pro Glu Asn Met Val Glu Met Ser Arg Asn Lys Ala Glu Pro
315                 320                 325 tgatgaagag cctctgccta gacttcagag gtggatttgg agtgagcact gccctgctgc       1130
acttgaccac tgtccactct cctctcagct tactgacttg acatgcctca ctggtccacc       1190
aacaccttcc aaagctctcc actgacttag tatttatacc tctcccaaac aatagcatta       1250
ttcaaaaact ataatttctg catccttctt tacattaata aaattcccat actaagttca       1310
aa                                                                      1312

<210> SEQ ID NO 6
<211> LENGTH: 329
<212> TYPE: PRT
<213> ORGANISM: Mus musculus

<400> SEQUENCE: 6

Met Gly Glu Ser Asn Thr Ser Ala Gly Phe Leu Ala Arg Asn Thr Ser
 1               5                  10                  15
```

-continued

```
Ala Ser Thr Met Thr Pro Thr Thr Asn Ser Met Asn Glu Thr Ile
            20                  25                  30

Pro Gly Ser Ile Asp Ile Glu Thr Leu Ile Pro Asp Leu Met Ile Ile
        35                  40                  45

Ile Phe Gly Leu Val Gly Leu Thr Gly Asn Ala Ile Val Phe Trp Leu
 50                  55                  60

Leu Gly Phe Arg Met His Arg Thr Ala Phe Leu Val Tyr Ile Leu Asn
 65                  70                  75                  80

Leu Ala Leu Ala Asp Phe Leu Phe Leu Leu Cys His Ile Ile Asn Ser
                85                  90                  95

Thr Val Asp Leu Leu Lys Phe Thr Leu Pro Lys Gly Ile Phe Ala Phe
            100                 105                 110

Cys Phe His Thr Ile Lys Arg Val Leu Tyr Ile Thr Gly Leu Ser Met
            115                 120                 125

Leu Ser Ala Ile Ser Thr Glu Arg Cys Leu Ser Val Leu Cys Pro Ile
130                 135                 140

Trp Tyr His Cys Arg Arg Pro Glu His Thr Ser Thr Val Met Cys Ala
145                 150                 155                 160

Val Ile Trp Val Leu Ser Leu Leu Ile Cys Ile Leu Asp Gly Tyr Phe
                165                 170                 175

Cys Gly Tyr Leu Asp Asn His Tyr Phe Asn Tyr Ser Val Cys Gln Ala
            180                 185                 190

Trp Asp Ile Phe Ile Gly Ala Tyr Leu Met Phe Leu Phe Val Val Leu
        195                 200                 205

Cys Leu Ser Thr Leu Ala Leu Leu Ala Arg Leu Phe Cys Gly Ala Arg
210                 215                 220

Asn Met Lys Phe Thr Arg Leu Phe Val Thr Ile Met Leu Thr Val Leu
225                 230                 235                 240

Val Phe Leu Leu Cys Gly Leu Pro Trp Gly Ile Thr Trp Phe Leu Leu
                245                 250                 255

Phe Trp Ile Ala Pro Gly Val Phe Val Leu Asp Tyr Ser Pro Leu Leu
            260                 265                 270

Val Leu Thr Ala Ile Asn Ser Cys Ala Asn Pro Ile Ile Tyr Phe Phe
        275                 280                 285

Val Gly Ser Phe Arg Gln Arg Leu Asn Lys Gln Thr Leu Lys Met Val
    290                 295                 300

Leu Gln Lys Ala Leu Gln Asp Thr Pro Glu Thr Pro Glu Asn Met Val
305                 310                 315                 320

Glu Met Ser Arg Asn Lys Ala Glu Pro
                325
```

<210> SEQ ID NO 7
<211> LENGTH: 450
<212> TYPE: DNA
<213> ORGANISM: Mus musculus
<220> FEATURE:
<221> NAME/KEY: CDS
<222> LOCATION: (1)..(450)
<223> OTHER INFORMATION: Mrg6

<400> SEQUENCE: 7

```
ctg tgc cgg atc tgg tat cac tgc cgc cgc cca gaa cac aca tca act    48
Leu Cys Arg Ile Trp Tyr His Cys Arg Arg Pro Glu His Thr Ser Thr
 1               5                  10                  15 gtc atg tgt gct gtc atc tgg gtc ctg tcc ctg ttg atc tgc att ctg    96
Val Met Cys Ala Val Ile Trp Val Leu Ser Leu Leu Ile Cys Ile Leu
            20                  25                  30
```

```
aat agt tat ttc tgc ggt ttc tta aat acc caa tat aaa aat gaa aat    144
Asn Ser Tyr Phe Cys Gly Phe Leu Asn Thr Gln Tyr Lys Asn Glu Asn
        35                  40                  45 ggg tgt ctg gca ttg agc ttc ttt act gct gca tac ctg atg ttt ttg    192
Gly Cys Leu Ala Leu Ser Phe Phe Thr Ala Ala Tyr Leu Met Phe Leu
 50                  55                  60 ttt gtg gtc ctc tgt ctg tcc agc ctg gct ctg gtg gcc agg ttg ttc    240
Phe Val Val Leu Cys Leu Ser Ser Leu Ala Leu Val Ala Arg Leu Phe
 65                  70                  75                  80 tgt ggt gct agg aat atg aaa ttt acc aga tta ttc gtg acc atc atg    288
Cys Gly Ala Arg Asn Met Lys Phe Thr Arg Leu Phe Val Thr Ile Met
                 85                  90                  95 ctg acc gtt ttg gtt ttt ctt ctc tgt ggg ttg ccc tgg ggc atc acc    336
Leu Thr Val Leu Val Phe Leu Leu Cys Gly Leu Pro Trp Gly Ile Thr
            100                 105                 110 tgg ttc ctg tta ttc tgg att gca cct ggt gtg ttt gta cta gat tat    384
Trp Phe Leu Leu Phe Trp Ile Ala Pro Gly Val Phe Val Leu Asp Tyr
        115                 120                 125 agc cct ctt ctg gtc cta act gct att aac agc tgt gcc aac ccc att    432
Ser Pro Leu Leu Val Leu Thr Ala Ile Asn Ser Cys Ala Asn Pro Ile
130                 135                 140 att tac ttc ttc gtc ggc                                            450
Ile Tyr Phe Phe Val Gly
145                 150

<210> SEQ ID NO 8
<211> LENGTH: 150
<212> TYPE: PRT
<213> ORGANISM: Mus musculus

<400> SEQUENCE: 8

Leu Cys Arg Ile Trp Tyr His Cys Arg Arg Pro Glu His Thr Ser Thr
 1               5                  10                  15

Val Met Cys Ala Val Ile Trp Val Leu Ser Leu Leu Ile Cys Ile Leu
             20                  25                  30

Asn Ser Tyr Phe Cys Gly Phe Leu Asn Thr Gln Tyr Lys Asn Glu Asn
        35                  40                  45

Gly Cys Leu Ala Leu Ser Phe Phe Thr Ala Ala Tyr Leu Met Phe Leu
 50                  55                  60

Phe Val Val Leu Cys Leu Ser Ser Leu Ala Leu Val Ala Arg Leu Phe
 65                  70                  75                  80

Cys Gly Ala Arg Asn Met Lys Phe Thr Arg Leu Phe Val Thr Ile Met
                 85                  90                  95

Leu Thr Val Leu Val Phe Leu Leu Cys Gly Leu Pro Trp Gly Ile Thr
            100                 105                 110

Trp Phe Leu Leu Phe Trp Ile Ala Pro Gly Val Phe Val Leu Asp Tyr
        115                 120                 125

Ser Pro Leu Leu Val Leu Thr Ala Ile Asn Ser Cys Ala Asn Pro Ile
130                 135                 140

Ile Tyr Phe Phe Val Gly
145                 150

<210> SEQ ID NO 9
<211> LENGTH: 459
<212> TYPE: DNA
<213> ORGANISM: Mus musculus
<220> FEATURE:
<221> NAME/KEY: CDS
<222> LOCATION: (1)..(459)
```

<223> OTHER INFORMATION: Mrg7

<400> SEQUENCE: 9

```
ctg tgc ccg acg tgg tat cgc tgc cac cgt cca gta cat aca tca act        48
Leu Cys Pro Thr Trp Tyr Arg Cys His Arg Pro Val His Thr Ser Thr
  1               5                  10                  15 gtc atg tgt gct gtg atc tgg gtc cta tcc ctg ttg atc tgc att ctg        96
Val Met Cys Ala Val Ile Trp Val Leu Ser Leu Leu Ile Cys Ile Leu
             20                  25                  30 aat agc tat ttc tgt gct gtc tta cat acc aga tat gat aat gac aat       144
Asn Ser Tyr Phe Cys Ala Val Leu His Thr Arg Tyr Asp Asn Asp Asn
         35                  40                  45 gag tgt ctg gca act aac atc ttt acc gcc tcg tac atg ata ttt ttg       192
Glu Cys Leu Ala Thr Asn Ile Phe Thr Ala Ser Tyr Met Ile Phe Leu
     50                  55                  60 ctt gtg gtc ctc tgt ctg tcc agc ctg gct ctg ctg gcc agg ttg ttc       240
Leu Val Val Leu Cys Leu Ser Ser Leu Ala Leu Leu Ala Arg Leu Phe
 65                  70                  75                  80 tgt ggc gct ggg cag atg aag ctt acc aga ttt cat gtg acc atc ttg       288
Cys Gly Ala Gly Gln Met Lys Leu Thr Arg Phe His Val Thr Ile Leu
                 85                  90                  95 ctg acc ctt ttg gtt ttt ctc ctc tgc ggg ttg ccc ttt gtc atc tac       336
Leu Thr Leu Leu Val Phe Leu Leu Cys Gly Leu Pro Phe Val Ile Tyr
            100                 105                 110 tgc atc ctg tta ttc aag att aag gat gat ttc cat gta tta gat gtt       384
Cys Ile Leu Leu Phe Lys Ile Lys Asp Asp Phe His Val Leu Asp Val
        115                 120                 125 aat ctt tat cta gca tta gaa gtc ctg act gct att aac agc tgt gcc       432
Asn Leu Tyr Leu Ala Leu Glu Val Leu Thr Ala Ile Asn Ser Cys Ala
    130                 135                 140 aac ccc atc atc tac ttc ttc gtc gga                                   459
Asn Pro Ile Ile Tyr Phe Phe Val Gly
145                 150
```

<210> SEQ ID NO 10
<211> LENGTH: 153
<212> TYPE: PRT
<213> ORGANISM: Mus musculus

<400> SEQUENCE: 10

```
Leu Cys Pro Thr Trp Tyr Arg Cys His Arg Pro Val His Thr Ser Thr
  1               5                  10                  15

Val Met Cys Ala Val Ile Trp Val Leu Ser Leu Leu Ile Cys Ile Leu
             20                  25                  30

Asn Ser Tyr Phe Cys Ala Val Leu His Thr Arg Tyr Asp Asn Asp Asn
         35                  40                  45

Glu Cys Leu Ala Thr Asn Ile Phe Thr Ala Ser Tyr Met Ile Phe Leu
     50                  55                  60

Leu Val Val Leu Cys Leu Ser Ser Leu Ala Leu Leu Ala Arg Leu Phe
 65                  70                  75                  80

Cys Gly Ala Gly Gln Met Lys Leu Thr Arg Phe His Val Thr Ile Leu
                 85                  90                  95

Leu Thr Leu Leu Val Phe Leu Leu Cys Gly Leu Pro Phe Val Ile Tyr
            100                 105                 110

Cys Ile Leu Leu Phe Lys Ile Lys Asp Asp Phe His Val Leu Asp Val
        115                 120                 125

Asn Leu Tyr Leu Ala Leu Glu Val Leu Thr Ala Ile Asn Ser Cys Ala
    130                 135                 140
```

```
Asn Pro Ile Ile Tyr Phe Phe Val Gly
145                 150

<210> SEQ ID NO 11
<211> LENGTH: 2853
<212> TYPE: DNA
<213> ORGANISM: Mus musculus
<220> FEATURE:
<221> NAME/KEY: CDS
<222> LOCATION: (1796)..(2734)
<223> OTHER INFORMATION: Mrg8

<400> SEQUENCE: 11
caaggattct acaaacccaa gtatgcaagt caacaatcta aatataattt gttccttttg    60
aagttagtgg ttcaatataa cagacaaata catcatgccc tgaaattagc tttgaacaat   120
gctaagccca taatgggaag taaaagattt gcttggttcc cactttcttc cttttctatt   180
ccgtttggac catagtggct agtgtctctt acaagatcac aagaaggagg ctctgcattt   240
atttctgagt gcctgtctgc atcctccttt ggcctggagg tcctctatga aatcctgaag   300
taagaaagaa atgttccaga ctctgatttt tcttcctaga ccaatgctat tcccttccat   360
gttgccaaca acttctcatc actctttctg tactttcttt tagctgggtg gtttcttaat   420
ctacagtatt gactgtcatg tcaaagttgg gtattttttg gctttagata tttcttctct   480
ggcttttctc ccatccacac ataatcaaaa cactgaggtg atgacactaa gggactgctc   540
aaaggaaaag ggtgggttcc tgggctttgg ggttattaat aatttgcctg tcctctgcca   600
gcctctatca actcccctaa aacacaaaaa taattgttcc tagcaggcaa gcacgacctg   660
acaattaatt aatgatcata aaaagtgcat tataaacatc tgaaaccctc ataataaaac   720
tcaacacctt atacagtgag tatgttgtgg ggtctgcata aatccaacaa aactccaatg   780
gagtggtact cagctattaa aaatgaggaa ttcacgaaat tcttagccaa atgattagaa   840
gtagaaaata tgatcctgag tgagaaaaga acaggcttgg tatgtactca ctgataagtg   900
gatactagcc caaaagctgc aaataatcag gataaaattc acagaccaca tgaacctcaa   960
taagaaggaa gaccaaagta tgggcgtttc ggtccttctt agaaggagaa caaaatactc  1020
ccaagagcaa atatggagat aaagtgtaga acaggcacta aggaaaagt cacccagaga  1080
atgttccacc tggggattca tcccatatac agttaccaaa cccagacact cttatggatg  1140
ccaaggagtg aatgctgaca tagctgtttc ctaagaggcc atgccagaca cttacaaata  1200
cagaggccca agttagcaac caaccattag actgagcaca gggttcctaa tagaggagtc  1260
agagaaagga ctgagggagt tgaaggggtt tgcatcccca taagaaaaac aacaacatga  1320
accaacaaga cactctcccc accaaccccc tgaactccta gggactaagc catcaacaaa  1380
agagtacaca tggctccaga tgcatatgtt gcagaggatg ccatatcat gcattgatgg  1440
aagaggtcct tgaacctatg aaggttctat tgatgcccca gtgtaaggga atcgagggca  1500
gagaggtgga agtgggtgtg tgggttgagc aacaccctca cagaagcagg gggagggagg  1560
atgagatggg ggtttccagg aaggggggaa gcaggaaagg ggataacatt ttaaatttaa  1620
atatagaaaa tatccaatac aaaacatttt gaacaaacaa caaaaaactc acaaaaacaa  1680
caacaacaaa aaaagaaat taaaagttgt gttcatagtg aaggcctcat ttcttctttg  1740
tgttcccagc aacaccagtg cagggttcct ggccctaaac acctcagcct cggca atg   1798
                                                              Met
                                                                1 gca ccc aca aca aca aat cca atg aac gaa acc atc cct gga agt att  1846
Ala Pro Thr Thr Thr Asn Pro Met Asn Glu Thr Ile Pro Gly Ser Ile
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 5   |     |     |     | 10  |     |     |     | 15  |     |     |     |     |     |      |
| gac | atc | gag | acc | ctg | atc | cca | aac | ttg | atg | atc | atc | atc | ttc | gga | ctg | 1894 |
| Asp | Ile | Glu | Thr | Leu | Ile | Pro | Asn | Leu | Met | Ile | Ile | Ile | Phe | Gly | Leu |      |
|     |     | 20  |     |     |     | 25  |     |     |     | 30  |     |     |     |     |     |      |
| gtc | ggg | ctg | aca | gga | aat | gtc | att | ttg | ttt | tgg | ctc | ctg | ggc | ttc | cac | 1942 |
| Val | Gly | Leu | Thr | Gly | Asn | Val | Ile | Leu | Phe | Trp | Leu | Leu | Gly | Phe | His |      |
| 35  |     |     |     |     | 40  |     |     |     |     | 45  |     |     |     |     |     |      |
| ttg | cac | agg | aat | gcc | ttc | tta | gtc | tac | atc | cta | aac | ttg | gcc | ctg | gct | 1990 |
| Leu | His | Arg | Asn | Ala | Phe | Leu | Val | Tyr | Ile | Leu | Asn | Leu | Ala | Leu | Ala |      |
| 50  |     |     |     | 55  |     |     |     |     | 60  |     |     |     |     | 65  |     |      |
| gac | ttc | ctc | ttc | ctt | ctc | tgt | cac | atc | ata | aat | tcc | aca | atg | ctt | ctt | 2038 |
| Asp | Phe | Leu | Phe | Leu | Leu | Cys | His | Ile | Ile | Asn | Ser | Thr | Met | Leu | Leu |      |
|     |     |     | 70  |     |     |     |     | 75  |     |     |     |     | 80  |     |     |      |
| ctc | aag | gtt | cac | cta | ccc | aac | aat | att | ttg | aac | cat | tgc | ttt | gac | atc | 2086 |
| Leu | Lys | Val | His | Leu | Pro | Asn | Asn | Ile | Leu | Asn | His | Cys | Phe | Asp | Ile |      |
|     |     |     |     | 85  |     |     |     |     | 90  |     |     |     |     | 95  |     |      |
| atc | atg | aca | gtt | ctc | tac | atc | aca | ggc | ctg | agc | atg | ctc | agt | gcc | atc | 2134 |
| Ile | Met | Thr | Val | Leu | Tyr | Ile | Thr | Gly | Leu | Ser | Met | Leu | Ser | Ala | Ile |      |
|     |     |     | 100 |     |     |     |     | 105 |     |     |     |     | 110 |     |     |      |
| agc | act | gag | cgc | tgc | ctg | tct | gtc | ctg | tgc | ccc | atc | tgg | tat | cgg | tgc | 2182 |
| Ser | Thr | Glu | Arg | Cys | Leu | Ser | Val | Leu | Cys | Pro | Ile | Trp | Tyr | Arg | Cys |      |
| 115 |     |     |     |     | 120 |     |     |     |     | 125 |     |     |     |     |     |      |
| cgc | cgc | cca | gaa | cac | aca | tca | act | gtc | ctg | tgt | gct | gtg | atc | tgg | ttc | 2230 |
| Arg | Arg | Pro | Glu | His | Thr | Ser | Thr | Val | Leu | Cys | Ala | Val | Ile | Trp | Phe |      |
| 130 |     |     |     |     | 135 |     |     |     |     | 140 |     |     |     |     | 145 |      |
| ctg | ccc | ctg | ttg | atc | tgc | att | ctg | aat | gga | tat | ttc | tgt | cat | ttc | ttt | 2278 |
| Leu | Pro | Leu | Leu | Ile | Cys | Ile | Leu | Asn | Gly | Tyr | Phe | Cys | His | Phe | Phe |      |
|     |     |     |     | 150 |     |     |     |     | 155 |     |     |     |     | 160 |     |      |
| ggt | ccc | aaa | tat | gta | att | gac | tct | gtg | tgt | ctg | gca | acg | aac | ttc | ttt | 2326 |
| Gly | Pro | Lys | Tyr | Val | Ile | Asp | Ser | Val | Cys | Leu | Ala | Thr | Asn | Phe | Phe |      |
|     |     | 165 |     |     |     |     | 170 |     |     |     |     | 175 |     |     |     |      |
| atc | aga | aca | tac | ccg | atg | ttt | ttg | ttt | ata | gtc | ctc | tgt | ctg | tcc | acc | 2374 |
| Ile | Arg | Thr | Tyr | Pro | Met | Phe | Leu | Phe | Ile | Val | Leu | Cys | Leu | Ser | Thr |      |
|     |     | 180 |     |     |     |     | 185 |     |     |     |     | 190 |     |     |     |      |
| ctg | gct | ctg | ctg | gcc | agg | ttg | ttc | tgt | ggt | ggt | ggg | aag | acg | aaa | ttt | 2422 |
| Leu | Ala | Leu | Leu | Ala | Arg | Leu | Phe | Cys | Gly | Gly | Gly | Lys | Thr | Lys | Phe |      |
| 195 |     |     |     |     | 200 |     |     |     |     | 205 |     |     |     |     |     |      |
| acc | aga | tta | ttc | gtg | acc | atc | atg | ctg | acc | gtt | tgt | gtt | ttt | ctt | ctc | 2470 |
| Thr | Arg | Leu | Phe | Val | Thr | Ile | Met | Leu | Thr | Val | Leu | Val | Phe | Leu | Leu |      |
| 210 |     |     |     |     | 215 |     |     |     |     | 220 |     |     |     |     | 225 |      |
| tgt | ggg | ttg | ccc | ctg | ggc | ttc | ttc | tgg | ttt | ctg | gtg | ccg | tgg | att | aac | 2518 |
| Cys | Gly | Leu | Pro | Leu | Gly | Phe | Phe | Trp | Phe | Leu | Val | Pro | Trp | Ile | Asn |      |
|     |     |     |     | 230 |     |     |     |     | 235 |     |     |     |     | 240 |     |      |
| cgt | gat | ttc | agt | gta | cta | gat | tat | ata | ctt | ttt | cag | aca | tca | ctt | gtc | 2566 |
| Arg | Asp | Phe | Ser | Val | Leu | Asp | Tyr | Ile | Leu | Phe | Gln | Thr | Ser | Leu | Val |      |
|     |     |     | 245 |     |     |     |     | 250 |     |     |     |     | 255 |     |     |      |
| cta | act | tct | gtt | aac | agc | tgt | gcc | aac | ccc | atc | att | tac | ttc | ttt | gtg | 2614 |
| Leu | Thr | Ser | Val | Asn | Ser | Cys | Ala | Asn | Pro | Ile | Ile | Tyr | Phe | Phe | Val |      |
|     | 260 |     |     |     |     | 265 |     |     |     |     | 270 |     |     |     |     |      |
| ggc | tcc | ttc | agg | cat | cgg | ttg | aag | cac | aag | acc | ctc | aaa | atg | gtt | ctc | 2662 |
| Gly | Ser | Phe | Arg | His | Arg | Leu | Lys | His | Lys | Thr | Leu | Lys | Met | Val | Leu |      |
|     | 275 |     |     |     |     | 280 |     |     |     |     | 285 |     |     |     |     |      |
| cag | agt | gca | ttg | cag | gac | act | cct | gag | aca | cct | gaa | aac | atg | gtg | gag | 2710 |
| Gln | Ser | Ala | Leu | Gln | Asp | Thr | Pro | Glu | Thr | Pro | Glu | Asn | Met | Val | Glu |      |
| 290 |     |     |     |     | 295 |     |     |     |     | 300 |     |     |     |     | 305 |      |
| atg | tca | aga | agc | aaa | gca | gag | ccg | tgatgaagag | | | | cctctacctg | | gacctcagag | | 2764 |
| Met | Ser | Arg | Ser | Lys | Ala | Glu | Pro |     |     |     |     |     |     |     |     |      |
|     |     |     |     | 310 |     |     |     |     |     |     |     |     |     |     |     |      | gtggctttgg attgagcact gccctgctgc acttgaccac tgtccactct cctctcagct 2824

-continued

```
tactgactttt ggatgcctca gtggtccaa                                              2853
```

<210> SEQ ID NO 12
<211> LENGTH: 313
<212> TYPE: PRT
<213> ORGANISM: Mus musculus

<400> SEQUENCE: 12

```
Met Ala Pro Thr Thr Thr Asn Pro Met Asn Glu Thr Ile Pro Gly Ser
 1               5                  10                  15

Ile Asp Ile Glu Thr Leu Ile Pro Asn Leu Met Ile Ile Phe Gly
            20                  25                  30

Leu Val Gly Leu Thr Gly Asn Val Ile Leu Phe Trp Leu Leu Gly Phe
        35                  40                  45

His Leu His Arg Asn Ala Phe Leu Val Tyr Ile Leu Asn Leu Ala Leu
    50                  55                  60

Ala Asp Phe Leu Phe Leu Cys His Ile Ile Asn Ser Thr Met Leu
 65                  70                  75                  80

Leu Leu Lys Val His Leu Pro Asn Asn Ile Leu Asn His Cys Phe Asp
                85                  90                  95

Ile Ile Met Thr Val Leu Tyr Ile Thr Gly Leu Ser Met Leu Ser Ala
            100                 105                 110

Ile Ser Thr Glu Arg Cys Leu Ser Val Leu Cys Pro Ile Trp Tyr Arg
        115                 120                 125

Cys Arg Arg Pro Glu His Thr Ser Thr Val Leu Cys Ala Val Ile Trp
    130                 135                 140

Phe Leu Pro Leu Leu Ile Cys Ile Leu Asn Gly Tyr Phe Cys His Phe
145                 150                 155                 160

Phe Gly Pro Lys Tyr Val Ile Asp Ser Val Cys Leu Ala Thr Asn Phe
                165                 170                 175

Phe Ile Arg Thr Tyr Pro Met Phe Leu Phe Ile Val Leu Cys Leu Ser
            180                 185                 190

Thr Leu Ala Leu Leu Ala Arg Leu Phe Cys Gly Gly Gly Lys Thr Lys
        195                 200                 205

Phe Thr Arg Leu Phe Val Thr Ile Met Leu Thr Val Leu Val Phe Leu
    210                 215                 220

Leu Cys Gly Leu Pro Leu Gly Phe Phe Trp Phe Leu Val Pro Trp Ile
225                 230                 235                 240

Asn Arg Asp Phe Ser Val Leu Asp Tyr Ile Leu Phe Gln Thr Ser Leu
                245                 250                 255

Val Leu Thr Ser Val Asn Ser Cys Ala Asn Pro Ile Ile Tyr Phe Phe
            260                 265                 270

Val Gly Ser Phe Arg His Arg Leu Lys His Lys Thr Leu Lys Met Val
        275                 280                 285

Leu Gln Ser Ala Leu Gln Asp Thr Pro Glu Thr Pro Glu Asn Met Val
    290                 295                 300

Glu Met Ser Arg Ser Lys Ala Glu Pro
305                 310
```

<210> SEQ ID NO 13
<211> LENGTH: 3391
<212> TYPE: DNA
<213> ORGANISM: Mus musculus
<220> FEATURE:
<221> NAME/KEY: CDS
<222> LOCATION: (170)..(574)

<223> OTHER INFORMATION: drg12

<400> SEQUENCE: 13

```
ccgaaaacca acaaaataga accgcgggtg cctttctcca gctgggatga aggacttgag      60
cagaaactca ttgccagctt cctccctacg cgagagccga ctgagtccca ggtccccagt     120
cttcccccgg gacgttgtgc acggtgccca ttcttgagca gccacaaca atg gag gtg     178
                                                        Met Glu Val
                                                          1 ctc ccc aag gcc ctg gag gta gac gag agg tct cca gag tcc aag gac       226
Leu Pro Lys Ala Leu Glu Val Asp Glu Arg Ser Pro Glu Ser Lys Asp
      5                  10                  15 ctg ctg ccc agc cag aca gcc agc tcc ctg tgc atc agt tcc aga agt       274
Leu Leu Pro Ser Gln Thr Ala Ser Ser Leu Cys Ile Ser Ser Arg Ser
 20                  25                  30                  35 gag tct gtc tgg acc acc aca ccc aaa agc aac tgg gaa atc tac cac       322
Glu Ser Val Trp Thr Thr Thr Pro Lys Ser Asn Trp Glu Ile Tyr His
                 40                  45                  50 aag ccc atc atc atc atg tca gtg gga gct gcc att ctg ctc ttt ggc       370
Lys Pro Ile Ile Ile Met Ser Val Gly Ala Ala Ile Leu Leu Phe Gly
             55                  60                  65 gtg gcc atc acc tgt gtg gcc tac atc ttg gaa gag aag cat aaa gtt       418
Val Ala Ile Thr Cys Val Ala Tyr Ile Leu Glu Glu Lys His Lys Val
         70                  75                  80 gtg caa gtg ctc agg atg ata ggg cct gcc ttc ctg tcc ctg gga ctc       466
Val Gln Val Leu Arg Met Ile Gly Pro Ala Phe Leu Ser Leu Gly Leu
     85                  90                  95 atg atg ctg gtg tgt ggg ctg gtg tgg gtc ccc ata atc aaa aag aag       514
Met Met Leu Val Cys Gly Leu Val Trp Val Pro Ile Ile Lys Lys Lys
100                 105                 110                 115 cag aag caa agg cag aag tcc aac ttc ttc caa agc ctc aag ttc ttc       562
Gln Lys Gln Arg Gln Lys Ser Asn Phe Phe Gln Ser Leu Lys Phe Phe
                120                 125                 130 ctc ctg aac cgc tgatgactgg ttgtccagaa gatctgctaa ccaataagca           614
Leu Leu Asn Arg
            135 gcctcctacc ttctcttcgg gtaccacaaa gttgatccag gcaaaccctc ctcttggccc     674 tgtggacagg atagagctca gggcttcacc ctcatacaac ctagcagcat tgctgactga     734 gtctcacctg gtttccatag ctgtggatgc tgtgcccttg gatactttca ttaccctcat     794 ccctggcacc tgcattcagc catcagccat cccattctct ctgccaaggg caatgtgtgc     854 atgctaggaa attctttggg ggttgactac attcccaagg agaacttgta tgttacggtt     914 gtgtgcctga tcttagattc ccatctacat ccttctggaa ccaaaagtga ccaagcagat     974 aaggctgact tcagtcccat tgggtttgac agccttggct ccctccttgg atgggacatt    1034 gactaacatt acaagagaaa ggatatgtct catgtatcac acattccaaa atctggacag    1094 tgatggggct gggggtgagg gaaacactgt ctagagtaaa ccattcctct gggagtaatc    1154 tggaacttat acagtgaagg aagttagctc ctaaatatat gatattggca caagaggcaa    1214 tatgcaggct aagaggtatc aacacttccc cttgatcctc caatgcgctt cttgcagaat    1274 gcctttatat tagcaattag ccaagaacaa atgctctttg ttctaacttc cttccccacc    1334 acatctctgc gtctacacag ctccagaaca gaaggacggg aggccacaga tgtgacctgt    1394 aagatcatct ccttctcctg tcaatcaaga cctaacctga aattgaatgc catgtccgac    1454 tcacgctgca tggggtttta gagataggtt cactggaaaa aaggaaatct cagcctccct    1514 cctccctgtt cctccctacc aaacaagcaa gtatttattg agtttccttc tctaggccta    1574
```

-continued

```
cgttgggaac agccagaccc agtctctgat gtcatcttat ttccaaaagt gaaagaggga    1634
aaaacatggc caagccaact ggcaatactc catactgagt tcttagggtg gccatgggaa    1694
cacatggatc taacaaatgt acaggaagat agatttctgg agaccatgtt cacccccttct   1754 gaatatgaag gggaaggaag tgtttggaat gagcaagatg tgcaaggtag tcagcaactg    1814
ccttgcatgt ggagaagcta aggggaaaga cagggtgg ggttaggatt ccgcatagct      1874
cccggatgct attccatcct ctcttgccta cttccccct gcttcccag gtaccttaca      1934 tccagctact ccttggtaca ctgcaggctt ctggggtcaa tagggactgg gaggggcatc    1994
tccagagggc ctaacaagta gatataaccc aagaggtaag taccctcaaa acttcattat    2054
agtcaccaag acacctttag gcaaaagacc gggcacctat aagaaatttc caaagctgtt    2114
ccaggcaagg ccaggccaga gagcagagga aggtacctag tagcaaagtg aatgacaaga    2174
gctgcattgg ttcaggttga ctcttcatcc ttaacctttg ggcatttggg aacactatgg    2234
caaacaacct ccaacaggtc tccagatatc tcaaccattc acagtacttc tataggcagt    2294
tagaatccac cacctttgtt cctgttgcat tgtgggacat tcctcggagg aagtatttgt    2354
tttgtggaat caacacacac acacacacgc acagagagag agagagagag agagagagag    2414
agagagagag agagagagag agagaaagaa agagaaagaa agaaagaaag agaaagagac    2474
tgactcccta actaaaaagt cagagtttgg gaagcctgtg gcctttcaaa gctcacttaa    2534
gaatatcatg ttcctcatta agactcacat catcgagccc aggccctgca gtccacccat    2594
tccctgaata caggcagctc aggaccaacc ctggggttgt tgaaatactg cctagtgctt    2654
ccacgaatgt ctaatgcctc catgacaggg ctttcagacc actccttct cctgacatgg     2714 aaggacagcc ctggggtgga gcctctcaat cttctgtgcc ttcatgaaag gaacacaca    2774 gatgagctca cagccagctc acttggaatc cgcaccccat gcacctcatt gtcctgagag    2834
ctcattgtct gggcacagct gtgggaagac cttttgcagat ctcactttca agtatgtctc   2894
aacagaaggg agtttgggga taatcacgat gccaggaaat cttcaagttc tagacatctt    2954
tcatagccac atcagtacct gttccccaac ccctgcccct caaggtaagt acttagcaaa    3014
caaaatcaaa gagcctttga gaaaatatcc caaatactgg ttaactcccc cggccttgca    3074
ccaaactccc cacaaaagtg atagtcagga agtgagcaga gtcacaccca acatcttgga    3134
aaattttgcc aaagaccatt gcctcatgaa aactgggtg gggataacct gtgagtgcag     3194
ccgggttgga tgccgtgtct ctgcaacaaa gcattctggg tagtgatttc agtcatctca    3254
gaagacaaga gcaacatcca cagcaccatc ccaccggact gtattacggg cttctgtcgc    3314
tcttctgttt tggagaattt aatctaaccc aacgcctaat ggaatcaatg tcgtattgaa    3374
ctgtattctg tttaaaa                                                   3391
```

<210> SEQ ID NO 14
<211> LENGTH: 135
<212> TYPE: PRT
<213> ORGANISM: Mus musculus

<400> SEQUENCE: 14

```
Met Glu Val Leu Pro Lys Ala Leu Glu Val Asp Glu Arg Ser Pro Glu
 1               5                  10                  15

Ser Lys Asp Leu Leu Pro Ser Gln Thr Ala Ser Ser Leu Cys Ile Ser
            20                  25                  30

Ser Arg Ser Glu Ser Val Trp Thr Thr Pro Lys Ser Asn Trp Glu
        35                  40                  45
```

-continued

```
Ile Tyr His Lys Pro Ile Ile Met Ser Val Gly Ala Ala Ile Leu
 50              55                  60

Leu Phe Gly Val Ala Ile Thr Cys Val Ala Tyr Ile Leu Glu Glu Lys
 65                  70                  75                  80

His Lys Val Val Gln Val Leu Arg Met Ile Gly Pro Ala Phe Leu Ser
                 85                  90                  95

Leu Gly Leu Met Met Leu Val Cys Gly Leu Val Trp Val Pro Ile Ile
                100                 105                 110

Lys Lys Lys Gln Lys Gln Arg Gln Lys Ser Asn Phe Phe Gln Ser Leu
                115                 120                 125

Lys Phe Phe Leu Leu Asn Arg
                130             135

<210> SEQ ID NO 15
<211> LENGTH: 993
<212> TYPE: DNA
<213> ORGANISM: Homo sapiens
<220> FEATURE:
<221> NAME/KEY: CDS
<222> LOCATION: (1)..(966)
<223> OTHER INFORMATION: Mrg1

<400> SEQUENCE: 15
```

| | | |
|---|---|---|
| atg gat cca acc atc tca acc ttg gac aca gaa ctg aca cca atc aac<br>Met Asp Pro Thr Ile Ser Thr Leu Asp Thr Glu Leu Thr Pro Ile Asn<br>1                     5                    10                  15 | 48 |
| gga act gag gag act ctt tgc tac aag cag acc ttg agc ctc acg gtg<br>Gly Thr Glu Glu Thr Leu Cys Tyr Lys Gln Thr Leu Ser Leu Thr Val<br>                 20                    25                  30 | 96 |
| ctg acg tgc atc gtt tcc ctt gtc ggg ctg aca gga aac gca gtt gtg<br>Leu Thr Cys Ile Val Ser Leu Val Gly Leu Thr Gly Asn Ala Val Val<br>                    35                    40                  45 | 144 |
| ctc tgg ctc ctg ggc tgc cgc atg cgc agg aac gcc ttc tcc atc tac<br>Leu Trp Leu Leu Gly Cys Arg Met Arg Arg Asn Ala Phe Ser Ile Tyr<br>50                    55                    60 | 192 |
| atc ctc aac ttg gcc gca gca gac ttc ctc ttc ctc agc ggc cgc ctt<br>Ile Leu Asn Leu Ala Ala Ala Asp Phe Leu Phe Leu Ser Gly Arg Leu<br>65                      70                    75                  80 | 240 |
| ata tat tcc ctg tta agc ttc atc agt atc ccc cat acc atc tct aaa<br>Ile Tyr Ser Leu Leu Ser Phe Ile Ser Ile Pro His Thr Ile Ser Lys<br>                    85                    90                  95 | 288 |
| atc ctc tat cct gtg atg atg ttt tcc tac ttt gca ggc ctg agc ttt<br>Ile Leu Tyr Pro Val Met Met Phe Ser Tyr Phe Ala Gly Leu Ser Phe<br>                 100                 105                 110 | 336 |
| ctg agt gcc gtg agc acc gag cgc tgc ctg tcc gtc ctg tgg ccc atc<br>Leu Ser Ala Val Ser Thr Glu Arg Cys Leu Ser Val Leu Trp Pro Ile<br>                 115                 120                 125 | 384 |
| tgg tac cgc tgc cac cgc ccc aca cac ctg tca gcg gtg gtg tgt gtc<br>Trp Tyr Arg Cys His Arg Pro Thr His Leu Ser Ala Val Val Cys Val<br>              130                 135                 140 | 432 |
| ctg ctc tgg gcc ctg tcc ctg ctg cgg agc atc ctg gag tgg atg tta<br>Leu Leu Trp Ala Leu Ser Leu Leu Arg Ser Ile Leu Glu Trp Met Leu<br>145                     150                 155                 160 | 480 |
| tgt ggc ttc ctg ttc agt ggt gct gat tct gct tgg tgt caa aca tca<br>Cys Gly Phe Leu Phe Ser Gly Ala Asp Ser Ala Trp Cys Gln Thr Ser<br>                 165                 170                 175 | 528 |
| gat ttc atc aca gtc gcg tgg ctg att ttt tta tgt gtg gtt ctc tgt<br>Asp Phe Ile Thr Val Ala Trp Leu Ile Phe Leu Cys Val Val Leu Cys<br>              180                 185                 190 | 576 |

```
ggg tcc agc ctg gtc ctg ctg atc agg att ctc tgt gga tcc cgg aag    624
Gly Ser Ser Leu Val Leu Leu Ile Arg Ile Leu Cys Gly Ser Arg Lys
        195                 200                 205 ata ccg ctg acc agg ctg tac gtg acc atc ctg ctc aca gta ctg gtc    672
Ile Pro Leu Thr Arg Leu Tyr Val Thr Ile Leu Leu Thr Val Leu Val
    210                 215                 220 ttc ctc ctc tgt ggc ctg ccc ttt ggc att cag ttt ttc cta ttt tta    720
Phe Leu Leu Cys Gly Leu Pro Phe Gly Ile Gln Phe Phe Leu Phe Leu
225                 230                 235                 240 tgg atc cac gtg gac agg gaa gtc tta ttt tgt cat gtt cat cta gtt    768
Trp Ile His Val Asp Arg Glu Val Leu Phe Cys His Val His Leu Val
                245                 250                 255 tct att ttc ctg tcc gct ctt aac agc agt gcc aac ccc atc att tac    816
Ser Ile Phe Leu Ser Ala Leu Asn Ser Ser Ala Asn Pro Ile Ile Tyr
            260                 265                 270 ttc ttc gtg ggc tcc ttt agg cag cgt caa aat agg cag aac ctg aag    864
Phe Phe Val Gly Ser Phe Arg Gln Arg Gln Asn Arg Gln Asn Leu Lys
        275                 280                 285 ctg gtt ctc cag agg gct ctg cag gac gcg tct gag gtg gat gaa ggt    912
Leu Val Leu Gln Arg Ala Leu Gln Asp Ala Ser Glu Val Asp Glu Gly
    290                 295                 300 gga ggg cag ctt cct gag gaa atc ctg gag ctg tcg gga agc aga ttg    960
Gly Gly Gln Leu Pro Glu Glu Ile Leu Glu Leu Ser Gly Ser Arg Leu
305                 310                 315                 320 gag cag tgaggaagag cctctgccct gtcagac                              993
Glu Gln

<210> SEQ ID NO 16
<211> LENGTH: 322
<212> TYPE: PRT
<213> ORGANISM: Homo sapiens

<400> SEQUENCE: 16

Met Asp Pro Thr Ile Ser Thr Leu Asp Thr Glu Leu Thr Pro Ile Asn
 1               5                  10                  15

Gly Thr Glu Glu Thr Leu Cys Tyr Lys Gln Thr Leu Ser Leu Thr Val
            20                  25                  30

Leu Thr Cys Ile Val Ser Leu Val Gly Leu Thr Gly Asn Ala Val Val
        35                  40                  45

Leu Trp Leu Leu Gly Cys Arg Met Arg Arg Asn Ala Phe Ser Ile Tyr
    50                  55                  60

Ile Leu Asn Leu Ala Ala Ala Asp Phe Leu Phe Leu Ser Gly Arg Leu
65                  70                  75                  80

Ile Tyr Ser Leu Leu Ser Phe Ile Ser Ile Pro His Thr Ile Ser Lys
                85                  90                  95

Ile Leu Tyr Pro Val Met Met Phe Ser Tyr Phe Ala Gly Leu Ser Phe
            100                 105                 110

Leu Ser Ala Val Ser Thr Glu Arg Cys Leu Ser Val Leu Trp Pro Ile
        115                 120                 125

Trp Tyr Arg Cys His Arg Pro Thr His Leu Ser Ala Val Val Cys Val
    130                 135                 140

Leu Leu Trp Ala Leu Ser Leu Leu Arg Ser Ile Leu Glu Trp Met Leu
145                 150                 155                 160

Cys Gly Phe Leu Phe Ser Gly Ala Asp Ser Ala Trp Cys Gln Thr Ser
                165                 170                 175

Asp Phe Ile Thr Val Ala Trp Leu Ile Phe Leu Cys Val Val Leu Cys
            180                 185                 190
```

-continued

```
Gly Ser Ser Leu Val Leu Leu Ile Arg Ile Leu Cys Gly Ser Arg Lys
            195                 200                 205

Ile Pro Leu Thr Arg Leu Tyr Val Thr Ile Leu Leu Thr Val Leu Val
    210                 215                 220

Phe Leu Leu Cys Gly Leu Pro Phe Gly Ile Gln Phe Leu Phe Leu
225                 230                 235                 240

Trp Ile His Val Asp Arg Glu Val Leu Phe Cys His Val His Leu Val
                245                 250                 255

Ser Ile Phe Leu Ser Ala Leu Asn Ser Ser Ala Asn Pro Ile Ile Tyr
            260                 265                 270

Phe Phe Val Gly Ser Phe Arg Gln Arg Gln Asn Arg Gln Asn Leu Lys
        275                 280                 285

Leu Val Leu Gln Arg Ala Leu Gln Asp Ala Ser Glu Val Asp Glu Gly
    290                 295                 300

Gly Gly Gln Leu Pro Glu Ile Leu Glu Leu Ser Gly Ser Arg Leu
305                 310                 315                 320

Glu Gln
```

<210> SEQ ID NO 17
<211> LENGTH: 1039
<212> TYPE: DNA
<213> ORGANISM: Homo sapiens
<220> FEATURE:
<221> NAME/KEY: CDS
<222> LOCATION: (1)..(990)
<223> OTHER INFORMATION: Mrg2

<400> SEQUENCE: 17

```
atg gat cca acc acc ccg gcc tgg gga aca gaa agt aca aca gtg aat    48
Met Asp Pro Thr Thr Pro Ala Trp Gly Thr Glu Ser Thr Thr Val Asn
  1               5                  10                  15 gga aat gac caa gcc ctt ctt ctg ctt tgt ggc aag gag acc ctg atc    96
Gly Asn Asp Gln Ala Leu Leu Leu Leu Cys Gly Lys Glu Thr Leu Ile
             20                  25                  30 ccg gtc ttc ctg atc ctt ttc att gcc ctg gtc ggg ctg gta gga aac   144
Pro Val Phe Leu Ile Leu Phe Ile Ala Leu Val Gly Leu Val Gly Asn
         35                  40                  45 ggg ttt gtg ctc tgg ctc ctg ggc ttc cgc atg cgc agg aac gcc ttc   192
Gly Phe Val Leu Trp Leu Leu Gly Phe Arg Met Arg Arg Asn Ala Phe
     50                  55                  60 tct gtc tac gtc ctc agc ctg gcc ggg gcc gac ttc ctc ttc ctc tgc   240
Ser Val Tyr Val Leu Ser Leu Ala Gly Ala Asp Phe Leu Phe Leu Cys
 65                  70                  75                  80 ttc cag att ata aat tgc ctg gtg tac ctc agt aac ttc ttc tgt tcc   288
Phe Gln Ile Ile Asn Cys Leu Val Tyr Leu Ser Asn Phe Phe Cys Ser
                 85                  90                  95 atc tcc atc aat ttc cct agc ttc ttc acc act gtg atg acc tgt gcc   336
Ile Ser Ile Asn Phe Pro Ser Phe Phe Thr Thr Val Met Thr Cys Ala
            100                 105                 110 tac ctt gca ggc ctg agc atg ctg agc acc gtc agc acc gag cgc tgc   384
Tyr Leu Ala Gly Leu Ser Met Leu Ser Thr Val Ser Thr Glu Arg Cys
        115                 120                 125 ctg tcc gtc ctg tgg ccc atc tgg tat cgc tgc cgc gcc cca aga cac   432
Leu Ser Val Leu Trp Pro Ile Trp Tyr Arg Cys Arg Arg Pro Arg His
    130                 135                 140 ctg tca gcg gtc gtg tgt gtc ctg ctc tgg gcc ctg tcc cta ctg ctg   480
Leu Ser Ala Val Val Cys Val Leu Leu Trp Ala Leu Ser Leu Leu Leu
145                 150                 155                 160 agc atc ttg gaa ggg aag ttc tgt ggc ttc tta ttt agt gat ggt gac   528
Ser Ile Leu Glu Gly Lys Phe Cys Gly Phe Leu Phe Ser Asp Gly Asp
```

```
                Ser Ile Leu Glu Gly Lys Phe Cys Gly Phe Leu Phe Ser Asp Gly Asp
                                165                 170                 175 tct ggt tgg tgt cag aca ttt gat ttc atc act gca gcg tgg ctg att           576
Ser Gly Trp Cys Gln Thr Phe Asp Phe Ile Thr Ala Ala Trp Leu Ile
        180                 185                 190 ttt tta ttc atg gtt ctc tgt ggg tcc agt ctg gcc ctg ctg gtc agg           624
Phe Leu Phe Met Val Leu Cys Gly Ser Ser Leu Ala Leu Leu Val Arg
            195                 200                 205 atc ctc tgt ggc tcc agg ggt ctg cca ctg acc agg ctg tac ctg acc           672
Ile Leu Cys Gly Ser Arg Gly Leu Pro Leu Thr Arg Leu Tyr Leu Thr
        210                 215                 220 atc ctg ctc aca gtg ctg gtg ttc ctc ctc tgc ggc ctg ccc ttt ggc           720
Ile Leu Leu Thr Val Leu Val Phe Leu Leu Cys Gly Leu Pro Phe Gly
225                 230                 235                 240 att cag tgg ttc cta ata tta tgg atc tgg aag gat tct gat gtc tta           768
Ile Gln Trp Phe Leu Ile Leu Trp Ile Trp Lys Asp Ser Asp Val Leu
                245                 250                 255 ttt tgt cat att cat cca gtt tca gtt gtc ctg tca tct ctt aac agc           816
Phe Cys His Ile His Pro Val Ser Val Val Leu Ser Ser Leu Asn Ser
            260                 265                 270 agt gcc aac ccc atc att tac ttc ttc gtg ggc tct ttt agg aag cag           864
Ser Ala Asn Pro Ile Ile Tyr Phe Phe Val Gly Ser Phe Arg Lys Gln
        275                 280                 285 tgg cgg ctg cag cag ccg atc ctc aag ctg gct ctc cag agg gct ctg           912
Trp Arg Leu Gln Gln Pro Ile Leu Lys Leu Ala Leu Gln Arg Ala Leu
    290                 295                 300 cag gac att gct gag gtg gat cac agt gaa gga tgc ttc cgt cag ggc           960
Gln Asp Ile Ala Glu Val Asp His Ser Glu Gly Cys Phe Arg Gln Gly
305                 310                 315                 320 acc ccg gag atg tcg aga agc agt ctg gtg tagagatgga cagcctctac            1010
Thr Pro Glu Met Ser Arg Ser Ser Leu Val
                325                 330 ttccatcaga tatatgtggc tttgagagg                                          1039

<210> SEQ ID NO 18
<211> LENGTH: 330
<212> TYPE: PRT
<213> ORGANISM: Homo sapiens

<400> SEQUENCE: 18

Met Asp Pro Thr Thr Pro Ala Trp Gly Thr Glu Ser Thr Thr Val Asn
 1               5                  10                  15

Gly Asn Asp Gln Ala Leu Leu Leu Cys Gly Lys Glu Thr Leu Ile
            20                  25                  30

Pro Val Phe Leu Ile Leu Phe Ile Ala Leu Val Gly Leu Val Gly Asn
        35                  40                  45

Gly Phe Val Leu Trp Leu Leu Gly Phe Arg Met Arg Arg Asn Ala Phe
    50                  55                  60

Ser Val Tyr Val Leu Ser Leu Ala Gly Ala Asp Phe Leu Phe Leu Cys
65                  70                  75                  80

Phe Gln Ile Ile Asn Cys Leu Val Tyr Leu Ser Asn Phe Phe Cys Ser
                85                  90                  95

Ile Ser Ile Asn Phe Pro Ser Phe Phe Thr Thr Val Met Thr Cys Ala
            100                 105                 110

Tyr Leu Ala Gly Leu Ser Met Leu Ser Thr Val Ser Thr Glu Arg Cys
        115                 120                 125

Leu Ser Val Leu Trp Pro Ile Trp Tyr Arg Cys Arg Arg Pro Arg His
    130                 135                 140
```

```
Leu Ser Ala Val Val Cys Val Leu Leu Trp Ala Leu Ser Leu Leu
145                 150                 155                 160

Ser Ile Leu Glu Gly Lys Phe Cys Gly Phe Leu Phe Ser Asp Gly Asp
                165                 170                 175

Ser Gly Trp Cys Gln Thr Phe Asp Phe Ile Thr Ala Ala Trp Leu Ile
            180                 185                 190

Phe Leu Phe Met Val Leu Cys Gly Ser Ser Leu Ala Leu Leu Val Arg
        195                 200                 205

Ile Leu Cys Gly Ser Arg Gly Leu Pro Leu Thr Arg Leu Tyr Leu Thr
    210                 215                 220

Ile Leu Leu Thr Val Leu Val Phe Leu Leu Cys Gly Leu Pro Phe Gly
225                 230                 235                 240

Ile Gln Trp Phe Leu Ile Leu Trp Ile Trp Lys Asp Ser Asp Val Leu
                245                 250                 255

Phe Cys His Ile His Pro Val Ser Val Val Leu Ser Ser Leu Asn Ser
            260                 265                 270

Ser Ala Asn Pro Ile Ile Tyr Phe Phe Val Gly Ser Phe Arg Lys Gln
        275                 280                 285

Trp Arg Leu Gln Gln Pro Ile Leu Lys Leu Ala Leu Gln Arg Ala Leu
    290                 295                 300

Gln Asp Ile Ala Glu Val Asp His Ser Glu Gly Cys Phe Arg Gln Gly
305                 310                 315                 320

Thr Pro Glu Met Ser Arg Ser Ser Leu Val
                325                 330

<210> SEQ ID NO 19
<211> LENGTH: 135
<212> TYPE: PRT
<213> ORGANISM: Homo sapiens
<220> FEATURE:
<223> OTHER INFORMATION: drg12

<400> SEQUENCE: 19

Met Glu Thr Leu Pro Lys Val Leu Glu Val Asp Glu Lys Ser Pro Glu
1               5                   10                  15

Ala Lys Asp Leu Leu Pro Ser Gln Thr Ala Ser Ser Leu Cys Ile Ser
                20                  25                  30

Ser Arg Ser Glu Ser Val Trp Thr Thr Thr Pro Arg Ser Asn Trp Glu
            35                  40                  45

Ile Tyr Arg Lys Pro Ile Val Ile Met Ser Val Gly Gly Ala Ile Leu
        50                  55                  60

Leu Phe Gly Val Val Ile Thr Cys Leu Ala Tyr Thr Leu Lys Leu Ser
65                  70                  75                  80

Asp Lys Ser Leu Ser Ile Leu Lys Met Val Gly Pro Gly Phe Leu Ser
                85                  90                  95

Leu Gly Leu Met Met Leu Val Cys Gly Leu Val Trp Val Pro Ile Ile
            100                 105                 110

Lys Lys Lys Gln Lys His Arg Gln Lys Ser Asn Phe Leu Arg Ser Leu
        115                 120                 125

Lys Ser Phe Phe Leu Thr Arg
    130                 135

<210> SEQ ID NO 20
<211> LENGTH: 970
<212> TYPE: DNA
<213> ORGANISM: Homo sapiens
```

```
<220> FEATURE:
<221> NAME/KEY: CDS
<222> LOCATION: (83)..(943)
<223> OTHER INFORMATION: Mrg9

<400> SEQUENCE: 20
gtgtcaccaa cagcacccac aacaaatcca atggacaaac ctctttggaa gtatggacat      60
ctggattctg acccgaaact ag atg atc atc ata ttc aga ctg gtt ggg atg     112
                         Met Ile Ile Ile Phe Arg Leu Val Gly Met
                           1               5                  10 aca gga aat gcc att gtg ttc tgg ctc ctg ggc ttc agc ttg cac agg      160
Thr Gly Asn Ala Ile Val Phe Trp Leu Leu Gly Phe Ser Leu His Arg
             15                  20                  25 aat gcc ttc tca gtc tac att tta aac ttg gcc ctt gct gac ttc gtc      208
Asn Ala Phe Ser Val Tyr Ile Leu Asn Leu Ala Leu Ala Asp Phe Val
         30                  35                  40 ttc ctc ctc tgt cac atc ata gat tcc atg ctg ctt ctt ctc act gtt      256
Phe Leu Leu Cys His Ile Ile Asp Ser Met Leu Leu Leu Leu Thr Val
     45                  50                  55 ttc tac ccc aac aat atc ttt tct ggg tac ttt tac acc atc atg acg      304
Phe Tyr Pro Asn Asn Ile Phe Ser Gly Tyr Phe Tyr Thr Ile Met Thr
 60                  65                  70 gtt ccc tac atc gca ggc ctg agc atg ctc agt gcc atc agc act gag      352
Val Pro Tyr Ile Ala Gly Leu Ser Met Leu Ser Ala Ile Ser Thr Glu
 75                  80                  85                  90 ctc tgc ctg tct gtc ctg tgc ccc atc tgg tat cgc tgc cac cac cca      400
Leu Cys Leu Ser Val Leu Cys Pro Ile Trp Tyr Arg Cys His His Pro
             95                 100                 105 gaa cac aca tca act gtc atg tgt gct gcg ata tgg gtc ctg ccc ctg      448
Glu His Thr Ser Thr Val Met Cys Ala Ala Ile Trp Val Leu Pro Leu
        110                 115                 120 ttg gtc tgc att ctg aat agg tat ttc tgc agt ttc tta gat atc aat      496
Leu Val Cys Ile Leu Asn Arg Tyr Phe Cys Ser Phe Leu Asp Ile Asn
    125                 130                 135 tat aac aat gac aaa cag tgt ctg gca tca aac ttc ttt act aga gca      544
Tyr Asn Asn Asp Lys Gln Cys Leu Ala Ser Asn Phe Phe Thr Arg Ala
    140                 145                 150 tac ctg atg ttt ttg ttt gtg gtc ctt tgt ctg tcc agc atg gct ctg      592
Tyr Leu Met Phe Leu Phe Val Val Leu Cys Leu Ser Ser Met Ala Leu
155                 160                 165                 170 ctg gcc agg ttg ttc tgt ggc act ggg cag atg aag ctt acc aga ttg      640
Leu Ala Arg Leu Phe Cys Gly Thr Gly Gln Met Lys Leu Thr Arg Leu
                175                 180                 185 tac gtg acc atc atg ctg act gtt ttg ggt ttt ctc ctc tgt ggg ttg      688
Tyr Val Thr Ile Met Leu Thr Val Leu Gly Phe Leu Leu Cys Gly Leu
            190                 195                 200 ccc ttt gtc atc tac tac ttc ctg tta ttc aat att aag gat ggt ttt      736
Pro Phe Val Ile Tyr Tyr Phe Leu Leu Phe Asn Ile Lys Asp Gly Phe
        205                 210                 215 tgt tta ttt gat ttt aga ttt tat atg tca aca cat gtc ctg act gct      784
Cys Leu Phe Asp Phe Arg Phe Tyr Met Ser Thr His Val Leu Thr Ala
    220                 225                 230 att aac aac tgt gcc aac ccc ata att tac ttt ttc gag ggc tcc ttc      832
Ile Asn Asn Cys Ala Asn Pro Ile Ile Tyr Phe Phe Glu Gly Ser Phe
235                 240                 245                 250 agg cat cag ttg aag cac cag acc ctc aaa atg gtt ctc cag agt gta      880
Arg His Gln Leu Lys His Gln Thr Leu Lys Met Val Leu Gln Ser Val
                255                 260                 265 ctg cag gac act cct gag ata gct gaa aat atg gtg gag atg tca aga      928
Leu Gln Asp Thr Pro Glu Ile Ala Glu Asn Met Val Glu Met Ser Arg
```

```
                      270              275              280
aac ata cca aag cca tgatgaaaag cctttgcctg gacctca                    970
Asn Ile Pro Lys Pro
        285

<210> SEQ ID NO 21
<211> LENGTH: 287
<212> TYPE: PRT
<213> ORGANISM: Homo sapiens

<400> SEQUENCE: 21

Met Ile Ile Ile Phe Arg Leu Val Gly Met Thr Gly Asn Ala Ile Val
  1               5                  10                  15

Phe Trp Leu Leu Gly Phe Ser Leu His Arg Asn Ala Phe Ser Val Tyr
             20                  25                  30

Ile Leu Asn Leu Ala Leu Ala Asp Phe Val Phe Leu Leu Cys His Ile
         35                  40                  45

Ile Asp Ser Met Leu Leu Leu Leu Thr Val Phe Tyr Pro Asn Asn Ile
     50                  55                  60

Phe Ser Gly Tyr Phe Tyr Thr Ile Met Thr Val Pro Tyr Ile Ala Gly
 65                  70                  75                  80

Leu Ser Met Leu Ser Ala Ile Ser Thr Glu Leu Cys Leu Ser Val Leu
                 85                  90                  95

Cys Pro Ile Trp Tyr Arg Cys His His Pro Glu His Thr Ser Thr Val
            100                 105                 110

Met Cys Ala Ala Ile Trp Val Leu Pro Leu Leu Val Cys Ile Leu Asn
        115                 120                 125

Arg Tyr Phe Cys Ser Phe Leu Asp Ile Asn Tyr Asn Asn Asp Lys Gln
    130                 135                 140

Cys Leu Ala Ser Asn Phe Phe Thr Arg Ala Tyr Leu Met Phe Leu Phe
145                 150                 155                 160

Val Val Leu Cys Leu Ser Ser Met Ala Leu Leu Ala Arg Leu Phe Cys
                165                 170                 175

Gly Thr Gly Gln Met Lys Leu Thr Arg Leu Tyr Val Thr Ile Met Leu
            180                 185                 190

Thr Val Leu Gly Phe Leu Leu Cys Gly Leu Pro Phe Val Ile Tyr Tyr
        195                 200                 205

Phe Leu Leu Phe Asn Ile Lys Asp Gly Phe Cys Leu Phe Asp Phe Arg
    210                 215                 220

Phe Tyr Met Ser Thr His Val Leu Thr Ala Ile Asn Asn Cys Ala Asn
225                 230                 235                 240

Pro Ile Ile Tyr Phe Phe Glu Gly Ser Phe Arg His Gln Leu Lys His
                245                 250                 255

Gln Thr Leu Lys Met Val Leu Gln Ser Val Leu Gln Asp Thr Pro Glu
            260                 265                 270

Ile Ala Glu Asn Met Val Glu Met Ser Arg Asn Ile Pro Lys Pro
        275                 280                 285

<210> SEQ ID NO 22
<211> LENGTH: 1024
<212> TYPE: DNA
<213> ORGANISM: Homo sapiens
<220> FEATURE:
<221> NAME/KEY: CDS
<222> LOCATION: (16)..(918)
<223> OTHER INFORMATION: Mrg10

<400> SEQUENCE: 22
```

-continued

```
ccagtgcacg aaacc atg cat aga agt atc agc atc agg att ctg ata aca         51
              Met His Arg Ser Ile Ser Ile Arg Ile Leu Ile Thr
              1               5                   10 aac ttg atg atc gtc atc ctc gga cta gtc ggg ctg aca gga aac gcc          99
Asn Leu Met Ile Val Ile Leu Gly Leu Val Gly Leu Thr Gly Asn Ala
            15                  20                  25 att gtg ttc tgg ctc ctg ctc ttc cgc ttg cgc agg aac gcc ttc tca         147
Ile Val Phe Trp Leu Leu Leu Phe Arg Leu Arg Arg Asn Ala Phe Ser
        30                  35                  40 atc tac atc cta aac ttg gcc ctg gct gac ttc ctc ttc ctc ctc tgc         195
Ile Tyr Ile Leu Asn Leu Ala Leu Ala Asp Phe Leu Phe Leu Leu Cys
45                  50                  55                  60 cac atc ata gct tcc aca gag cat att ctc acg ttt tcc tcc ccc aac         243
His Ile Ile Ala Ser Thr Glu His Ile Leu Thr Phe Ser Ser Pro Asn
                65                  70                  75 agt atc ttt atc aat tgc ctt tac acc ttc agg gtg ctt ctc tac atc         291
Ser Ile Phe Ile Asn Cys Leu Tyr Thr Phe Arg Val Leu Leu Tyr Ile
            80                  85                  90 gca ggc ctg agc atg ctc agt gcc atc agc att gag cgc tgc ctg tct         339
Ala Gly Leu Ser Met Leu Ser Ala Ile Ser Ile Glu Arg Cys Leu Ser
        95                  100                 105 gtc atg tgc ccc atc tgg tat cgc tgc cac agc cca gaa cac aca tca         387
Val Met Cys Pro Ile Trp Tyr Arg Cys His Ser Pro Glu His Thr Ser
110                 115                 120 act gtc atg tgt gct atg atc tgg gtc ctg tct cta ttg ctc tgc att         435
Thr Val Met Cys Ala Met Ile Trp Val Leu Ser Leu Leu Leu Cys Ile
125                 130                 135                 140 ctg tat agg tat ttc tgc ggc ttc ttg gat acc aaa tat gaa gat gac         483
Leu Tyr Arg Tyr Phe Cys Gly Phe Leu Asp Thr Lys Tyr Glu Asp Asp
                145                 150                 155 tat ggg tgt cta gca atg aac ttc ctt act acc gca tac ctg atg ttt         531
Tyr Gly Cys Leu Ala Met Asn Phe Leu Thr Thr Ala Tyr Leu Met Phe
            160                 165                 170 ttg ttt gta gtc ctc tgt gtg tcc agc ctg gct ctg ctg gcc agg ttg         579
Leu Phe Val Val Leu Cys Val Ser Ser Leu Ala Leu Leu Ala Arg Leu
        175                 180                 185 ttc tgt ggc gct gga cgg atg aag ctt acc aga tta tac gtg acc atc         627
Phe Cys Gly Ala Gly Arg Met Lys Leu Thr Arg Leu Tyr Val Thr Ile
190                 195                 200 acg ctg acc ctt ttg gtt ttt ctc ctc tgc ggg ttg ccc tgt ggc ttc         675
Thr Leu Thr Leu Leu Val Phe Leu Leu Cys Gly Leu Pro Cys Gly Phe
205                 210                 215                 220 tac tgg ttc ctg tta tcc aaa att aag aat gtt ttt act gta ttt gaa         723
Tyr Trp Phe Leu Leu Ser Lys Ile Lys Asn Val Phe Thr Val Phe Glu
                225                 230                 235 ttt agt ctt tat ctg gca tca gtt gtc ctg act gct att aac agc tgt         771
Phe Ser Leu Tyr Leu Ala Ser Val Val Leu Thr Ala Ile Asn Ser Cys
            240                 245                 250 gcc aac ccc atc att tac ttc ttt gtg ggc tca ttc agg cat cgg ttg         819
Ala Asn Pro Ile Ile Tyr Phe Phe Val Gly Ser Phe Arg His Arg Leu
        255                 260                 265 aag cac cag acc ctc aaa atg gtt ctc cag agt gca ctg cag gac act         867
Lys His Gln Thr Leu Lys Met Val Leu Gln Ser Ala Leu Gln Asp Thr
270                 275                 280 cct gag aca cct gaa aac atg gtg gag atg tca aga aac aaa gca gag         915
Pro Glu Thr Pro Glu Asn Met Val Glu Met Ser Arg Asn Lys Ala Glu
285                 290                 295                 300 ctg tgatgaagag cctctgcccg gacctcagag gtggctttgg agtgagcact             968
Leu
```

-continued gccctgctgc acttggccac tgtccactct cctctcagct tactcacttg gcatgc        1024

<210> SEQ ID NO 23
<211> LENGTH: 301
<212> TYPE: PRT
<213> ORGANISM: Homo sapiens

<400> SEQUENCE: 23

Met His Arg Ser Ile Ser Ile Arg Ile Leu Ile Thr Asn Leu Met Ile
 1               5                  10                  15

Val Ile Leu Gly Leu Val Gly Leu Thr Gly Asn Ala Ile Val Phe Trp
            20                  25                  30

Leu Leu Leu Phe Arg Leu Arg Arg Asn Ala Phe Ser Ile Tyr Ile Leu
        35                  40                  45

Asn Leu Ala Leu Ala Asp Phe Leu Phe Leu Leu Cys His Ile Ile Ala
    50                  55                  60

Ser Thr Glu His Ile Leu Thr Phe Ser Ser Pro Asn Ser Ile Phe Ile
65                  70                  75                  80

Asn Cys Leu Tyr Thr Phe Arg Val Leu Leu Tyr Ile Ala Gly Leu Ser
                85                  90                  95

Met Leu Ser Ala Ile Ser Ile Glu Arg Cys Leu Ser Val Met Cys Pro
            100                 105                 110

Ile Trp Tyr Arg Cys His Ser Pro Glu His Thr Ser Thr Val Met Cys
        115                 120                 125

Ala Met Ile Trp Val Leu Ser Leu Leu Leu Cys Ile Leu Tyr Arg Tyr
    130                 135                 140

Phe Cys Gly Phe Leu Asp Thr Lys Tyr Glu Asp Asp Tyr Gly Cys Leu
145                 150                 155                 160

Ala Met Asn Phe Leu Thr Thr Ala Tyr Leu Met Phe Leu Phe Val Val
                165                 170                 175

Leu Cys Val Ser Ser Leu Ala Leu Leu Ala Arg Leu Phe Cys Gly Ala
            180                 185                 190

Gly Arg Met Lys Leu Thr Arg Leu Tyr Val Thr Ile Thr Leu Thr Leu
        195                 200                 205

Leu Val Phe Leu Leu Cys Gly Leu Pro Cys Gly Phe Tyr Trp Phe Leu
    210                 215                 220

Leu Ser Lys Ile Lys Asn Val Phe Thr Val Phe Glu Phe Ser Leu Tyr
225                 230                 235                 240

Leu Ala Ser Val Val Leu Thr Ala Ile Asn Ser Cys Ala Asn Pro Ile
                245                 250                 255

Ile Tyr Phe Phe Val Gly Ser Phe Arg His Arg Leu Lys His Gln Thr
            260                 265                 270

Leu Lys Met Val Leu Gln Ser Ala Leu Gln Asp Thr Pro Glu Thr Pro
        275                 280                 285

Glu Asn Met Val Glu Met Ser Arg Asn Lys Ala Glu Leu
    290                 295                 300

<210> SEQ ID NO 24
<211> LENGTH: 1045
<212> TYPE: DNA
<213> ORGANISM: Homo sapiens
<220> FEATURE:
<221> NAME/KEY: CDS
<222> LOCATION: (82)..(1020)
<223> OTHER INFORMATION: Mrg11

<400> SEQUENCE: 24

```
tttgtgttca tagtgaatga ctaatttctt ctttgtgttc ccagtgcaga gtttctggcc        60
ctaaacacct cagcctcagc a atg tca ccc acg aca aca agt cca atg gac        111
                       Met Ser Pro Thr Thr Thr Ser Pro Met Asp
                         1               5                  10 gaa acc agc cct aga agt att gac atc gag tca ctg atc cca aac ttg        159
Glu Thr Ser Pro Arg Ser Ile Asp Ile Glu Ser Leu Ile Pro Asn Leu
                 15                  20                  25 atg atc atc atc ttt gga ctg gtt ggg ctg aca gga aat gcc att gtg        207
Met Ile Ile Ile Phe Gly Leu Val Gly Leu Thr Gly Asn Ala Ile Val
             30                  35                  40 ctc tgg ctc ctg ggc ttc tgc ttg cac agg aat gcc ttc tta gtc tac        255
Leu Trp Leu Leu Gly Phe Cys Leu His Arg Asn Ala Phe Leu Val Tyr
         45                  50                  55 atc cta aac ttg gcc ctg gct gac ttc ctc ttc ctt ctc tgt cac ttc        303
Ile Leu Asn Leu Ala Leu Ala Asp Phe Leu Phe Leu Leu Cys His Phe
     60                  65                  70 ata aat tca gca atg ttt ctt ctc aag gtt cct ata ccc aac ggt atc        351
Ile Asn Ser Ala Met Phe Leu Leu Lys Val Pro Ile Pro Asn Gly Ile
 75              80                  85                  90 ttt gtc tat tgc ttt tac acc atc aaa atg gtt ctc tac atc aca ggc        399
Phe Val Tyr Cys Phe Tyr Thr Ile Lys Met Val Leu Tyr Ile Thr Gly
             95                 100                 105 ctg agc atg ctc agt gcc atc agc act gag cgc tgc ctt tct gtc ctg        447
Leu Ser Met Leu Ser Ala Ile Ser Thr Glu Arg Cys Leu Ser Val Leu
         110                 115                 120 tgc ccc atc tgg tat cac tgc cgc cgc cca gaa cac aca tca act gtc        495
Cys Pro Ile Trp Tyr His Cys Arg Arg Pro Glu His Thr Ser Thr Val
     125                 130                 135 atg tgt gct gtg att tgg atc ttt tcc gtg ttg atc tgc att ctg aaa        543
Met Cys Ala Val Ile Trp Ile Phe Ser Val Leu Ile Cys Ile Leu Lys
 140                 145                 150 gaa tat ttc tgt gat ttc ttt ggt acc aaa ttg gga aat tac tat gtg        591
Glu Tyr Phe Cys Asp Phe Phe Gly Thr Lys Leu Gly Asn Tyr Tyr Val
155                 160                 165                 170 tgt cag gca tcc aac ttc ttt atg gga gca tac cta atg ttt ttg ttt        639
Cys Gln Ala Ser Asn Phe Phe Met Gly Ala Tyr Leu Met Phe Leu Phe
             175                 180                 185 gta gtc ctc tgt ctg tcc acc ctg gct ctg ctg gcc agg ttg ttc tgt        687
Val Val Leu Cys Leu Ser Thr Leu Ala Leu Leu Ala Arg Leu Phe Cys
         190                 195                 200 ggt gct gag aag atg aaa ttt acc aga tta ttc gtg acc atc atg ctg        735
Gly Ala Glu Lys Met Lys Phe Thr Arg Leu Phe Val Thr Ile Met Leu
     205                 210                 215 acc att ttg gtt ttt ctc ctc tgt ggg ttg cca tgg ggc ttc ttc tgg        783
Thr Ile Leu Val Phe Leu Leu Cys Gly Leu Pro Trp Gly Phe Phe Trp
 220                 225                 230 ttc ctg tta atc tgg att aag ggt ggt ttt agt gta cta gat tat aga        831
Phe Leu Leu Ile Trp Ile Lys Gly Gly Phe Ser Val Leu Asp Tyr Arg
235                 240                 245                 250 ctt tat ttg gca tca att gtc cta act gtt gtt aac agc tgt gcc aac        879
Leu Tyr Leu Ala Ser Ile Val Leu Thr Val Val Asn Ser Cys Ala Asn
             255                 260                 265 ccc atc att tac ttc ttc gtg gga tca ttc agg cat cgg ttg aag cac        927
Pro Ile Ile Tyr Phe Phe Val Gly Ser Phe Arg His Arg Leu Lys His
         270                 275                 280 cag acc ctc aaa atg gtt ctc cag agt gca ctg cag gac act cct gag        975
Gln Thr Leu Lys Met Val Leu Gln Ser Ala Leu Gln Asp Thr Pro Glu
     285                 290                 295
```

```
aca cat gaa aac atg gtg gag atg tca aga atc aaa gca gag cag      1020
Thr His Glu Asn Met Val Glu Met Ser Arg Ile Lys Ala Glu Gln
    300                 305                 310 tgatgaagag cctctgcctg gacct                                      1045
```

<210> SEQ ID NO 25
<211> LENGTH: 313
<212> TYPE: PRT
<213> ORGANISM: Homo sapiens

<400> SEQUENCE: 25

```
Met Ser Pro Thr Thr Ser Pro Met Asp Glu Thr Ser Pro Arg Ser
  1               5                  10                  15

Ile Asp Ile Glu Ser Leu Ile Pro Asn Leu Met Ile Ile Phe Gly
                 20                  25                  30

Leu Val Gly Leu Thr Gly Asn Ala Ile Val Leu Trp Leu Leu Gly Phe
             35                  40                  45

Cys Leu His Arg Asn Ala Phe Leu Val Tyr Ile Leu Asn Leu Ala Leu
     50                  55                  60

Ala Asp Phe Leu Phe Leu Cys His Phe Ile Asn Ser Ala Met Phe
 65                  70                  75                  80

Leu Leu Lys Val Pro Ile Pro Asn Gly Ile Phe Val Tyr Cys Phe Tyr
                 85                  90                  95

Thr Ile Lys Met Val Leu Tyr Ile Thr Gly Leu Ser Met Leu Ser Ala
                100                 105                 110

Ile Ser Thr Glu Arg Cys Leu Ser Val Leu Cys Pro Ile Trp Tyr His
            115                 120                 125

Cys Arg Arg Pro Glu His Thr Ser Thr Val Met Cys Ala Val Ile Trp
130                 135                 140

Ile Phe Ser Val Leu Ile Cys Ile Leu Lys Glu Tyr Phe Cys Asp Phe
145                 150                 155                 160

Phe Gly Thr Lys Leu Gly Asn Tyr Tyr Val Cys Gln Ala Ser Asn Phe
                165                 170                 175

Phe Met Gly Ala Tyr Leu Met Phe Leu Phe Val Val Leu Cys Leu Ser
            180                 185                 190

Thr Leu Ala Leu Leu Ala Arg Leu Phe Cys Gly Ala Glu Lys Met Lys
        195                 200                 205

Phe Thr Arg Leu Phe Val Thr Ile Met Leu Thr Ile Leu Val Phe Leu
    210                 215                 220

Leu Cys Gly Leu Pro Trp Gly Phe Phe Trp Phe Leu Leu Ile Trp Ile
225                 230                 235                 240

Lys Gly Gly Phe Ser Val Leu Asp Tyr Arg Leu Tyr Leu Ala Ser Ile
                245                 250                 255

Val Leu Thr Val Val Asn Ser Cys Ala Asn Pro Ile Ile Tyr Phe Phe
            260                 265                 270

Val Gly Ser Phe Arg His Arg Leu Lys His Gln Thr Leu Lys Met Val
        275                 280                 285

Leu Gln Ser Ala Leu Gln Asp Thr Pro Glu Thr His Glu Asn Met Val
    290                 295                 300

Glu Met Ser Arg Ile Lys Ala Glu Gln
305                 310
```

<210> SEQ ID NO 26
<211> LENGTH: 980
<212> TYPE: DNA
<213> ORGANISM: Homo sapiens

```
<220> FEATURE:
<221> NAME/KEY: CDS
<222> LOCATION: (45)..(959)
<223> OTHER INFORMATION: Mrg12

<400> SEQUENCE: 26
tagacacctc agcatatgca atggcaccca cgaccacaaa tcca atg gac aaa acc        56
                                             Met Asp Lys Thr
                                              1 atc ctt gga agt att gac atc gag acc ctg atc cga cat ttg atg atc       104
Ile Leu Gly Ser Ile Asp Ile Glu Thr Leu Ile Arg His Leu Met Ile
  5              10                  15                  20 atc atc ttc gga ctg gtc ggg ctg aca gga aat gcc att gtg ttc tgg       152
Ile Ile Phe Gly Leu Val Gly Leu Thr Gly Asn Ala Ile Val Phe Trp
             25                  30                  35 ctc ctg ggc ttc cac ttg cac agg aat gcc ttc tta gtc tac atc ata       200
Leu Leu Gly Phe His Leu His Arg Asn Ala Phe Leu Val Tyr Ile Ile
         40                  45                  50 aac ttg gcc ctg gct gac ttc ttc tat ctg ctc tgt cac atc ata aat       248
Asn Leu Ala Leu Ala Asp Phe Phe Tyr Leu Leu Cys His Ile Ile Asn
     55                  60                  65 tcc ata atg ttt ctt ctc aag gtt ccc tca ccc aac att atc ttg gac       296
Ser Ile Met Phe Leu Leu Lys Val Pro Ser Pro Asn Ile Ile Leu Asp
 70                  75                  80 cat tgc ttt tac acc atc atg ata gtt ctc tac atc aca ggc ctg agc       344
His Cys Phe Tyr Thr Ile Met Ile Val Leu Tyr Ile Thr Gly Leu Ser
 85                  90                  95                 100 atg ctc agc gcc atc agc act gag cgc tgc ctg tct gtc ctg tgc ccc       392
Met Leu Ser Ala Ile Ser Thr Glu Arg Cys Leu Ser Val Leu Cys Pro
                 105                 110                 115 atc tgg tat cgc tgc cac cgt cca gaa cac aca tca act gtc atg tgt       440
Ile Trp Tyr Arg Cys His Arg Pro Glu His Thr Ser Thr Val Met Cys
                 120                 125                 130 gct gtg atc tgg gta atg tcc ctg ttg atc tct att ctc aat gga tat       488
Ala Val Ile Trp Val Met Ser Leu Leu Ile Ser Ile Leu Asn Gly Tyr
             135                 140                 145 ttc tgt aat ttc tct agt ccc aaa tat gta aat aac tct gtg tgt cag       536
Phe Cys Asn Phe Ser Ser Pro Lys Tyr Val Asn Asn Ser Val Cys Gln
         150                 155                 160 gca tca cac atc ttt atc aga aca tac cca ata ttt ttg ttt gta ctc       584
Ala Ser His Ile Phe Ile Arg Thr Tyr Pro Ile Phe Leu Phe Val Leu
165                 170                 175                 180 ctc tgt ctg tcc acc ctt gct ctg ctg gcc agg ttg ttc tct ggt gct       632
Leu Cys Leu Ser Thr Leu Ala Leu Leu Ala Arg Leu Phe Ser Gly Ala
                 185                 190                 195 ggg aag agg aaa ttt acc aga tta ttc gtg acc atc atg ctg gcc att       680
Gly Lys Arg Lys Phe Thr Arg Leu Phe Val Thr Ile Met Leu Ala Ile
             200                 205                 210 ttg gtt ttt ctt ctc tgt ggg tta ccc ctg ggc ttc ttc tgg ttt ctg       728
Leu Val Phe Leu Leu Cys Gly Leu Pro Leu Gly Phe Phe Trp Phe Leu
         215                 220                 225 tca ccc tgg att gag gat cgt ttc att gta cta gat tat aga ctt ttt       776
Ser Pro Trp Ile Glu Asp Arg Phe Ile Val Leu Asp Tyr Arg Leu Phe
230                 235                 240 ttt gca tca gtt gtc cta act gtt gtt aac agc tgt gcc aac ccc atc       824
Phe Ala Ser Val Val Leu Thr Val Val Asn Ser Cys Ala Asn Pro Ile
245                 250                 255                 260 att tac ttc ttt gtg ggc tcc ttc agg cat cgg ttg aag caa cag acc       872
Ile Tyr Phe Phe Val Gly Ser Phe Arg His Arg Leu Lys Gln Gln Thr
                 265                 270                 275
```

```
ctc aaa atg ttt ctc cag aga gca ctg cag gac acc cct gag aca cct         920
Leu Lys Met Phe Leu Gln Arg Ala Leu Gln Asp Thr Pro Glu Thr Pro
        280                 285                 290 gaa aac atg gtg gag atg tca aga agc aaa gca gag ccg tgatgaagag          969
Glu Asn Met Val Glu Met Ser Arg Ser Lys Ala Glu Pro
            295                 300                 305 cctcttccag g                                                            980

<210> SEQ ID NO 27
<211> LENGTH: 305
<212> TYPE: PRT
<213> ORGANISM: Homo sapiens

<400> SEQUENCE: 27

Met Asp Lys Thr Ile Leu Gly Ser Ile Asp Ile Glu Thr Leu Ile Arg
 1               5                  10                  15

His Leu Met Ile Ile Ile Phe Gly Leu Val Gly Leu Thr Gly Asn Ala
             20                  25                  30

Ile Val Phe Trp Leu Leu Gly Phe His Leu His Arg Asn Ala Phe Leu
         35                  40                  45

Val Tyr Ile Ile Asn Leu Ala Leu Ala Asp Phe Phe Tyr Leu Leu Cys
     50                  55                  60

His Ile Ile Asn Ser Ile Met Phe Leu Leu Lys Val Pro Ser Pro Asn
 65                  70                  75                  80

Ile Ile Leu Asp His Cys Phe Tyr Thr Ile Met Ile Val Leu Tyr Ile
                 85                  90                  95

Thr Gly Leu Ser Met Leu Ser Ala Ile Ser Thr Glu Arg Cys Leu Ser
            100                 105                 110

Val Leu Cys Pro Ile Trp Tyr Arg Cys His Arg Pro Glu His Thr Ser
        115                 120                 125

Thr Val Met Cys Ala Val Ile Trp Val Met Ser Leu Leu Ile Ser Ile
    130                 135                 140

Leu Asn Gly Tyr Phe Cys Asn Phe Ser Ser Pro Lys Tyr Val Asn Asn
145                 150                 155                 160

Ser Val Cys Gln Ala Ser His Ile Phe Ile Arg Thr Tyr Pro Ile Phe
                165                 170                 175

Leu Phe Val Leu Leu Cys Leu Ser Thr Leu Ala Leu Leu Ala Arg Leu
            180                 185                 190

Phe Ser Gly Ala Gly Lys Arg Lys Phe Thr Arg Leu Phe Val Thr Ile
        195                 200                 205

Met Leu Ala Ile Leu Val Phe Leu Leu Cys Gly Leu Pro Leu Gly Phe
    210                 215                 220

Phe Trp Phe Leu Ser Pro Trp Ile Glu Asp Arg Phe Ile Val Leu Asp
225                 230                 235                 240

Tyr Arg Leu Phe Phe Ala Ser Val Val Leu Thr Val Val Asn Ser Cys
                245                 250                 255

Ala Asn Pro Ile Ile Tyr Phe Phe Val Gly Ser Phe Arg His Arg Leu
            260                 265                 270

Lys Gln Gln Thr Leu Lys Met Phe Leu Gln Arg Ala Leu Gln Asp Thr
        275                 280                 285

Pro Glu Thr Pro Glu Asn Met Val Glu Met Ser Arg Ser Lys Ala Glu
    290                 295                 300

Pro
305
```

-continued

<210> SEQ ID NO 28
<211> LENGTH: 408
<212> TYPE: DNA
<213> ORGANISM: Homo sapiens
<220> FEATURE:
<221> NAME/KEY: CDS
<222> LOCATION: (1)..(405)
<223> OTHER INFORMATION: Drg12

<400> SEQUENCE: 28

```
atg gag act ctc ccc aag gtt cta gag gtc gat gag aag tct cca gaa      48
Met Glu Thr Leu Pro Lys Val Leu Glu Val Asp Glu Lys Ser Pro Glu
 1               5                  10                  15 gcc aag gac ctg ctg ccc agc cag acc gcc agc tcc ctg tgc atc agc      96
Ala Lys Asp Leu Leu Pro Ser Gln Thr Ala Ser Ser Leu Cys Ile Ser
             20                  25                  30 tcc agg agc gag tct gtc tgg acc acc acc ccc agg agt aac tgg gaa     144
Ser Arg Ser Glu Ser Val Trp Thr Thr Thr Pro Arg Ser Asn Trp Glu
         35                  40                  45 atc tac cgc aag ccc atc gtt atc atg tca gtg ggc ggt gcc atc ctg     192
Ile Tyr Arg Lys Pro Ile Val Ile Met Ser Val Gly Gly Ala Ile Leu
     50                  55                  60 ctt ttc ggc gtg gtc atc acc tgc ttg gcc tac acc ttg aag ctg agt     240
Leu Phe Gly Val Val Ile Thr Cys Leu Ala Tyr Thr Leu Lys Leu Ser
 65                  70                  75                  80 gac aag agt ctc tcc atc ctc aaa atg gta ggg cct ggc ttc ctg tcc     288
Asp Lys Ser Leu Ser Ile Leu Lys Met Val Gly Pro Gly Phe Leu Ser
                 85                  90                  95 ctg gga ctc atg atg ctg gtg tgc ggg ctg gtg tgg gtg ccc atc atc     336
Leu Gly Leu Met Met Leu Val Cys Gly Leu Val Trp Val Pro Ile Ile
            100                 105                 110 aaa aag aaa cag aag cac aga cag aag tcg aat ttc tta cgc agc ctc     384
Lys Lys Lys Gln Lys His Arg Gln Lys Ser Asn Phe Leu Arg Ser Leu
        115                 120                 125 aag tcc ttc ttc ctg act cgc tga                                      408
Lys Ser Phe Phe Leu Thr Arg
    130                 135
```

<210> SEQ ID NO 29
<211> LENGTH: 135
<212> TYPE: PRT
<213> ORGANISM: Homo sapiens

<400> SEQUENCE: 29

```
Met Glu Thr Leu Pro Lys Val Leu Glu Val Asp Glu Lys Ser Pro Glu
 1               5                  10                  15

Ala Lys Asp Leu Leu Pro Ser Gln Thr Ala Ser Ser Leu Cys Ile Ser
             20                  25                  30

Ser Arg Ser Glu Ser Val Trp Thr Thr Thr Pro Arg Ser Asn Trp Glu
         35                  40                  45

Ile Tyr Arg Lys Pro Ile Val Ile Met Ser Val Gly Gly Ala Ile Leu
     50                  55                  60

Leu Phe Gly Val Val Ile Thr Cys Leu Ala Tyr Thr Leu Lys Leu Ser
 65                  70                  75                  80

Asp Lys Ser Leu Ser Ile Leu Lys Met Val Gly Pro Gly Phe Leu Ser
                 85                  90                  95

Leu Gly Leu Met Met Leu Val Cys Gly Leu Val Trp Val Pro Ile Ile
            100                 105                 110

Lys Lys Lys Gln Lys His Arg Gln Lys Ser Asn Phe Leu Arg Ser Leu
        115                 120                 125
```

```
Lys Ser Phe Phe Leu Thr Arg
    130                 135
```